(12) United States Patent
Park

(10) Patent No.: US 12,391,699 B2
(45) Date of Patent: Aug. 19, 2025

(54) HETEROCYCLIC COMPOUND, HOLE TRANSPORT COMPOSITION INCLUDING THE SAME, LIGHT-EMITTING DEVICE INCLUDING THE HOLE TRANSPORT COMPOSITION, METHOD OF MANUFACTURING THE LIGHT-EMITTING DEVICE, AND ELECTRONIC APPARATUS INCLUDING THE LIGHT-EMITTING DEVICE

(71) Applicant: Samsung Display Co., Ltd., Yongin-si (KR)

(72) Inventor: Junwoo Park, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 793 days.

(21) Appl. No.: 17/447,685

(22) Filed: Sep. 14, 2021

(65) Prior Publication Data

US 2022/0089604 A1    Mar. 24, 2022

(30) Foreign Application Priority Data

Sep. 18, 2020  (KR) .................. 10-2020-0120528

(51) Int. Cl.
*C07D 487/14* (2006.01)
*C07D 487/16* (2006.01)
(Continued)

(52) U.S. Cl.
CPC ....... *C07D 487/14* (2013.01); *H10K 85/6572* (2023.02); *H10K 50/15* (2023.02)

(58) Field of Classification Search
CPC .................. C07D 487/14; H10K 85/6572
See application file for complete search history.

(56) References Cited

U.S. PATENT DOCUMENTS

| 6,027,849 A | 2/2000 | Vogel |
| 6,814,887 B2 | 11/2004 | Okunaka et al. |

(Continued)

FOREIGN PATENT DOCUMENTS

| EP | 1 717 239 A1 | 11/2006 |
| EP | 3 489 240 A1 | 5/2019 |

(Continued)

OTHER PUBLICATIONS

Arthur Connell et al., "Low cost triazatruxene hole transporting material for >20% efficiency perovskite solar cells", Journal of Materials Chemistry C, 2019, p. 5235-5243, vol. 7, the Royal Society of Chemistry.

(Continued)

*Primary Examiner* — Jennifer A Boyd
*Assistant Examiner* — Rachel Simbana
(74) *Attorney, Agent, or Firm* — Womble Bond Dickinson (US) LLP

(57) ABSTRACT

Provided are a heterocyclic compound represented by Formula 1, a hole transport composition containing the same, a light-emitting device including the hole transport composition, a method of manufacturing the light-emitting device, and an electronic apparatus including the light-emitting device, wherein each substituent in Formula 1 is the same as described in the present specification.

(Continued)

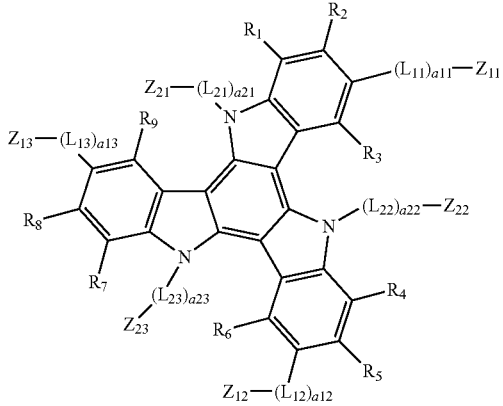

Formula 1

19 Claims, 3 Drawing Sheets

(51) Int. Cl.
   *H10K 50/15* (2023.01)
   *H10K 85/60* (2023.01)

(56) References Cited

U.S. PATENT DOCUMENTS

| | | |
|---|---|---|
| 7,632,954 B2 | 12/2009 | Hiyoshi et al. |
| 9,472,770 B2 | 10/2016 | Ha et al. |
| 2004/0106004 A1 | 6/2004 | Li |
| 2006/0035110 A1 | 2/2006 | Kathirgamanathan et al. |
| 2006/0099327 A1 | 5/2006 | Horn et al. |
| 2011/0121279 A1 | 5/2011 | Baranoff et al. |
| 2012/0187387 A1 | 7/2012 | Sekiguchi et al. |
| 2014/0131628 A1 | 5/2014 | D'Iavari et al. |
| 2016/0111656 A1* | 4/2016 | Ha .................. C08F 12/26 526/310 |
| 2020/0144513 A1 | 5/2020 | Hatakeyama et al. |

FOREIGN PATENT DOCUMENTS

| | | |
|---|---|---|
| KR | 10-2004-0106530 A | 12/2004 |
| KR | 10-2011-0090566 A | 8/2011 |
| KR | 10-2013-0013234 A | 2/2013 |
| KR | 10-2016-0047062 A | 5/2016 |
| KR | 10-2019-0025065 A | 3/2019 |
| WO | WO 2005/077956 A1 | 8/2005 |

OTHER PUBLICATIONS

Azin Babaei et al., "Solution processed organic light-emitting diodes using a triazatruxene crosslinkable hole transporting material", RSC Advances, 2018, p. 35719-35723, vol. 8, the Royal Society of Chemistry.

Lionel Derue et al., "Thermal Stabilisation of Polymer-Fullerene Bulk Heterojunction Morphology for Efficient Photovoltaic Solar Cells", Advanced Materials, 2014, p. 1-8, vol. 26, Wiley Online Library.

Robert A. Valentine et al., "New indole trimers as precursors for molecular electronic materials", Tetrahedron Letters, 2012, p. 657-660, vol. 53, Elsevier.

Jungwoo Park, et al., "Facile Photo-Crosslinking of Azide-Containing Hole-Transporting Polymers for Highly Efficient, Solution-Processed, Multilayer Organic Light Emitting Devices", Adv. Funct. Mater. 2014, pp. 1-9.

US Office Action dated Feb. 1, 2016, issued in U.S. Appl. No. 14/656,148 (9 pages).

* cited by examiner

HETEROCYCLIC COMPOUND, HOLE TRANSPORT COMPOSITION INCLUDING THE SAME, LIGHT-EMITTING DEVICE INCLUDING THE HOLE TRANSPORT COMPOSITION, METHOD OF MANUFACTURING THE LIGHT-EMITTING DEVICE, AND ELECTRONIC APPARATUS INCLUDING THE LIGHT-EMITTING DEVICE

CROSS-REFERENCE TO RELATED APPLICATION

This application claims priority to and the benefit of Korean Patent Application No. 10-2020-0120528, filed on Sep. 18, 2020, in the Korean Intellectual Property Office, the entire content of which is hereby incorporated by reference.

BACKGROUND

1. Field

One or more embodiments of the present disclosure relate to a heterocyclic compound, a hole transport composition including the heterocyclic compound, a light-emitting device including the hole transport composition, a method of manufacturing the light-emitting device, and an electronic apparatus including the light-emitting device.

2. Description of Related Art

Organic light-emitting devices (OLEDs) are self-emission devices that, as compared with other devices of the related art, have wide viewing angles, high contrast ratios, short response times, and excellent characteristics in terms of luminance, driving voltage, and response speed, and produce full-color images.

OLEDs may include a first electrode on a substrate, and a hole transport region, an emission layer, an electron transport region, and a second electrode sequentially stacked on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transition (or relax) from an excited state to a ground state to thereby generate light.

SUMMARY

One or more embodiments of the present disclosure include a novel heterocyclic compound, a hole transport composition including the same, a light-emitting device including the hole transport composition, and a method of manufacturing the light-emitting device. One or more embodiments include an electronic apparatus including a light-emitting device.

Additional aspects of embodiments will be set forth in part in the description which follows and, in part, will be apparent from the description, or may be learned by practice of the presented embodiments of the disclosure.

An aspect of an embodiment of the present disclosure provides a heterocyclic compound represented by Formula 1,

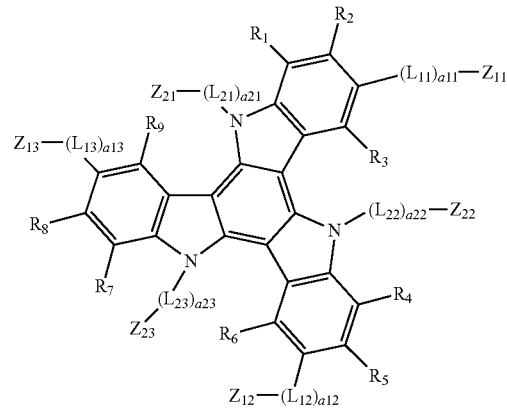

Formula 1 wherein, in Formula 1, $L_{11}$ to $L_{13}$ and $L_{21}$ to $L_{23}$ may each independently be a single bond, a $C_1$-$C_{20}$ alkylene group unsubstituted or substituted with at least one $R_{10a}$, a $C_2$-$C_{20}$ alkenylene group unsubstituted or substituted with at least one $R_{10a}$, or a $C_2$-$C_{20}$ alkynylene group unsubstituted or substituted with at least one $R_{10a}$, a11 to a13 and a21 to a23 may each independently be 0, 1, 2, 3, 4, or 5, $Z_{11}$ to $Z_{13}$, $Z_{21}$ to $Z_{23}$ and $R_1$ to $R_9$ may each independently be hydrogen, deuterium, an azide group (—$N_3$), —F, —Cl, —Br, —I, a hydroxyl group, a cyano group, a nitro group, an amidino group, a hydrazino group, a hydrazono group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a $C_1$-$C_{60}$ heteroaryloxy group unsubstituted or substituted with at least one $R_{10a}$, a $C_1$-$C_{60}$ heteroarylthio group unsubstituted or substituted with at least one $R_{10a}$, a monovalent non-aromatic condensed polycyclic group unsubstituted or substituted with at least one $R_{10a}$, a monovalent non-aromatic condensed heteropolycyclic group unsubstituted or substituted with at least one $R_{10a}$, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), or —P(=S)($Q_1$)($Q_2$), at least one selected from $Z_{11}$ to $Z_{13}$, $Z_{21}$ to $Z_{23}$, and $R_1$ to $R_9$ is —$N_3$, when each of $Z_{11}$ to $Z_{13}$ is —$N_3$, at least one selected from -($L_{21}$)$_{a21}$-$Z_{21}$, -($L_{22}$)$_{a22}$-$Z_{22}$, and -($L_{23}$)$_{a23}$-$Z_{23}$ is hydrogen, $R_{10a}$ may be:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si$(Q_{11})(Q_{12})(Q_{13})$, —N$(Q_{11})(Q_{12})$, —B$(Q_{11})(Q_{12})$, —C$(=O)(Q_{11})$, —S$(=O)_2(Q_{11})$, —P$(=O)(Q_{11})(Q_{12})$, or any combination thereof, a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si$(Q_{21})(Q_{22})(Q_{23})$, —N$(Q_{21})(Q_{22})$, —B$(Q_{21})(Q_{22})$, —C$(=O)(Q_{21})$, —S$(=O)_2(Q_{21})$, —P$(=O)(Q_{21})(Q_{22})$, or any combination thereof, or —Si$(Q_{31})(Q_{32})(Q_{33})$, —N$(Q_{31})(Q_{32})$, —B$(Q_{31})(Q_{32})$, —C$(=O)(Q_{31})$, —S$(=O)_2(Q_{31})$, or —P$(=O)(Q_{31})(Q_{32})$, wherein $Q_1$ to $Q_3$, $Q_{11}$ to $Q_{13}$, $Q_{21}$ to $Q_{23}$ and $Q_{31}$ to $Q_{33}$ may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, and the heterocyclic compound is not Compound B:

Compound B

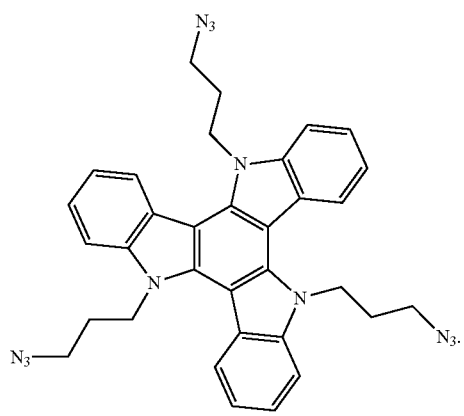

Another aspect of an embodiment of the present disclosure provides a hole transport composition including the heterocyclic compound.

Another aspect of an embodiment of the present disclosure provides a light-emitting device including: a first electrode; a second electrode facing the first electrode and an organic layer including an emission layer between the first electrode and the second electrode, wherein the light-emitting device includes the heterocyclic compound, a polymer containing a repeating unit derived from the heterocyclic compound, or any combination thereof.

Another aspect of an embodiment of the present disclosure provides a method of manufacturing a light-emitting device including forming a hole transport region on a first electrode, wherein, the forming the hole transport region includes a solution process using a hole transport composition, which includes the heterocyclic compound.

Another aspect of an embodiment of the present disclosure provides an electronic apparatus including the light-emitting device.

BRIEF DESCRIPTION OF THE DRAWINGS

Reference will now be made in more detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of embodiments of the present description. As used herein, the term "and/or" includes any and all combinations of one or more of the associated listed items. Throughout the disclosure, the expression "at least one of a, b or c" indicates only a, only b, only c, both a and b, both a and c, both b and c, all of a, b, and c, or variations thereof.

The above and other aspects and features of certain embodiments of the disclosure will be more apparent from the following description taken in conjunction with the accompanying drawings, in which.

DETAILED DESCRIPTION

Figure 1:
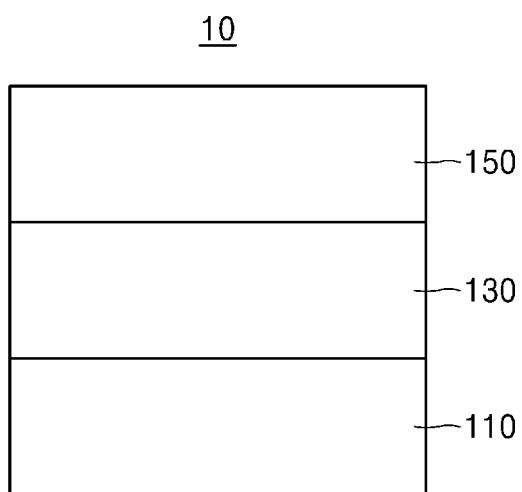
FIG. 1 is a schematic view of a light-emitting device according to an embodiment.

According to embodiments of the present disclosure, a heterocyclic compound is represented by Formula 1:

Formula 1

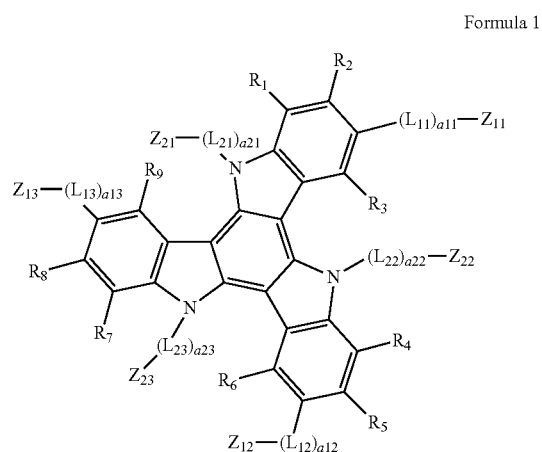

where $L_{11}$ to $L_{13}$ and $L_{21}$ to $L_{23}$ in Formula 1 may each independently be a single bond, a $C_1$-$C_{20}$ alkylene group unsubstituted or substituted with at least one $R_{10a}$ a $C_2$-$C_{20}$ alkenylene group unsubstituted or substituted with at least one $R_{10a}$, or a $C_2$-$C_{20}$ alkynylene group unsubstituted or substituted with at least one $R_{10a}$.

In an embodiment, $L_{11}$ to $L_{13}$ and $L_{21}$ to $L_{23}$ may each independently be a single bond, a methylene group, an ethylene group, a propylene group, a butylene group, a pentylene group, an ethenylene group, a propenylene group, a butenylene group, a butadienylene group, a pentenylene group, a pentadienylene group, an ethynylene group, a propynylene group, a butynylene group, or a methylene group, an ethylene group, a propylene group, a butylene group, a pentylene group, an ethenylene group, a propenylene group, a butenylene group, a butadienylene group, a pentenylene group, a pentadienylene group, an ethynylene group, a propynylene group, or a butynylene group, each substituted with at least one selected from deuterium, —F, —Cl, —Br, —I, a hydroxyl group, a cyano group, a nitro group, an amidino group, a hydrazino group, a hydrazono group, and a $C_1$-$C_{10}$ alkyl group.

In Formula 1, a11 to a13 and a21 to a23 may each independently be 0, 1, 2, 3, 4, or 5.

In an embodiment, a11 to a13 and a21 to a23 may each independently be 0, 1, 2, or 3.

$Z_{11}$ to $Z_{13}$, $Z_{21}$ to $Z_{23}$ and $R_1$ to $R_9$ in Formula 1 may each independently be hydrogen, deuterium, an azide group (—$N_3$), —F, —Cl, —Br, —I, a hydroxyl group, a cyano group, a nitro group, an amidino group, a hydrazino group, a hydrazono group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a $C_1$-$C_{60}$ heteroaryloxy group unsubstituted or substituted with at least one $R_{10a}$, a $C_1$-$C_{60}$ heteroarylthio group unsubstituted or substituted with at least one $R_{10a}$, a monovalent non-aromatic condensed polycyclic group unsubstituted or substituted with at least one $R_{10a}$, a monovalent non-aromatic condensed heteropolycyclic group unsubstituted or substituted with at least one $R_{10a}$, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), or —P(=S)($Q_1$)($Q_2$).

At least one selected from $Z_{11}$ to $Z_{13}$, $Z_{21}$ to $Z_{23}$ and $R_1$ to $R_9$ in Formula 1 may be —$N_3$.

In an embodiment, the heterocyclic compound may include one to five azide groups (—$N_3$). In an embodiment, the heterocyclic compound may include two or three —$N_3$.

In an embodiment, at least one selected from $Z_{11}$ to $Z_{13}$ and $Z_{21}$ to $Z_{23}$ in Formula 1 may be —$N_3$.

In an embodiment, each of $Z_{11}$ to $Z_{13}$ in Formula 1 may be —$N_3$.

In an embodiment, each of $Z_{21}$ to $Z_{23}$ in Formula 1 may be —$N_3$.

In the case where each of $Z_{11}$ to $Z_{13}$ in Formula 1 is —$N_3$, at least one selected from -($L_{21}$)$_{a21}$-$Z_{21}$, -($L_{22}$)$_{a22}$-$Z_{22}$ and -($L_{23}$)$_{a23}$-$Z_{23}$ may be hydrogen.

In an embodiment, the heterocyclic compound may be represented by one selected from Formulae 2A and 2B:

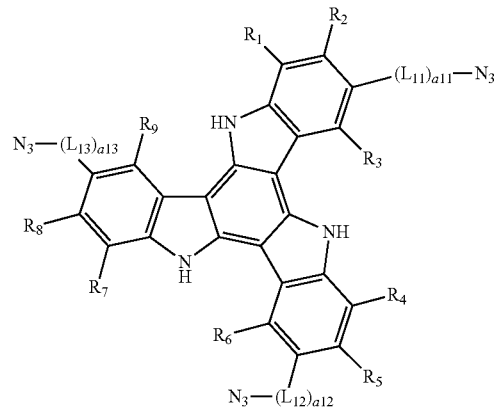

Formula 2A

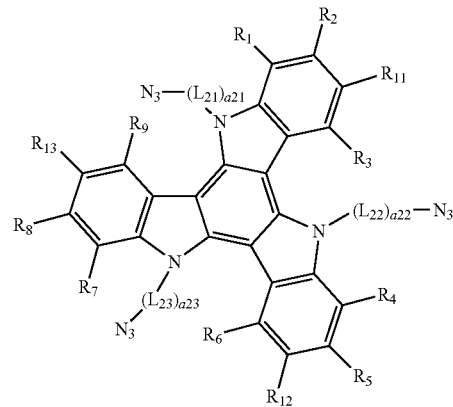

Formula 2B wherein, in Formulae 2A and 2B, $L_{11}$ to $L_{13}$, $L_{21}$ to $L_{23}$, $Z_{11}$ to $Z_{13}$, $Z_{21}$ to $Z_{23}$ and $R_1$ to $R_9$ are the same as described elsewhere in the present specification, $R_{11}$ to $R_{13}$ may each independently be hydrogen, deuterium, —F, —Cl, —Br, —I, a hydroxyl group, a cyano group, a nitro group, an amidino group, a hydrazino group, a hydrazono group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a $C_1$-$C_{60}$ heteroaryloxy group unsubstituted or substituted with at least one $R_{10a}$, a $C_1$-$C_{60}$ heteroarylthio group unsubstituted or substituted with at least one $R_{10a}$, a monovalent non-aromatic condensed polycyclic group unsubstituted or substituted with at least one $R_{10a}$, a monovalent non-aromatic condensed heteropolycyclic group unsubstituted or substituted with at least one $R_{10a}$, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), or —P(=S)($Q_1$)($Q_2$), and $R_{10a}$ is the same as described elsewhere in the present specification.

In an embodiment, $Z_{11}$ to $Z_{13}$, $Z_{21}$ to $Z_{23}$ and $R_1$ to $R_9$ may each independently be: hydrogen, deuterium, —F, —Cl, —Br, —I, a cyano group, a $C_1$-$C_{20}$ alkyl group, or a $C_1$-$C_{20}$ alkoxy group, a $C_1$-$C_{20}$ alkyl group or a $C_1$-$C_{20}$ alkoxy group, each substituted with deuterium, —F, —Cl, —Br, —I, a cyano group, a phenyl group, a biphenyl group or any combination thereof, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, or an indolocarbazolyl group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indeno carbazolyl group, or an indolocarbazolyl group, each substituted with deuterium, —F, —Cl, —Br, —I, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphtho silolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indeno carbazolyl group, an indolocarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)($Q_{31}$), —S(=O)$_2$($Q_{31}$), —P(=O)($Q_{31}$)($Q_{32}$), —P(=S)($Q_{31}$)($Q_{32}$), or any combination thereof; or —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), or —P(=S)($Q_1$)($Q_2$).

In an embodiment, $R_1$ to $R_9$ may each independently be hydrogen, deuterium, —F, —Cl, —Br, —I, a cyano group, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with deuterium, —F, —Cl, —Br, —I, a cyano group, a phenyl group, a biphenyl group, or any combination thereof; or a group represented by one selected from Formulae 5-1 to 5-26 and Formulae 6-1 to 6-55:

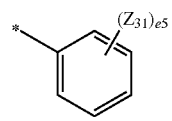

5-1

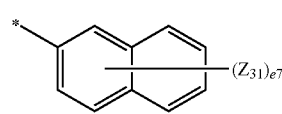

5-2

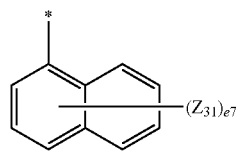

5-3

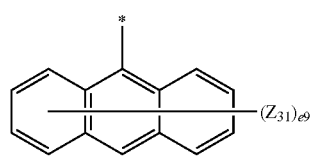

5-4

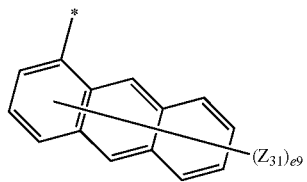

5-5

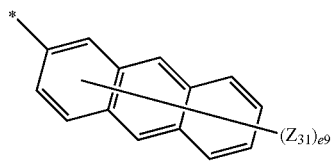

5-6

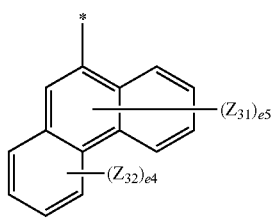

5-7

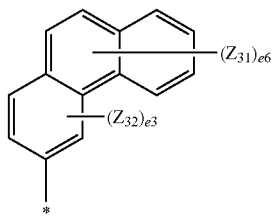

5-8

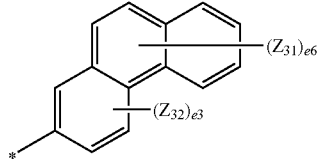

5-9

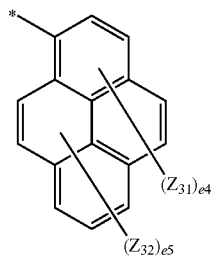

5-10

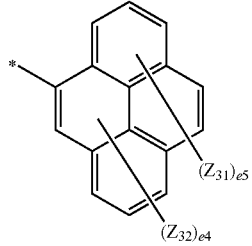

5-11

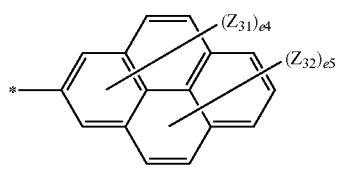
5-12
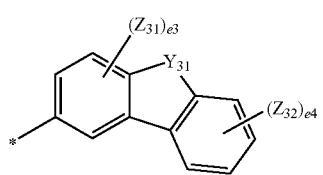
5-13
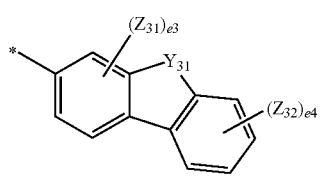
5-14
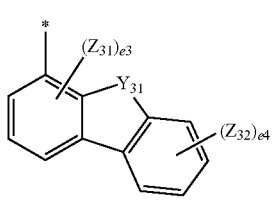
5-15
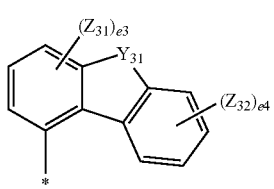
5-16
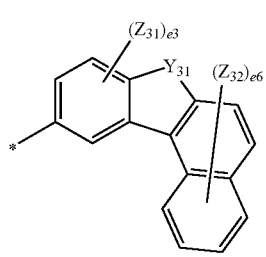
5-17
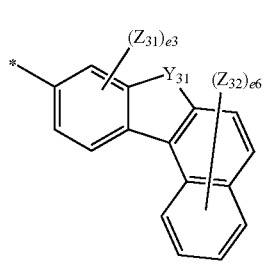
5-18
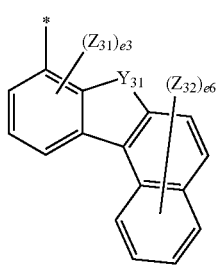
5-19
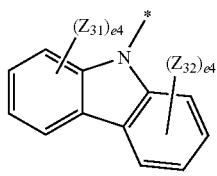
5-20
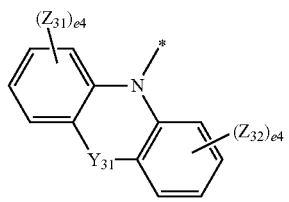
5-21
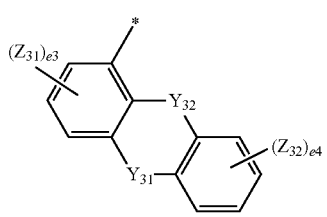
5-22
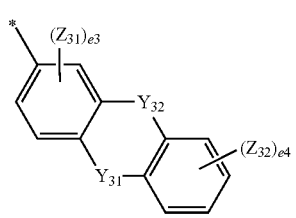
5-23
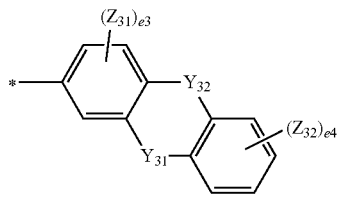
5-24
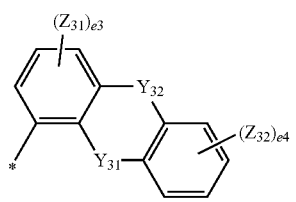
5-25
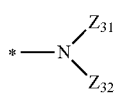
5-26

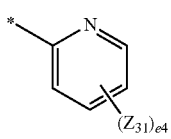
6-1
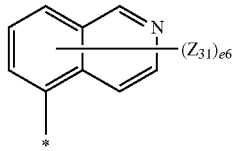
6-11
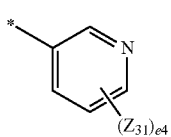
6-2
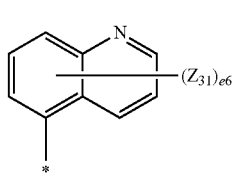
6-12
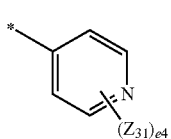
6-3
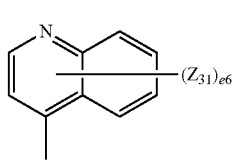
6-13
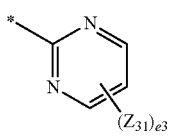
6-4
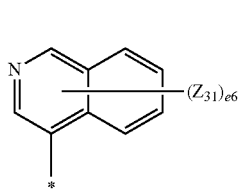
6-14
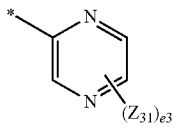
6-5
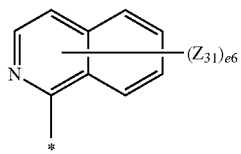
6-15
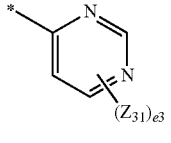
6-6
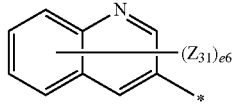
6-16
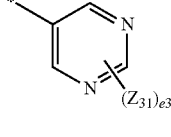
6-7
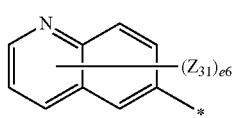
6-17
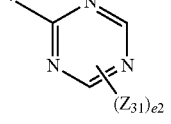
6-8
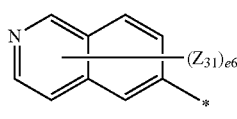
6-18
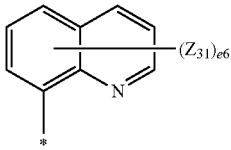
6-9
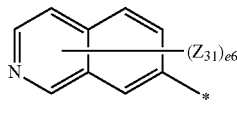
6-19
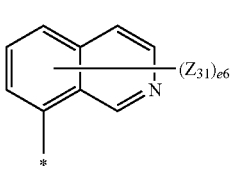
6-10
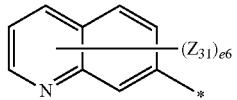
6-20

-continued
6-21 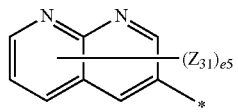
6-22 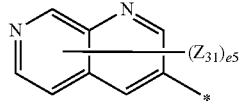
6-23 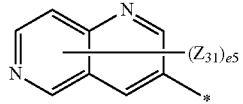
6-24 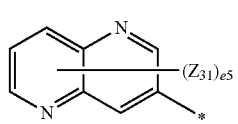
6-25 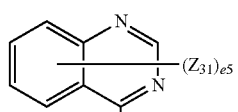
6-26 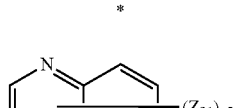
6-27 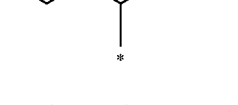
6-28 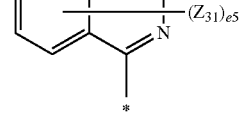
6-29 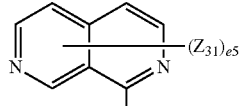
6-30 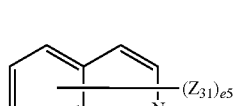
6-31 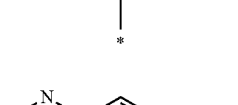
6-32 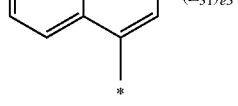
-continued
6-33 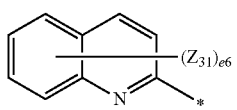
6-34 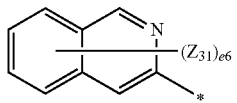
6-35 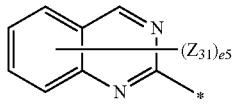
6-36 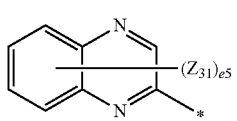
6-37 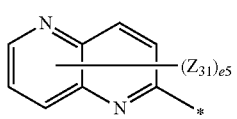
6-38 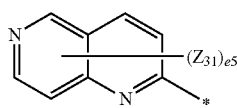
6-39 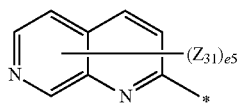
6-40 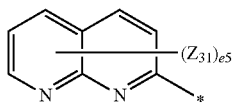
6-41 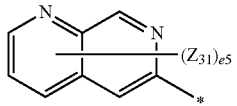
6-42 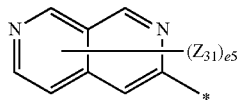

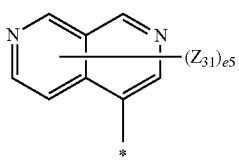
6-43

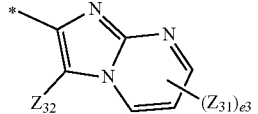
6-52

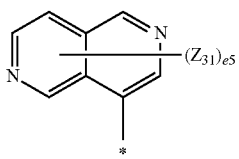
6-44

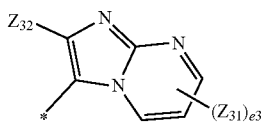
6-53

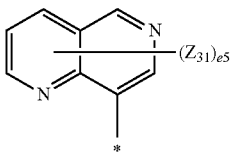
6-45

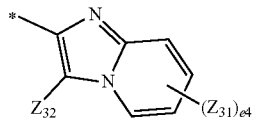
6-54

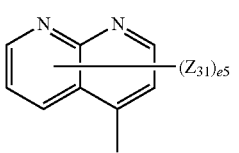
6-46

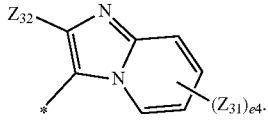
6-55

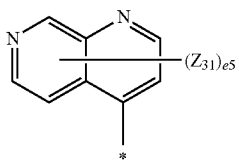
6-47

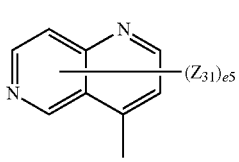
6-48

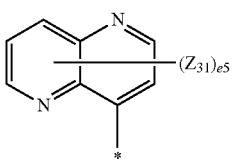
6-49

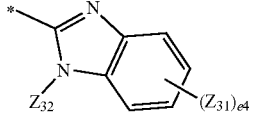
6-50

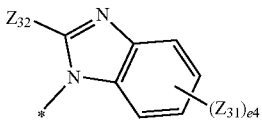
6-51

In Formulae 5-1 to 5-26 and 6-1 to 6-55, $Y_{31}$ and $Y_{32}$ may each independently be O, S, $C(Z_{33})(Z_{34})$, $N(Z_{33})$, or $Si(Z_{33})(Z_{34})$, $Z_{31}$ to $Z_{34}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a biphenyl group, a terphenyl group, a naphthyl group, a fluorenyl group, a spiro-bifluorenyl group, a phenanthrenyl group, an anthracenyl group, a triphenylenyl group, a pyridinyl group, a pyrimidinyl group, a carbazolyl group, and a triazinyl group, e2 may be 1 or 2,
e3 may be an integer from 1 to 3,
e4 may be an integer from 1 to 4,
e5 may be an integer from 1 to 5,
e6 may be an integer from 1 to 6,
e7 may be an integer from 1 to 7,
e9 may be an integer from 1 to 9, and
* indicates a binding site to a neighboring atom.

In an embodiment, $R_1$ to $R_9$ may each independently be hydrogen, deuterium, —F, —Cl, —Br, —I, a cyano group, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with deuterium, —F, —Cl, —Br, —I, a cyano group, a phenyl group, a biphenyl group, or any combination thereof;

a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a carbazolyl group, an acridinyl group, a dibenzofuranyl group, a dibenzothiophenyl group, a benzocarbazolyl group, or a dibenzocarbazolyl group; or a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a carbazolyl group, an acridinyl group, a dibenzofuranyl group, a dibenzothiophenyl group, a benzocarbazolyl group, or a dibenzocarbazolyl group, each substituted with deuterium, —F, —Cl, —Br, —I, a cyano group, a $C_1$-$C_{20}$ alkyl group, a $C_1$-$C_{20}$ alkoxy group, a phenyl group, a biphenyl group, or any combination thereof.

In an embodiment, $Z_{11}$ to $Z_{13}$, $Z_{21}$ to $Z_{23}$, and $R_1$ to $R_9$ may each independently be hydrogen, deuterium, —F, —Cl, —Br, —I, a cyano group, a $C_1$-$C_{20}$ alkyl group, or a $C_1$-$C_{20}$ alkoxy group;

a $C_1$-$C_{20}$ alkyl group and a $C_1$-$C_{20}$ alkoxy group, each substituted with deuterium, —F, —Cl, —Br, —I, a cyano group, a phenyl group, a biphenyl group, or any combination thereof;

a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a carbazolyl group, an acridinyl group, a dibenzofuranyl group, a dibenzothiophenyl group, a benzocarbazolyl group, or a dibenzocarbazolyl group; or a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a carbazolyl group, an acridinyl group, a dibenzofuranyl group, a dibenzothiophenyl group, a benzocarbazolyl group, or a dibenzocarbazolyl group, each substituted with deuterium, —F, —Cl, —Br, —I, a cyano group, a $C_1$-$C_{20}$ alkyl group, a $C_1$-$C_{20}$ alkoxy group, a phenyl group, a biphenyl group, or any combination thereof.

In an embodiment, the heterocyclic compound may be represented by one selected from Formulae 3A-1 to 3A-3, 3B-1, and 3B-2:

Compound 3A-1

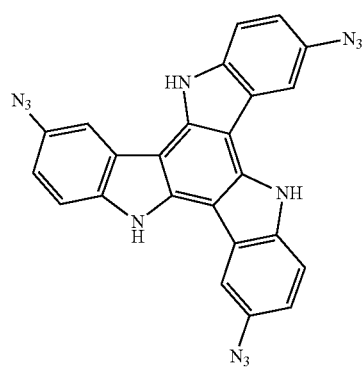

Formula 3A-2

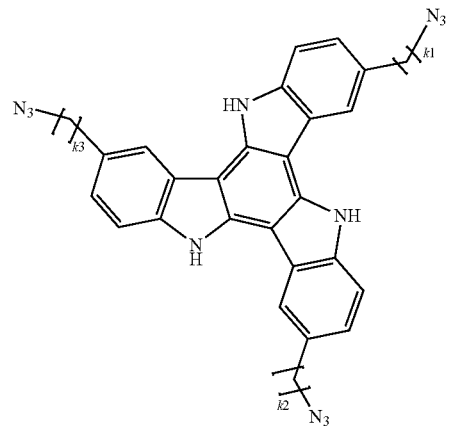

Formula 3A-3

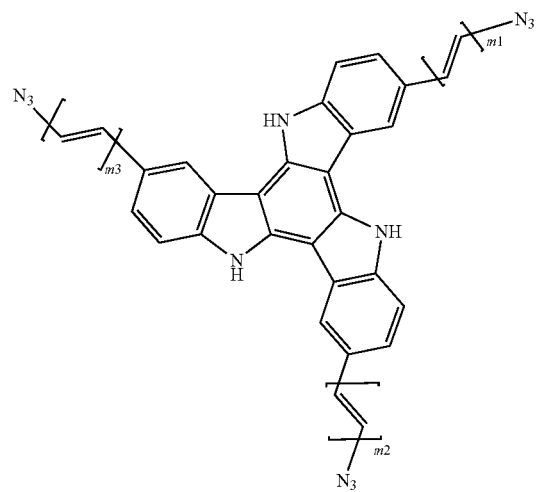

Formula 3B-1

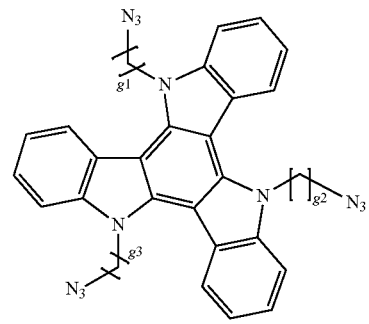

Formula 3B-2

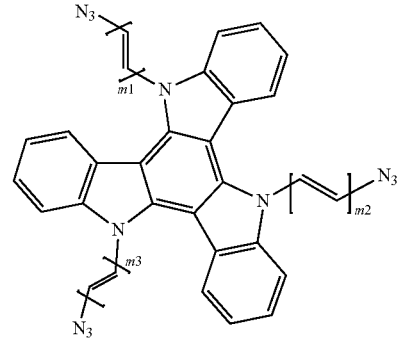

In Formulae 3A-1 to 3A-3, 3B-1, and 3B-2,
k1, k2, and k3 may each be 0, 1, 2, 3, 4, 5, 6, 7, 8, 9, or 10,
g1, g2, and g3 may each be 4, 5, 6, 7, 8, 9, or 10, and
m1, m2, and m3 may each be 1, 2, 3, 4, or 5.
In an embodiment, the heterocyclic compound represented by Formula 1 may be one selected from Compounds 1 to 7:
Compound 1
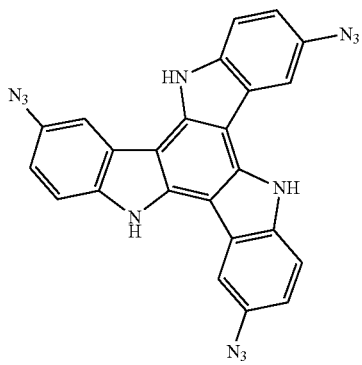
Compound 2
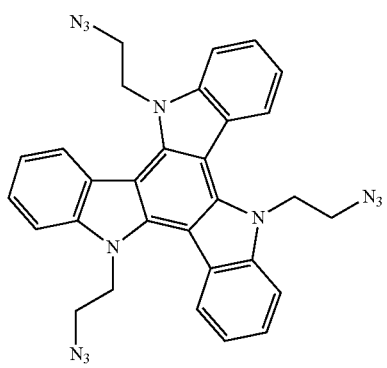
Compound 3
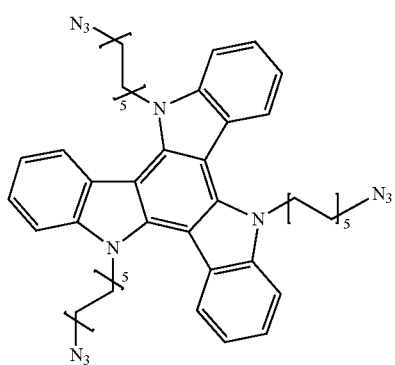
-continued
Compound 4
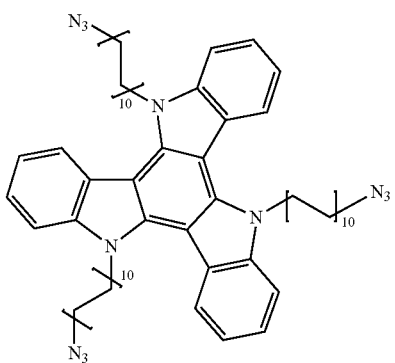
Compound 5
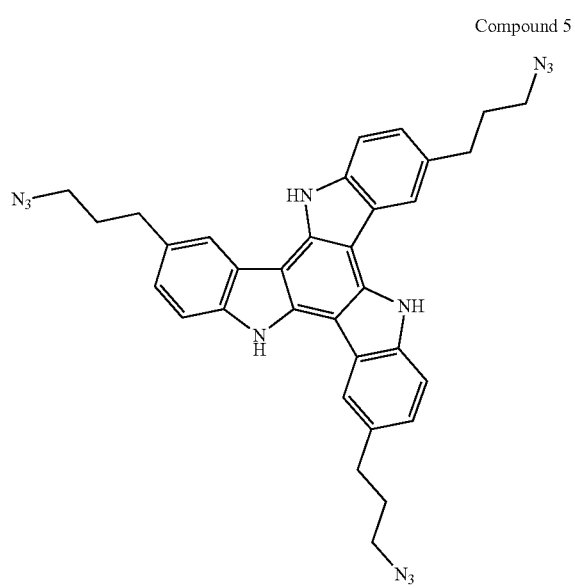
Compound 6
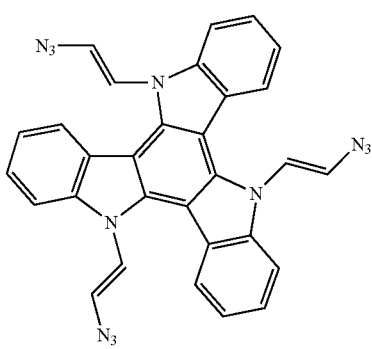

-continued

Compound 7

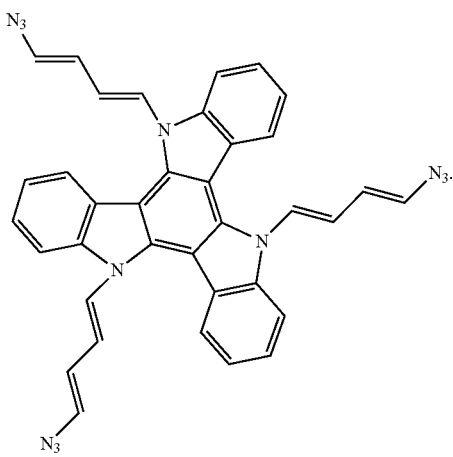

Embodiments of the heterocyclic compound are capable of thermal crosslinking and photocrosslinking due to the inclusion of an azide group therein. Accordingly, the heterocyclic compound may form a film by a crosslinking reaction without using a separate crosslinking agent, and thereby, exhibit excellent hole transport characteristics and structural stability.

Therefore, an electronic device, for example, a light-emitting device, using the heterocyclic compound represented by Formula 1 may have a low driving voltage, high efficiency, and a long lifespan. In addition, when an interlayer of a light-emitting device is formed according to a solution process using the composition containing the heterocyclic compound, the deteriorative deformation of the molecular arrangement caused by the driving of the light-emitting device may be prevented or reduced, and thus, a light-emitting device having excellent hole mobility and lifespan characteristics may be obtained.

Methods of synthesizing the heterocyclic compound represented by Formula 1 may be readily recognized by those of ordinary skill in the art by referring to Examples described herein.

Composition

Another aspect of an embodiment of the present disclosure provides a hole transport composition including the heterocyclic compound.

In an embodiment, the hole transport composition may further include a solvent.

In an embodiment, the solvent may include a $C_6$-$C_{20}$ aliphatic hydrocarbon, a $C_5$-$C_{20}$ aromatic hydrocarbon, chloroform, methylene chloride, methyl benzoate, ethyl acetate, ethylene glycol, diethylene glycol, or any combination thereof.

In an embodiment, the solvent may be represented by Formula 8 below:

Formula 8

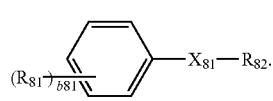

In Formula 8,
$X_{81}$ may be a single bond, —O—, —S—, —C(=O)—, —C(=O)O—, or —C(=O)NH—, $R_{81}$ and $R_{82}$ may each independently be hydrogen, deuterium, —F, —Cl, —Br, —I, a hydroxyl group, a cyano group, a nitro group, an amidino group, a hydrazino group, a hydrazono group, $Si(Q_{31})(Q_{32})(Q_{33})$, a $C_1$-$C_{10}$ alkyl group, a $C_1$-$C_{10}$ alkoxy group, a phenyl group, a biphenyl group, a terphenyl group, a naphthyl group, a fluorenyl group, a spiro-bifluorenyl group, a benzofluorenyl group, a phenanthrenyl group, a pyrenyl group, a carbazolyl group, a dibenzofuranyl group, a benzonaphthofuranyl group, a dibenzothiophenyl group, a benzocarbazolyl group, or a dibenzocarbazolyl group; or a $C_1$-$C_{10}$ alkyl group, a $C_1$-$C_{10}$ alkoxy group, a phenyl group, a biphenyl group, a terphenyl group, a naphthyl group, a fluorenyl group, a spiro-bifluorenyl group, a benzofluorenyl group, a phenanthrenyl group, a pyrenyl group, a carbazolyl group, a dibenzofuranyl group, a benzonaphthofuranyl group, a dibenzothiophenyl group, a benzocarbazolyl group, or a dibenzocarbazolyl group, each substituted with deuterium, —F, —Cl, —Br, —I, a hydroxyl group, a cyano group, a nitro group, an amidino group, a hydrazino group, a hydrazono group, $Si(Q_{81})(Q_{82})(Q_{83})$, a methyl group, an ethyl group, a propyl group, an isobutyl group, a sec-butyl group, ter-butyl group, pentyl group, an iso-amyl group, a hexyl group, a $C_1$-$C_{10}$ alkoxy group, a phenyl group, a biphenyl group, a terphenyl group, a naphthyl group, a fluorenyl group, a spiro-bifluorenyl group, a benzofluorenyl group, a phenanthrenyl group, a pyrenyl group, a carbazolyl group, a carbazolyl group substituted with a phenyl group, a dibenzofuranyl group, a benzonaphthofuranyl group, a dibenzothiophenyl group, a benzocarbazolyl group, a dibenzocarbazolyl group, or any combination thereof, $b_{81}$ may each independently be 1, 2, 3, 4, or 5, and $Q_{81}$ to $Q_{83}$ may each independently be hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_3$-$C_{10}$ cycloalkyl group, a $C_1$-$C_{10}$ heterocycloalkyl group, a $C_6$-$C_{60}$ aryl group, a $C_6$-$C_{60}$ aryl group substituted with a $C_1$-$C_{60}$ alkyl group, a $C_1$-$C_{60}$ heteroaryl group, a monovalent non-aromatic condensed polycyclic group, a monovalent non-aromatic condensed heteropolycyclic group, a biphenyl group, or a terphenyl group.

In an embodiment, the solvent may be a $C_5$-$C_{20}$ aromatic hydrocarbon, for example, anisole.

In an embodiment, the hole transport composition may include the heterocyclic group and the solvent, and the amount of the heterocyclic group per may be from 0.01 parts by weight to 50 parts by weight based on 100 parts by weight of the hole transport composition. In an embodiment, the amount of the heterocyclic group may be from 0.05 parts by weight to 20 parts by weight, from 0.1 parts by weight to 10 parts by weight, or from 0.5 parts by weight to 5, based on 100 parts by weight of the hole transport composition. When the amount ranges are satisfied, the hole transport composition may exhibit physical properties suitable for use in a solution process using, for example, inkjet (e.g., inkjet printing).

Light-Emitting Device

According to another aspect of embodiment, provided is a light-emitting device including: a first electrode; a second electrode facing the first electrode; an interlayer which is between the first electrode and the second electrode and includes the emission layer; and the light-emitting device may include the heterocyclic compound, a polymer containing a repeating unit derived from the heterocyclic compound, or any combination thereof.

In an embodiment, the repeating unit derived from the heterocyclic compound may be represented by one selected from Formulae 1-1 to 1-4:

Formula 1-1

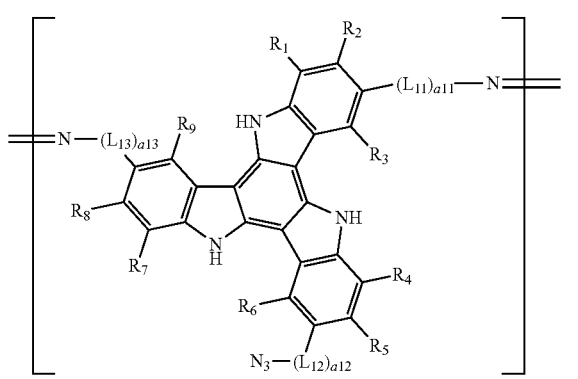

Formula 1-2

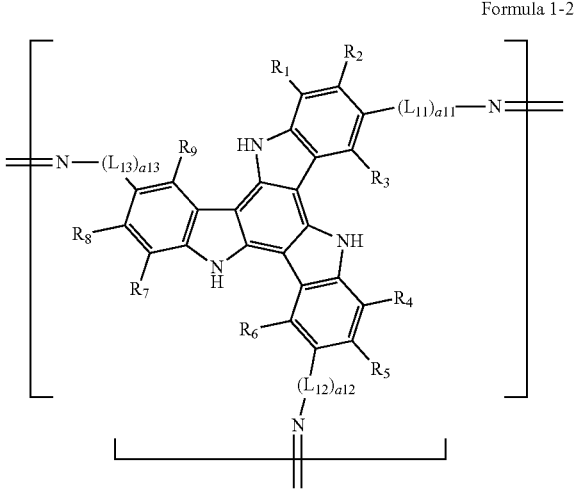

Formula 1-3

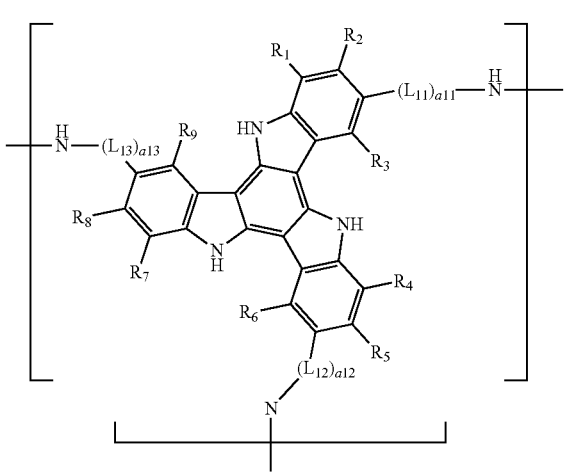

Formula 1-4

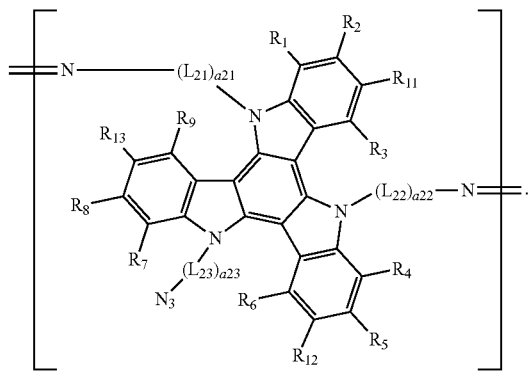

In Formulae 1-1 to 1-4
$L_{11}$ to $L_{13}$, $L_{21}$ to $L_{23}$, $R_1$ to $R_9$, and $R_{11}$ to $R_{13}$ are the same as described elsewhere in the present specification.

In an embodiment, the first electrode of the light-emitting device is an anode, the second electrode of the light-emitting device is a cathode, and
the interlayer includes the hole transport region between the first electrode and the emission layer, and the hole transport region may include the heterocyclic compound, the polymer or any combination thereof.

In an embodiment, the hole transport region may include a hole injection layer, a hole transport layer, a buffer layer, an emission auxiliary layer, an electron blocking layer, or any combination thereof.

For example, the hole transport region may include a hole injection layer, a hole transport layer, a buffer layer, an emission auxiliary layer, an electron blocking layer, or any combination thereof, and
the hole injection layer, the hole transport layer, the buffer layer, the emission auxiliary layer, the electron blocking layer, or any combination thereof may include the heterocyclic compound, the polymer, or any combination thereof.

In an embodiment, the emission layer of the light-emitting device includes a host and a dopant, and the host or the dopant may include the heterocyclic compound, the polymer, or any combination thereof.

In an embodiment, the light-emitting device may further include an electron transport region between the emission layer and the second electrode, and
the electron transport region may include at least one selected from a hole blocking layer, an electron transport layer, and an electron injection layer.

In an embodiment, the light-emitting device may further include at least one selected from a first capping layer outside the first electrode and a second capping layer outside the second electrode, and the heterocyclic compound represented by Formula 1 may be included in at least one selected from the first capping layer and the second capping layer. Additional details for the first capping layer and/or second capping layer are the same as described elsewhere in the present specification.

In one or more embodiments, the light-emitting device may further include:
a first capping layer outside the first electrode and containing the heterocyclic compound represented by Formula 1;

a second capping layer outside the second electrode and containing the heterocyclic compound represented by Formula 1; or the first capping layer and the second capping layer.

The expression "(an interlayer and/or a capping layer) includes at least one heterocyclic compound," as used herein, may include a case in which "(an interlayer and/or a capping layer) includes identical heterocyclic compounds represented by Formula 1" and a case in which "(an organic layer) includes two or more different heterocyclic compounds represented by Formula 1."

For example, the interlayer and/or capping layer may include Compound 1 only as the heterocyclic compound. In this regard, Compound 1 may exist in the emission layer of the light-emitting device. In one or more embodiments, the interlayer may include, as the heterocyclic compound, Compound 1 and Compound 2. In this regard, Compound 1 and Compound 2 may exist in an identical layer (for example, Compound 1 and Compound 2 may all exist in a hole transport region), or different layers (for example, Compound 1 may exist in a hole transport region and Compound 2 may exist in an emission layer).

The term "interlayer," as used herein, refers to a single layer and/or all layers between a first electrode and a second electrode of a light-emitting device.

Another aspect of an embodiment provides an electronic apparatus including the light-emitting device. The electronic apparatus may further include a thin-film transistor. In one or more embodiments, the electronic apparatus may further include a thin-film transistor including a source electrode and a drain electrode, and the first electrode of the light-emitting device may be electrically coupled to the source electrode or the drain electrode. In an embodiment, the electronic apparatus may further include a color filter, a color conversion layer, a touch screen layer, a polarizing layer, or any combination thereof. Additional details of the electronic apparatus are the same as described elsewhere in the present specification.

Description of FIG. 1

FIG. 1 is a schematic cross-sectional view of a light-emitting device 10 according to an embodiment. The light-emitting device 10 includes a first electrode 110, an interlayer 130, and a second electrode 150.

Hereinafter, the structure of the light-emitting device 10 according to an embodiment and a method of manufacturing the light-emitting device 10 will be described in connection with FIG. 1.

First Electrode 110

In FIG. 1, a substrate may be additionally under the first electrode 110 and/or above the second electrode 150. As the substrate, a glass substrate and/or a plastic substrate may be used. In an embodiment, the substrate may be a flexible substrate, and may include plastics having excellent heat resistance and durability, such as polyimide, polyethylene terephthalate (PET), polycarbonate, polyethylene naphthalate, polyarylate (PAR), polyetherimide, or any combination thereof.

The first electrode 110 may be formed by, for example, depositing and/or sputtering a material for forming the first electrode 110 on the substrate. When the first electrode 110 is an anode, a material for forming the first electrode 100 may be a high work function material that facilitates injection of holes.

The first electrode 110 may be a reflective electrode, a semi-transmissive electrode, or a transmissive electrode. When the first electrode 110 is a transmissive electrode, a material for forming the first electrode 110 may include indium tin oxide (ITO), indium zinc oxide (IZO), tin oxide ($SnO_2$), zinc oxide (ZnO), or any combinations thereof. In one or more embodiments, when the first electrode 110 is a semi-transmissive electrode or a reflective electrode, magnesium (Mg), silver (Ag), aluminum (Al), aluminum-lithium (Al—Li), calcium (Ca), magnesium-indium (Mg—In), magnesium-silver (Mg—Ag), or any combinations thereof may be used as a material for forming a first electrode.

The first electrode 110 may have a single layer including (e.g., consisting of) a single-layered structure or a multilayer structure including a plurality of layers. For example, the first electrode 110 may have a three-layered structure of ITO/Ag/ITO.

Interlayer 130

The interlayer 130 may be on the first electrode 110. The interlayer 130 may include an emission layer.

The interlayer 130 may further include a hole transport region placed between the first electrode 110 and the emission layer and an electron transport region placed between the emission layer and the second electrode 150.

The interlayer 130 may further include metal-containing compounds such as organometallic compounds, inorganic materials such as quantum dots, and/or the like, in addition to various suitable organic materials.

In one or more embodiments, the interlayer 130 may include, i) two or more emitting units sequentially stacked between the first electrode 110 and the second electrode 150 and ii) a charge generation layer between the two emitting units. When the interlayer 130 includes the emitting unit and the charge generation layer as described above, the light-emitting device 10 may be a tandem light-emitting device.

Hole Transport Region in Interlayer 130

The hole transport region may have: i) a single-layered structure including (e.g., consisting of) a single layer including (e.g., consisting of) a single material, ii) a single-layered structure including (e.g., consisting of) a single layer including (e.g., consisting of) a plurality of different materials, or iii) a multi-layered structure including a plurality of layers including different materials.

The hole transport region may include a hole injection layer (HIL), a hole transport layer (HTL), an emission auxiliary layer, an electron blocking layer (EBL), or any combination thereof.

For example, the hole transport region may have a multi-layered structure including a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein, in each structure, layers are stacked sequentially from the first electrode 110.

The hole transport region may include the heterocyclic compound, a polymer containing a repeating unit derived from the heterocyclic compound, or any combination thereof.

The hole transport region may further include a compound represented by Formula 201, a compound represented by Formula 202, or any combination thereof:

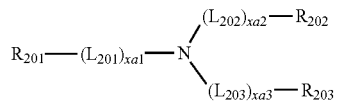

Formula 201

Formula 202

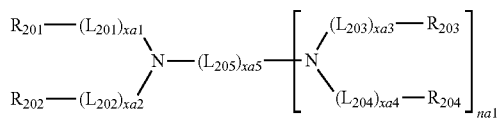 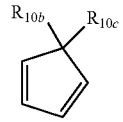

In Formulae 201 and 202, $L_{201}$ to $L_{204}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ may be *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 may each independently an integer from 0 to 5, xa5 may be an integer from 1 to 10, $R_{201}$ to $R_{204}$ and $Q_{201}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ may optionally be linked to each other, via a single bond, to form a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group (for example, a carbazole group and/or the like) unsubstituted or substituted with at least one $R_{10a}$ (see Compound HT16 and/or the like), $R_{203}$ and $R_{204}$ may optionally be linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$, and na1 is an integer from 1 to 4.

In one or more embodiments, each of Formulae 201 and 202 may include at least one selected from groups represented by Formulae CY201 to CY217.

CY201

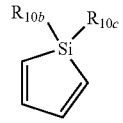

CY202

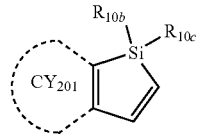

CY203

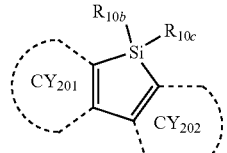

CY204

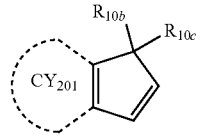

CY205

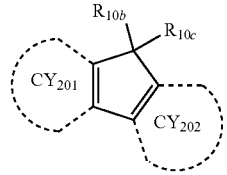

CY206

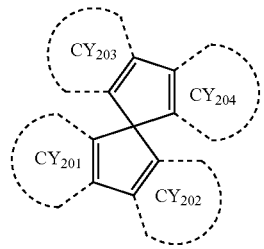

CY207

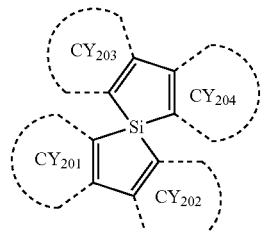

CY208

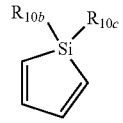

CY209

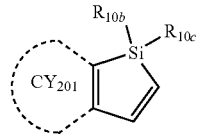

CY210

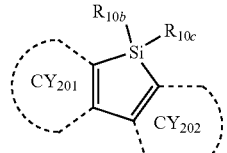

CY211

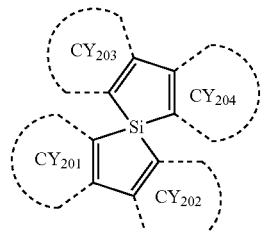

CY212

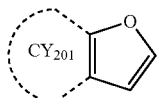

CY213

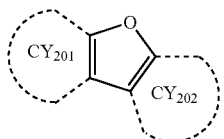

CY214

CY215

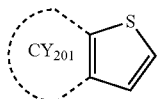

CY216

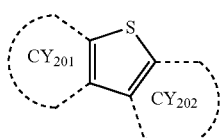

CY217

$R_{10b}$ and $R_{10c}$ in Formulae CY201 to CY217 are the same as described in connection with $R_{10a}$, and ring $CY_{201}$ to ring $CY_{204}$ may each independently be a $C_3$-$C_{20}$ carbocyclic group or a $C_1$-$C_{20}$ heterocyclic group, and at least one hydrogen in Formulae CY201 to CY217 may be unsubstituted or substituted with at least one $R_{10a}$.

In an embodiment, ring $CY_{201}$ to ring $CY_{204}$ in Formulae CY201 to CY217 may each independently be a benzene group, a naphthalene group, a phenanthrene group, or an anthracene group.

In one or more embodiments, each of Formulae 201 and 202 may include at least one selected from groups represented by Formulae CY201 to CY203.

In one or more embodiments, Formula 201 may include at least one selected from groups represented by Formulae CY201 to CY203 and at least one selected from groups represented by Formulae CY204 to CY217.

In one or more embodiments, xa1 in Formula 201 is 1, $R_{201}$ is a group represented by one selected from Formulae CY201 to CY203, xa2 may be 0, and $R_{202}$ may be a group represented by one selected from Formulae CY204 to CY207.

In one or more embodiments, each of Formulae 201 and 202 may not include a group represented by one selected from Formulae CY201 to CY203.

In one or more embodiments, each of Formulae 201 and 202 may not include a group represented by one selected from Formulae CY201 to CY203, and may include at least one selected from groups represented by Formulae CY204 to CY217.

In an embodiment, each of Formulae 201 and 202 may not include a group represented by one selected from Formulae CY201 to CY217.

In an embodiment, the hole transport region may further include one selected from Compounds HT1 to HT44, m-MTDATA, TDATA, 2-TNATA, NPB(NPD), β-NPB, TPD, Spiro-TPD, Spiro-NPB, methylated-NPB, TAPC, HMTPD, 4,4',4''-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), or any combination thereof:

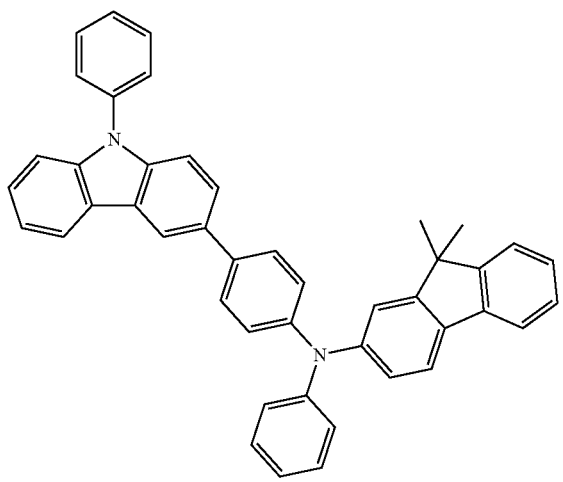

HT1

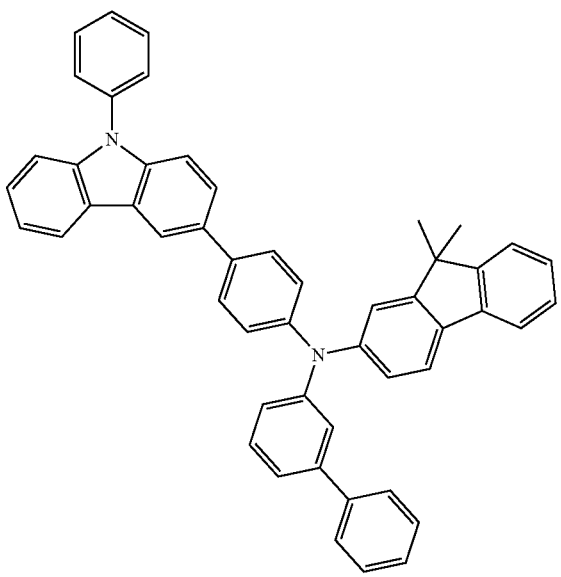

HT2

-continued
HT3 HT4
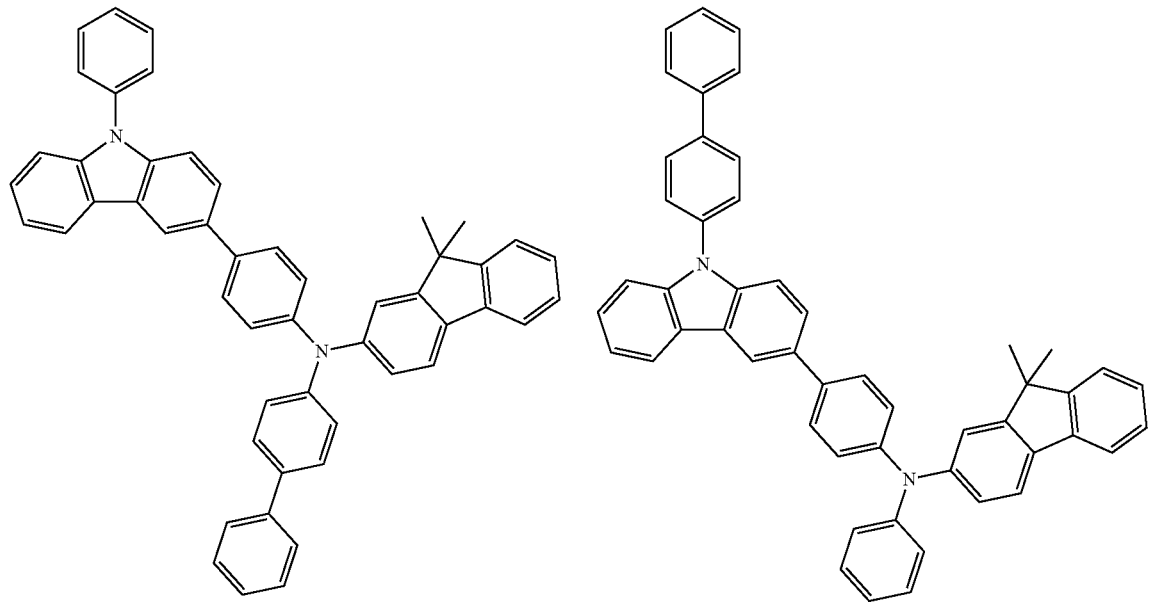
HT5 HT6
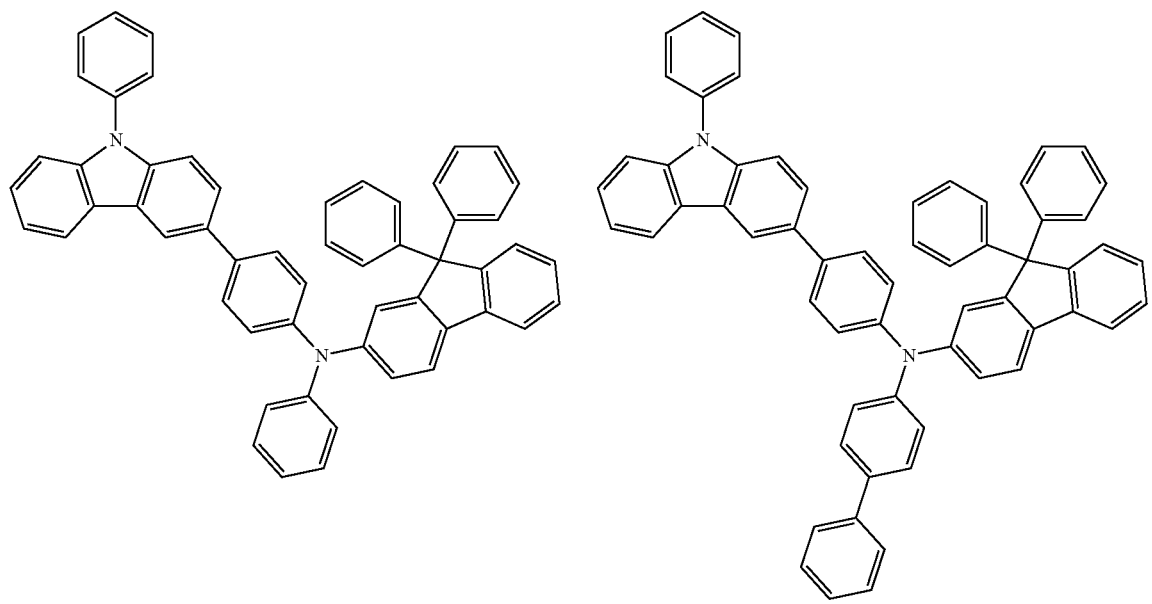

HT7
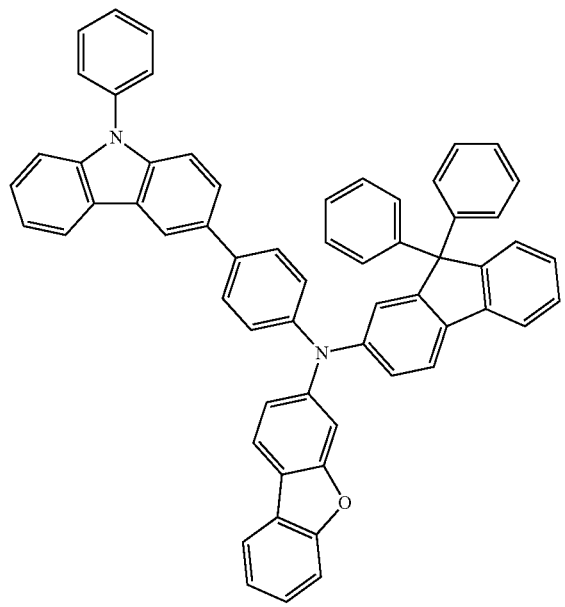
HT8
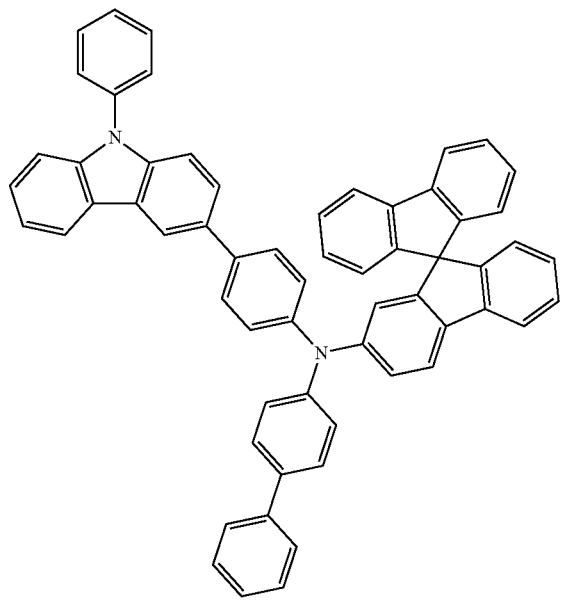
HT9
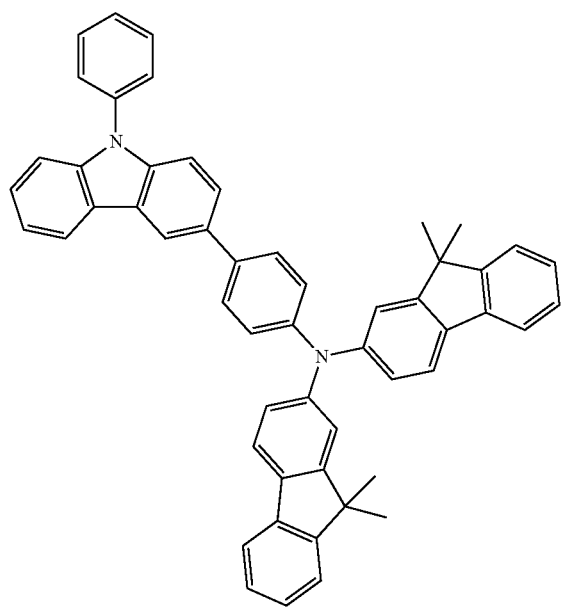
HT10
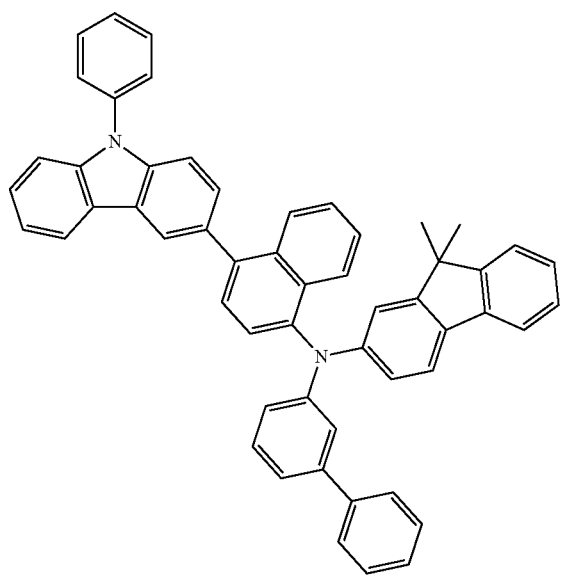

-continued
HT11
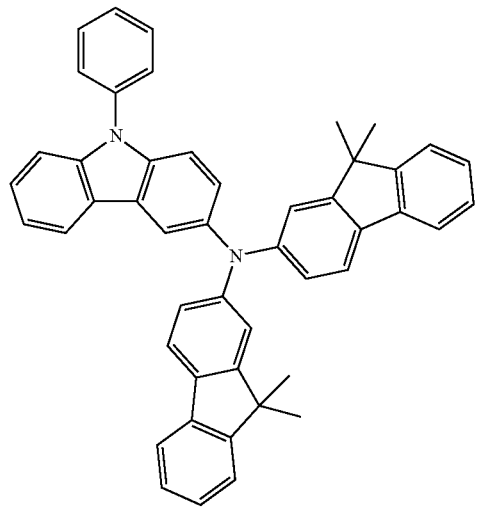
HT12
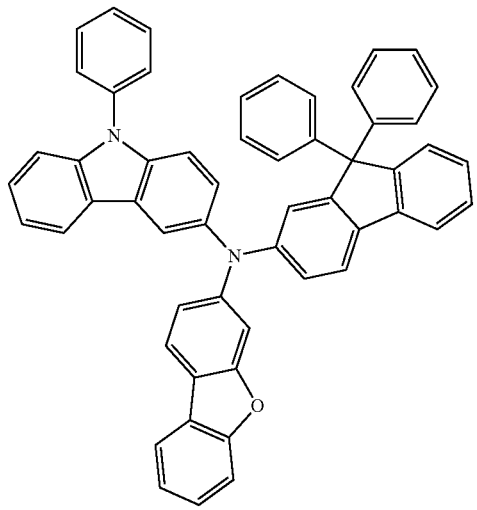
HT13
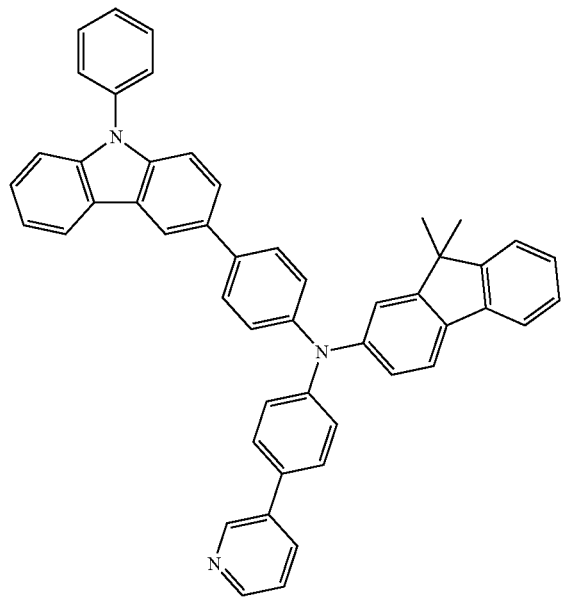
HT14
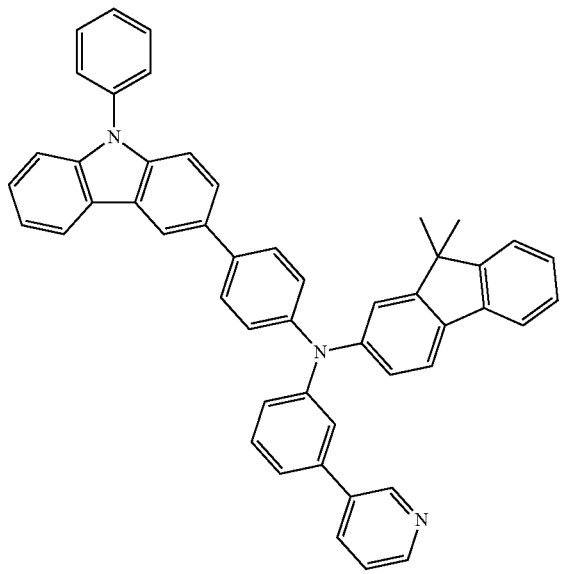
HT15
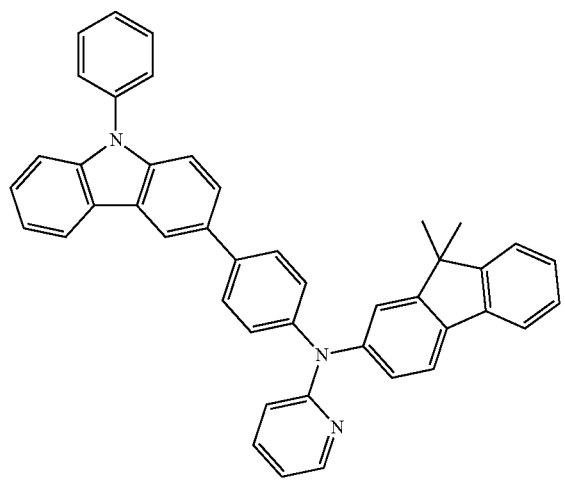
HT16
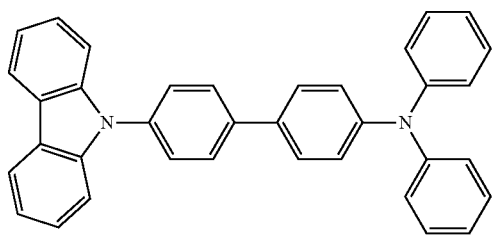

-continued
HT17
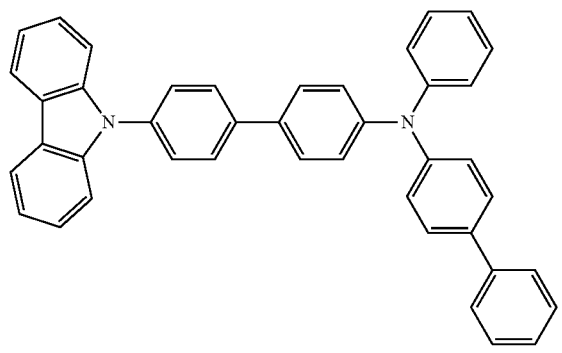
HT18
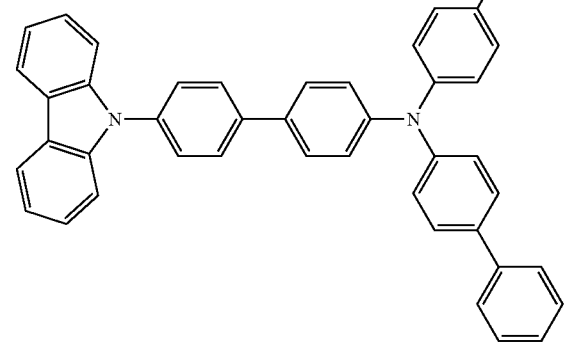
HT19
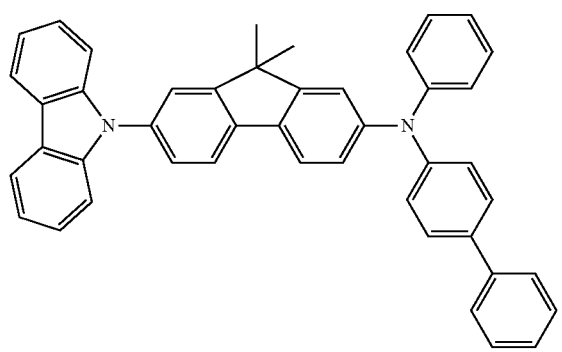
HT20
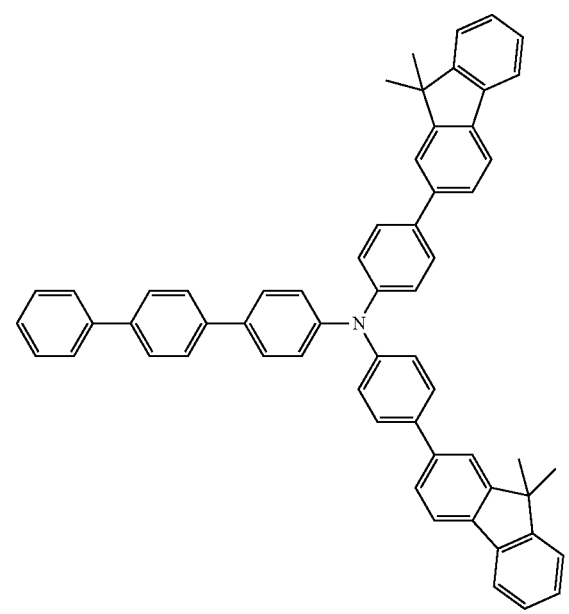

-continued
HT21
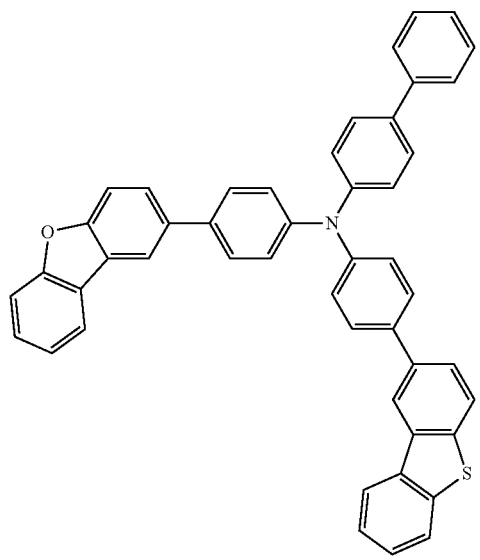
HT22
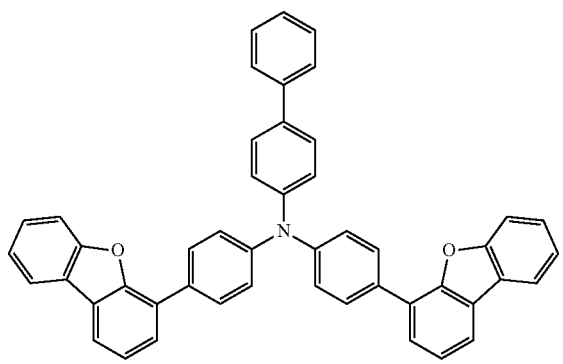
HT23
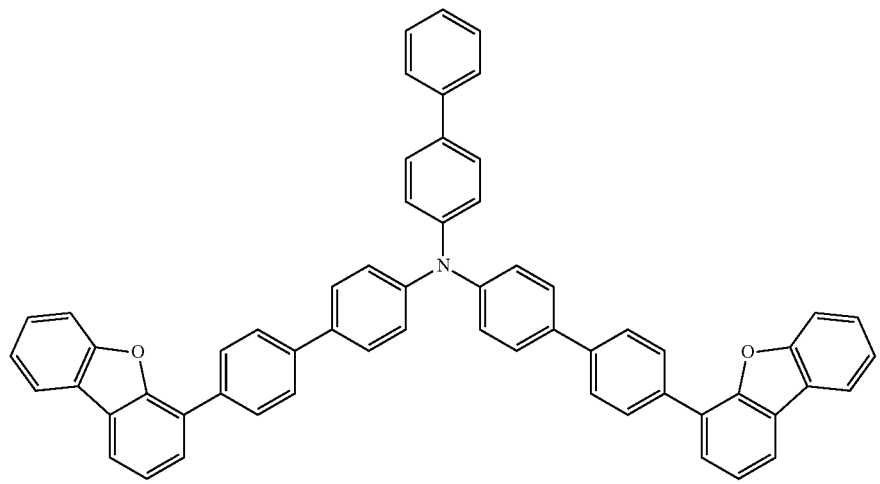
HT24
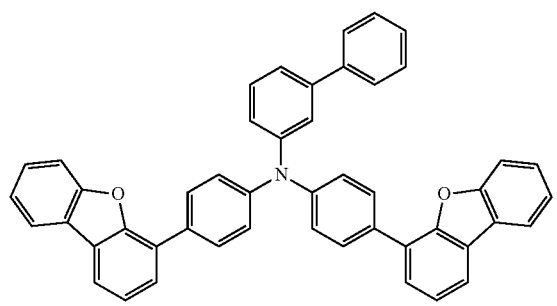
HT25
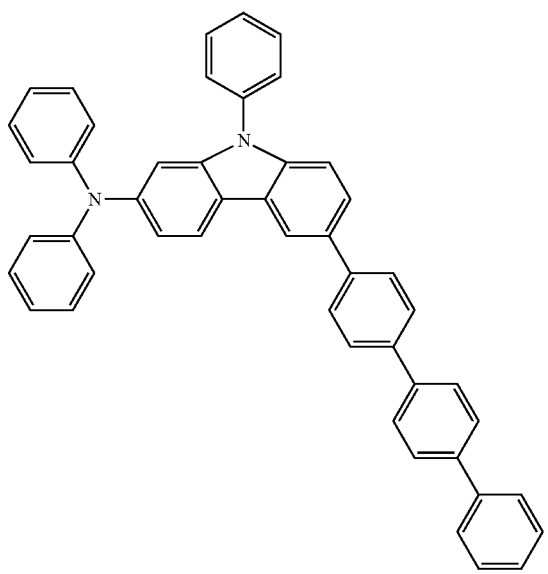

-continued
HT26
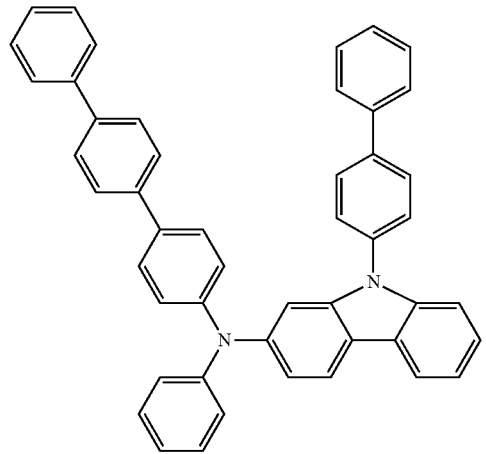
HT27
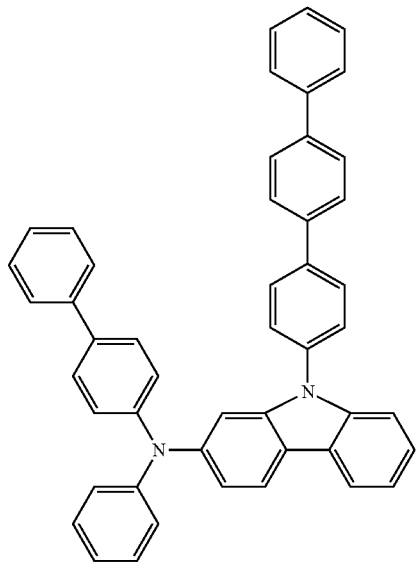
HT28
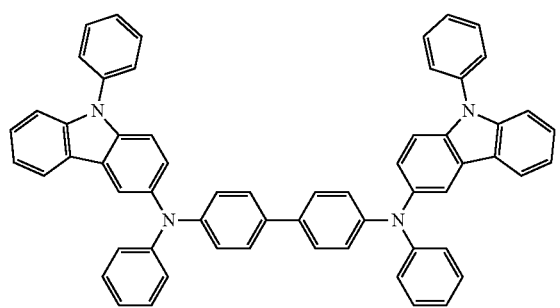
HT29
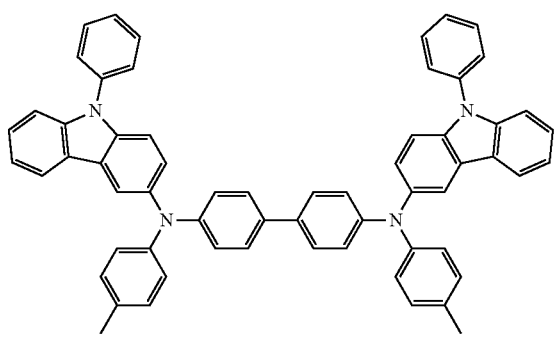
HT30
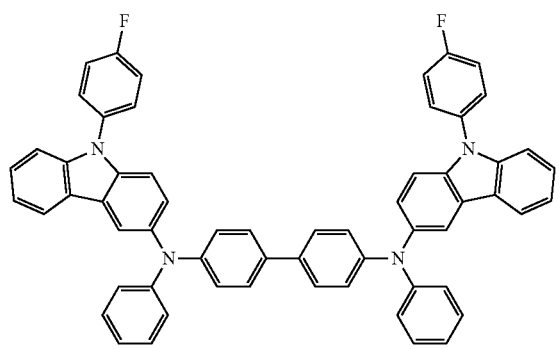
HT31
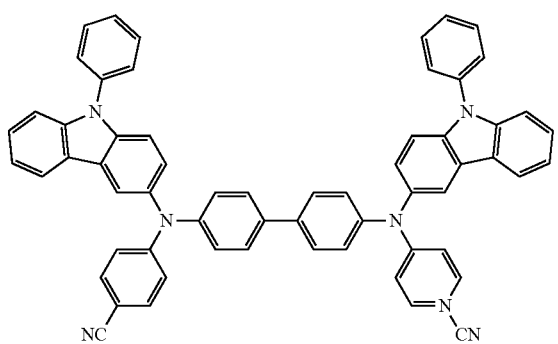

-continued
HT32
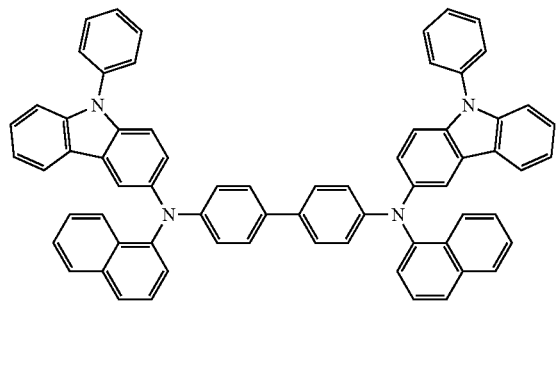
HT33
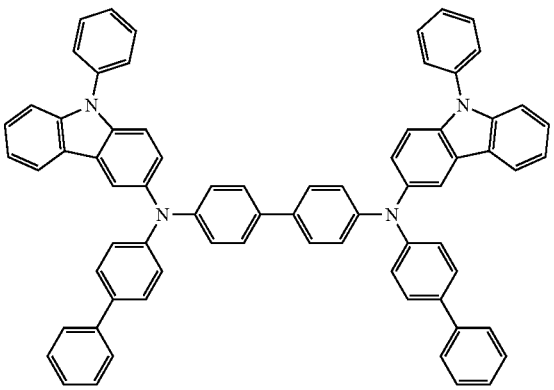
HT34
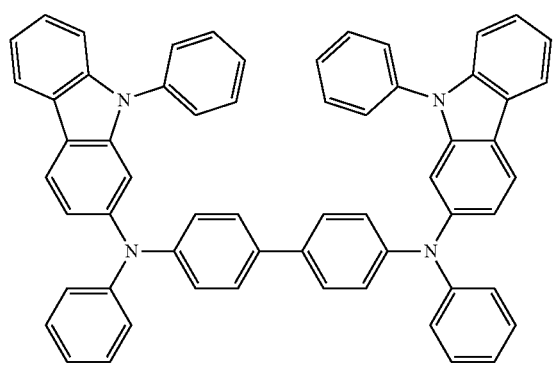
HT35
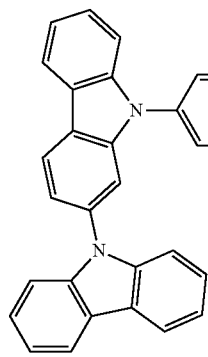
HT36
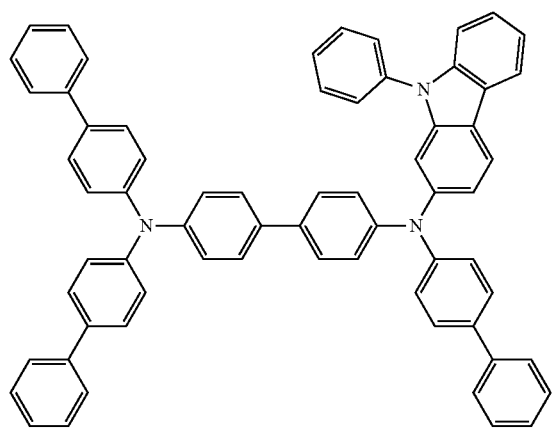
HT37
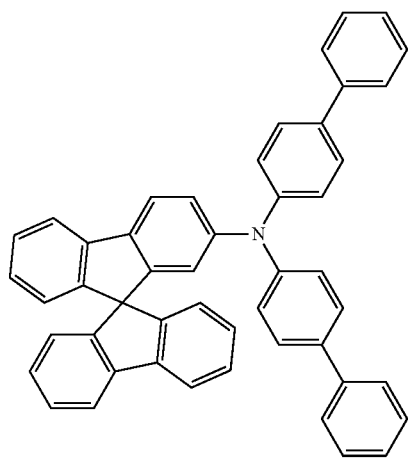

-continued
HT38
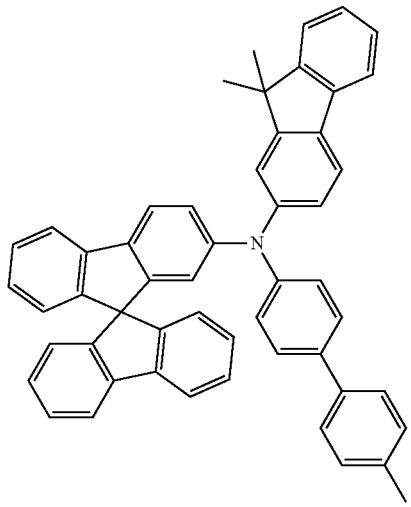
HT39
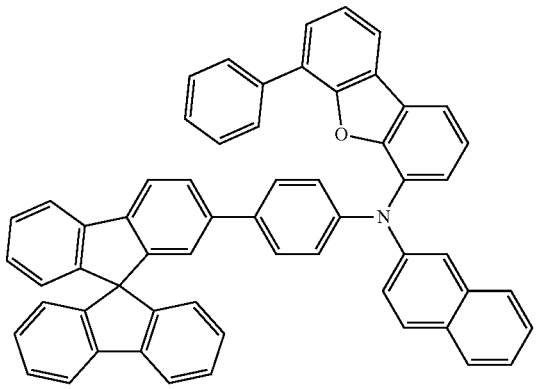
HT40
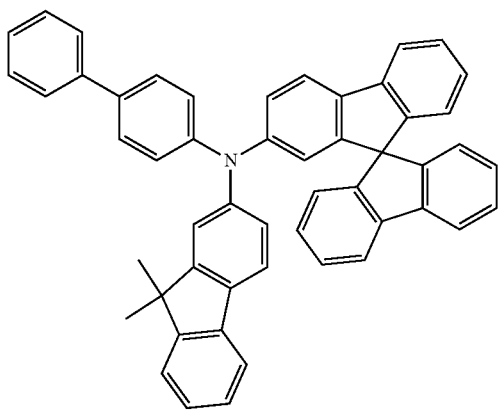
HT41
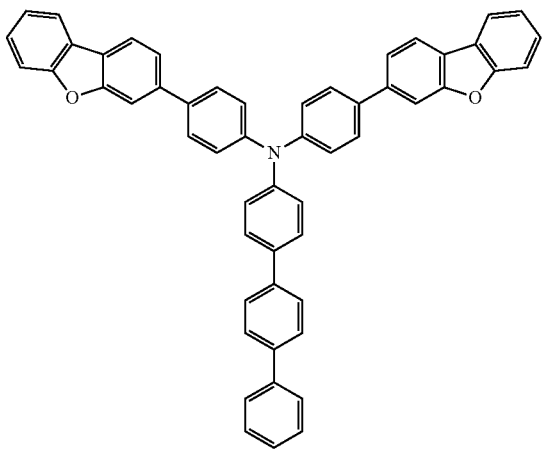
HT42
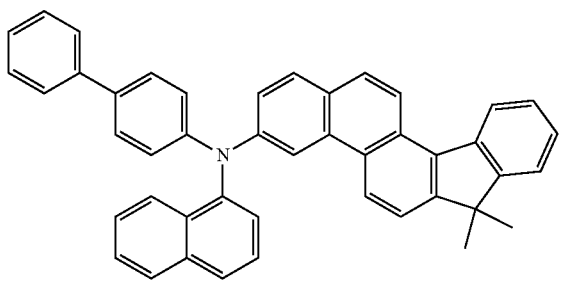
HT43
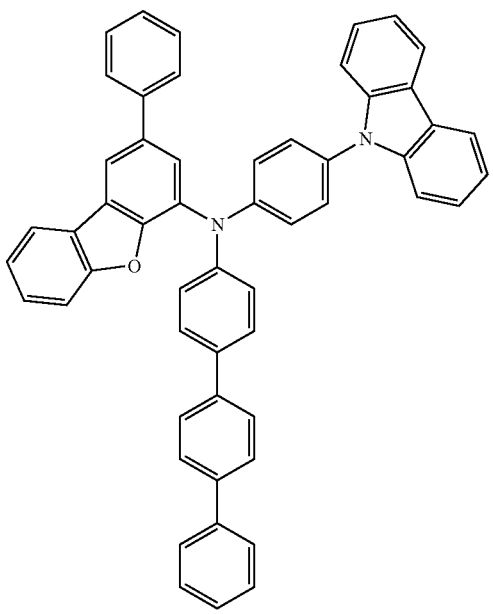

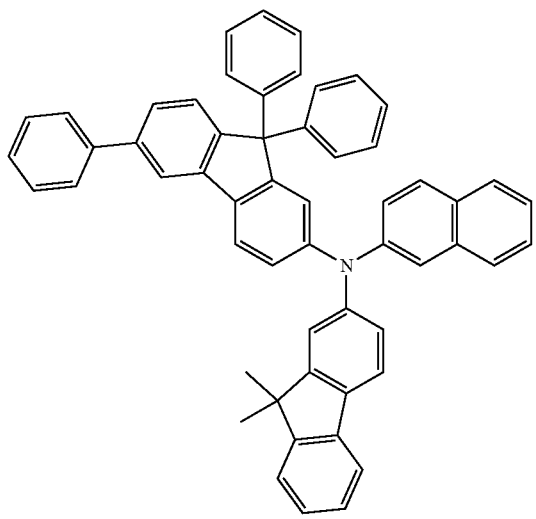
HT44
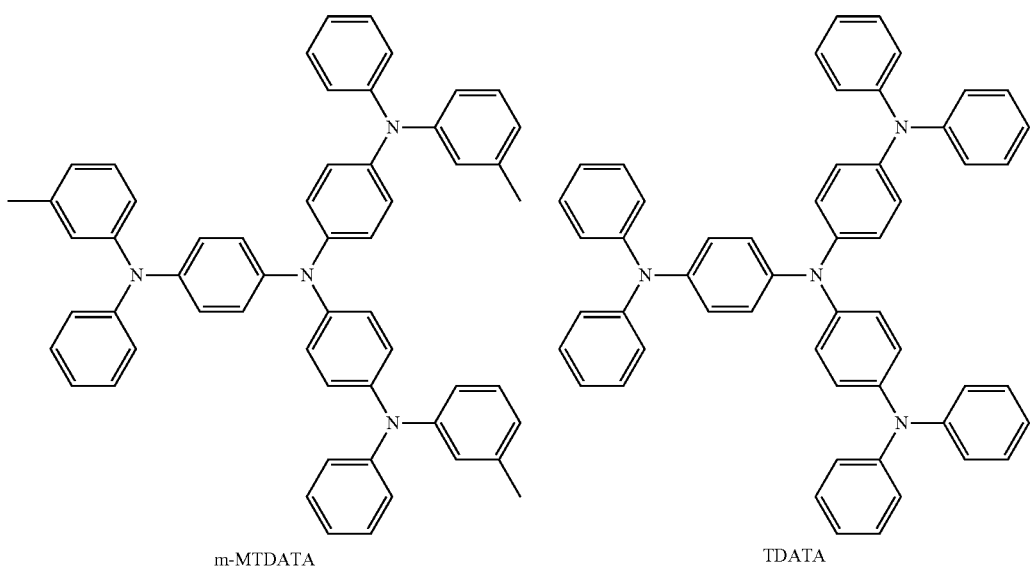
m-MTDATA TDATA

-continued
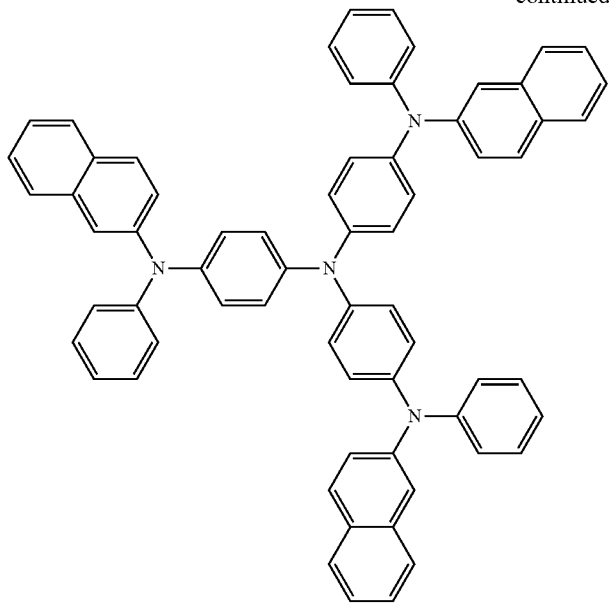
2-TNATA
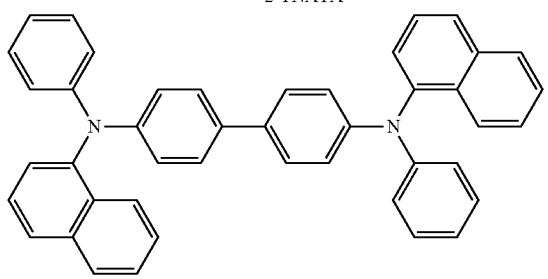
NPB
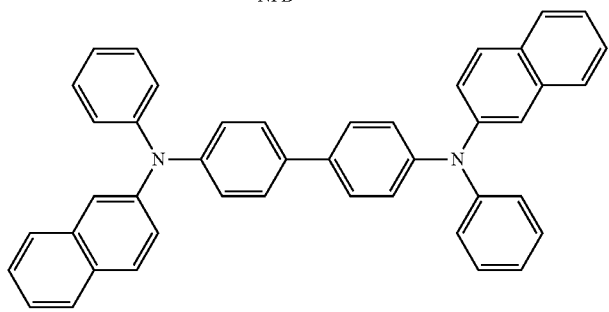
β-NPB
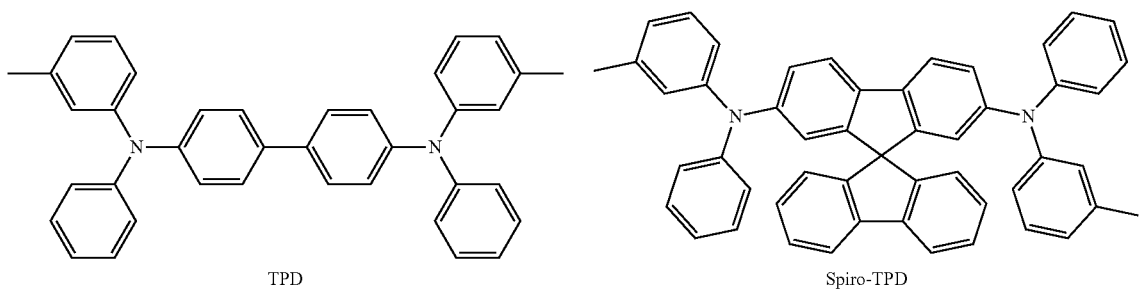
TPD          Spiro-TPD -continued

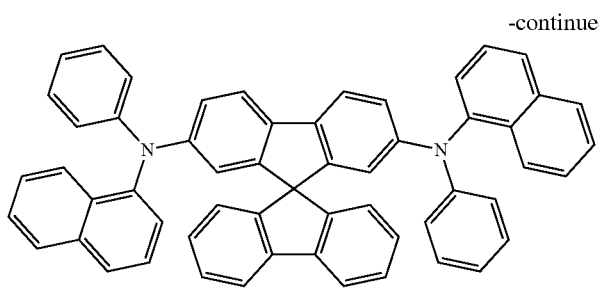

Spiro-NPB

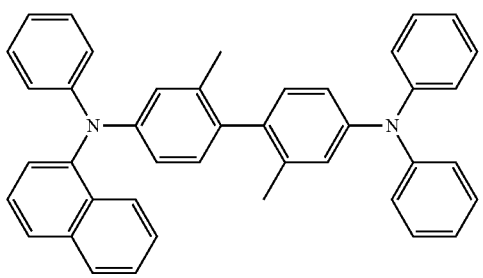

methylated-NPD

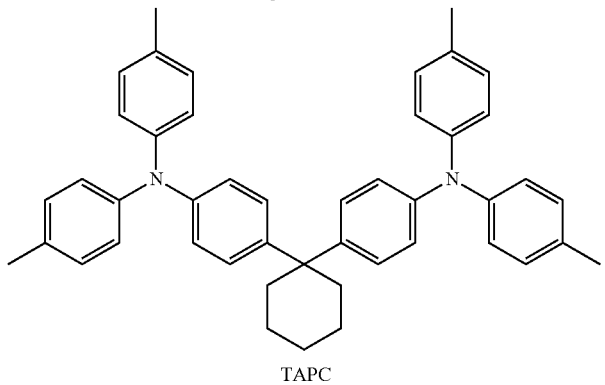

TAPC

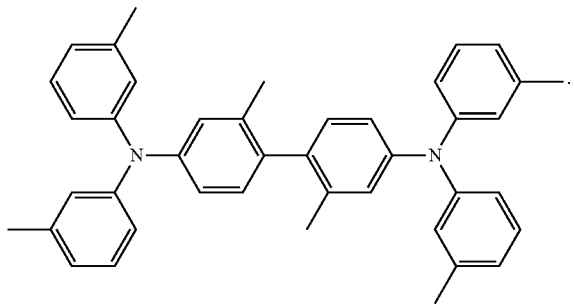

HMTPD

A thickness of the hole transport region may be in a range of about 50 Å to about 10,000 Å, for example, about 100 Å to about 4,000 Å. When the hole transport region includes a hole injection layer, a hole transport layer, or any combination thereof, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example, about 100 Å to about 1,500 Å. When the thicknesses of the hole transport region, the hole injection layer and the hole transport layer are within these ranges, suitable or satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block or reduce the flow of electrons from an electron transport region. The emission auxiliary layer and the electron blocking layer may include the materials as described above.

p-Dopant

The hole transport region may further include, in addition to these materials, a charge-generation material for the improvement of conductive properties (e.g., electrically conductive properties). The charge-generation material may be uniformly or non-uniformly dispersed in the hole transport region (for example, in the form of a single layer including (e.g., consisting of) a charge-generation material).

The charge-generation material may be, for example, a p-dopant.

In one embodiment, the lowest unoccupied molecular orbital (LUMO) energy level of the p-dopant may be −3.5 eV or less.

In an embodiment, the p-dopant may include a quinone derivative, a cyano group-containing compound, a compound containing element EL1 and element EL2, or any combination thereof.

Examples of the quinone derivative are TCNQ, F4-TCNQ, etc.

Examples of the cyano group-containing compound are HAT-CN, and a compound represented by Formula 221 below.

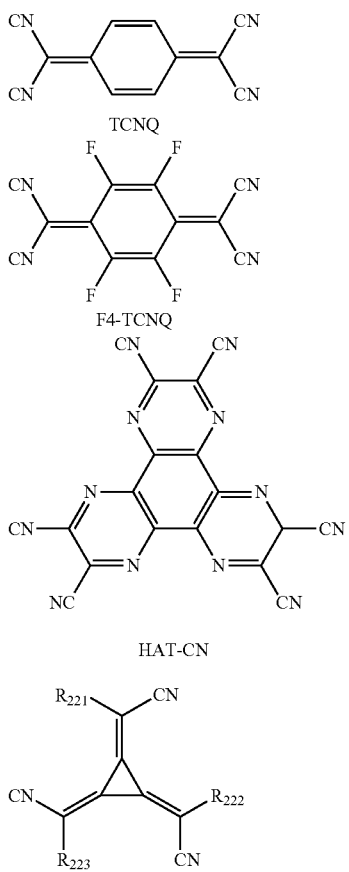

TCNQ

F4-TCNQ

HAT-CN

Formula 221

In Formula 221,
$R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and at least one selected from $R_{221}$ to $R_{223}$ may each independently be a $C_3$-$C_{60}$ carbocyclic group or a $C_1$-$C_{60}$ heterocyclic group, each substituted with a cyano group; —F; —Cl; —Br; —I; a $C_1$-$C_{20}$ alkyl group substituted with a cyano group, —F, —Cl, —Br, —I, or any combination thereof; or any combination thereof.

In the compound containing element EL1 and element EL2, element EL1 may be metal, metalloid, or a combination thereof, and element EL2 may be non-metal, metalloid, or a combination thereof.

Examples of the metal include an alkali metal (for example, lithium (Li), sodium (Na), potassium (K), rubidium (Rb), cesium (Cs), etc.); alkaline earth metal (for example, beryllium (Be), magnesium (Mg), calcium (Ca), strontium (Sr), barium (Ba), etc.); transition metal (for example, titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), etc.); post-transition metal (for example, zinc (Zn), indium (In), tin (Sn), etc.); and lanthanide metal (for example, lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), ruthenium (Lu), etc.).

Examples of the metalloid include silicon (Si), antimony (Sb), and tellurium (Te).

Examples of the non-metal include oxygen (O) and halogen (for example, F, Cl, Br, I, etc.).

In an embodiment, examples of the compound containing element EL1 and element EL2 include metal oxide, metal halide (for example, metal fluoride, metal chloride, metal bromide, and/or metal iodide), metalloid halide (for example, metalloid fluoride, metalloid chloride, metalloid bromide, and/or metalloid iodide), metal telluride, or any combination thereof.

Examples of the metal oxide include tungsten oxide (for example, WO, $W_2O_3$, $WO_2$, $WO_3$, $W_2O_5$, etc.), vanadium oxide (for example, VO, $V_2O_3$, $VO_2$, $V_2O_5$, etc.), molybdenum oxide (MoO, $Mo_2O_3$, $MoO_2$, $MoO_3$, $Mo_2O_5$, etc.), and rhenium oxide (for example, $ReO_3$, etc.).

Examples of the metal halide include alkali metal halide, alkaline earth metal halide, transition metal halide, post-transition metal halide, and lanthanide metal halide.

Examples of the alkali metal halide include LiF, NaF, KF, RbF, CsF, LiCl, NaCl, KCl, RbCl, CsCl, LiBr, NaBr, KBr, RbBr, CsBr, LiI, NaI, KI, RbI, and CsI.

Examples of the alkaline earth metal halide include $BeF_2$, $MgF_2$, $CaF_2$, $SrF_2$, $BaF_2$, $BeCl_2$, $MgCl_2$, $CaCl_2$, $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, and $BaI_2$.

Examples of the transition metal halide include titanium halide (for example, $TiF_4$, $TiCl_4$, $TiBr_4$, $TiI_4$, etc.), zirconium halide (for example, $ZrF_4$, $ZrCl_4$, $ZrBr_4$, $ZrI_4$, etc.), hafnium halide (for example, $HfF_4$, $HfCl_4$, $HfBr_4$, $HfI_4$, etc.), vanadium halide (for example, $VF_3$, $VCl_3$, $VBr_3$, $VI_3$, etc.), niobium halide (for example, $NbF_3$, $NbCl_3$, $NbBr_3$, $NbI_3$, etc.), tantalum halide (for example, $TaF_3$, $TaCl_3$, $TaBr_3$, $TaI_3$, etc.), chromium halide (for example, $CrF_3$, $CrCl_3$, $CrBr_3$, $CrI_3$, etc.), molybdenum halide (for example, $MoF_3$, $MoCl_3$, $MoBr_3$, $MoI_3$, etc.), tungsten halide (for example, $WF_3$, $WCl_3$, $WBr_3$, $WI_3$, etc.), manganese halide (for example, $MnF_2$, $MnCl_2$, $MnBr_2$, $MnI_2$, etc.), technetium halide (for example, $TcF_2$, $TcCl_2$, $TcBr_2$, $TcI_2$, etc.), rhenium halide (for example, $ReF_2$, $ReCl_2$, $ReBr_2$, $ReI_2$, etc.), iron halide (for example, $FeF_2$, $FeCl_2$, $FeBr_2$, $FeI_2$, etc.), ruthenium halide (for example, $RuF_2$, $RuCl_2$, $RuBr_2$, $RuI_2$, etc.), osmium halide (for example, $OsF_2$, $OsCl_2$, $OsBr_2$, $OsI_2$, etc.), cobalt halide (for example, $CoF_2$, $CoCl_2$, $CoBr_2$, $CoI_2$, etc.), rhodium halide (for example, $RhF_2$, $RhCl_2$, $RhBr_2$, $RhI_2$, etc.), iridium halide (for example, $IrF_2$, $IrCl_2$, $IrBr_2$, $IrI_2$, etc.), nickel halide (for example, $NiF_2$, $NiCl_2$, $NiBr_2$, $NiI_2$, etc.), palladium halide (for example, $PdF_2$, $PdCl_2$, $PdBr_2$, $PdI_2$, etc.), platinum halide (for example, $PtF_2$, $PtCl_2$, $PtBr_2$, $PtI_2$, etc.), copper halide (for example, CuF, CuCl, CuBr, CuI, etc.), silver halide (for example, AgF, AgCl, AgBr, AgI, etc.), and gold halide (for example, AuF, AuCl, AuBr, AuI, etc.).

Examples of the post-transition metal halide include zinc halide (for example, $ZnF_2$, $ZnCl_2$, $ZnBr_2$, $ZnI_2$, etc.), indium halide (for example, $InI_3$, etc.), and tin halide (for example, $SnI_2$, etc.).

Examples of the lanthanide metal halide include YbF, $YbF_2$, $YbF_3$, $SmF_3$, YbCl, $YbCl_2$, $YbCl_3$ $SmCl_3$, YbBr, $YbBr_2$, $YbBr_3$ $SmBr_3$, YbI, $YbI_2$, $YbI_3$, and $SmI_3$.

An example of the metalloid halide includes antimony halide (for example, $SbCl_5$, etc.).

Examples of the metal telluride include alkali metal telluride (for example, $Li_2Te$, $Na_2Te$, $K_2Te$, $Rb_2Te$, $Cs_2Te$, etc.), alkaline earth metal telluride (for example, BeTe, MgTe, CaTe, SrTe, BaTe, etc.), transition metal telluride (for example, $TiTe_2$, $ZrTe_2$, $HfTe_2$, $V_2Te_3$, $Nb_2Te_3$, $Ta_2Te_3$, $Cr_2Te_3$, $Mo_2Te_3$, $W_2Te_3$, MnTe, TcTe, ReTe, FeTe, RuTe, OsTe, CoTe, RhTe, IrTe, NiTe, PdTe, PtTe, $Cu_2Te$, CuTe, $Ag_2Te$, AgTe, $Au_2Te$, etc.), post-transition metal telluride (for example, ZnTe, etc.), and lanthanide metal telluride (for example, LaTe, CeTe, PrTe, NdTe, PmTe, EuTe, GdTe, TbTe, DyTe, HoTe, ErTe, TmTe, YbTe, LuTe, etc.).

Emission Layer in Interlayer 130

When the light-emitting device 10 is a full-color light-emitting device, the emission layer may be patterned into a red emission layer, a green emission layer, and/or a blue emission layer, according to a sub-pixel. In one or more embodiments, the emission layer may have a stacked structure of two or more layers of a red emission layer, a green emission layer, and a blue emission layer, in which the two or more layers contact (e.g., physically contact) each other or are separated from each other. In one or more embodiments, the emission layer may include two or more materials of a red light-emitting material, a green light-emitting material, and a blue light-emitting material, in which the two or more materials are mixed with each other in a single layer to emit white light.

The emission layer may include a host and a dopant. The dopant may include a phosphorescent dopant, a fluorescent dopant, or any combination thereof.

In an embodiment, the dopant may include the heterocyclic compound represented by Formula 1 as described herein.

The amount of the dopant in the emission layer may be from about 0.01 to about 15 parts by weight based on 100 parts by weight of the host.

In one or more embodiments, the emission layer may include a quantum dot.

In some embodiments, the emission layer may include a delayed fluorescence material. The delayed fluorescence material may act as a host or a dopant in the emission layer.

A thickness of the emission layer may be in a range of about 100 Å to about 1,000 Å, for example, about 200 Å to about 600 Å. When the thickness of the emission layer is within these ranges, excellent light-emission characteristics may be obtained without a substantial increase in driving voltage.

Host

The host in the emission layer may include any host.

In an embodiment, the host may include a compound represented by Formula 301 below:

Formula 301

In Formula 301, $Ar_{301}$ and $L_{301}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xb11 may be 1, 2, or 3, xb1 may be an integer from 0 to 5, $R_{301}$ may be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), or —P(=O)($Q_{301}$)($Q_{302}$), xb21 may be an integer from 1 to 5, and $Q_{301}$ to $Q_{303}$ are the same as described in connection with $Q_1$.

For example, xb11 in Formula 301 is 2 or more, two or more of $Ar_{301}$(s) may be linked to each other via a single bond.

In an embodiment, the host may include a compound represented by Formula 301-1, a compound represented by Formula 301-2, or any combination thereof:

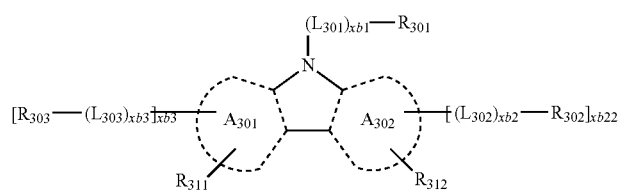

Formula 301-1

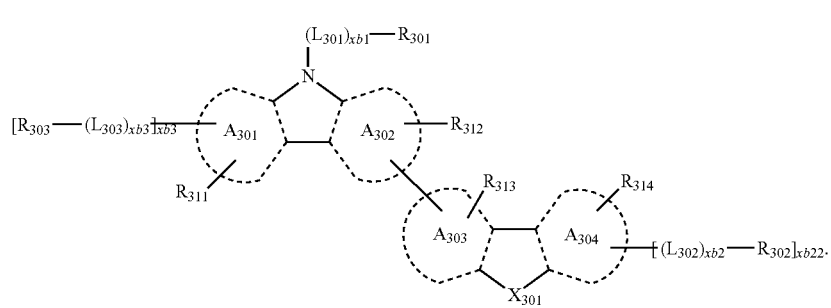

Formula 301-2

In Formulae 301-1 to 301-2, ring $A_{301}$ to ring $A_{304}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $X_{301}$ may be O, S, N-[($L_{304}$)$_{xb4}$-$R_{304}$], C($R_{304}$)($R_{305}$), or Si($R_{304}$)($R_{305}$), xb22 and xb23 may each independently be 0, 1, or 2, $L_{301}$, xb1, and $R_{301}$ are the same as described elsewhere in the present specification, $L_{302}$ to $L_{304}$ may each independently be the same as described elsewhere in connection with $L_{301}$, xb2 to xb4 may each independently be the same as described elsewhere in connection with xb1, and $R_{302}$ to $R_{305}$ and $R_{311}$ to $R_{314}$ are the same as described elsewhere in connection with $R_{301}$.

In one embodiment, the host may include an alkaline earth-metal complex. In an embodiment, the host may include a Be complex (for example, Compound H55), an Mg complex, a Zn complex, or a combination thereof.

In an embodiment, the host may include one selected from Compounds H1 to H124, 9,10-di(2-naphthyl)anthracene (ADN), 2-methyl-9,10-bis(naphthalen-2-yl)anthracene (MADN), 9,10-di-(2-naphthyl)-2-t-butyl-anthracene (TB-ADN), 4,4'-bis(N-carbazolyl)-1,1'-biphenyl (CBP), 1,3-di-9-carbazolylbenzene (mCP), 1,3,5-tri(carbazol-9-yl)benzene (TCP), 3,3-di(9H-carbazol-9-yl)biphenyl (mCBP), or any combination thereof:

H1
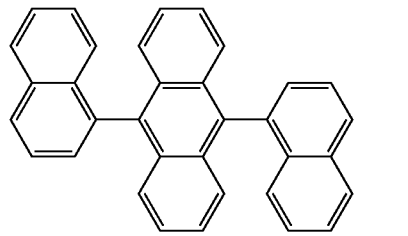

H2
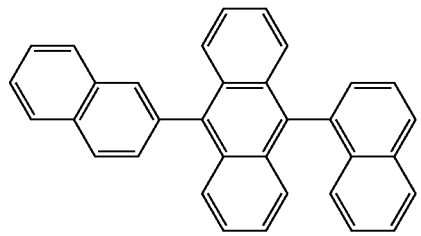

H3
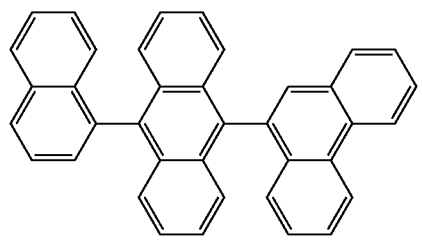

H4
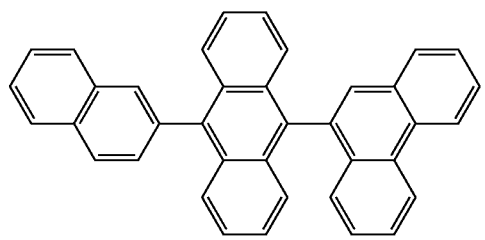

H5
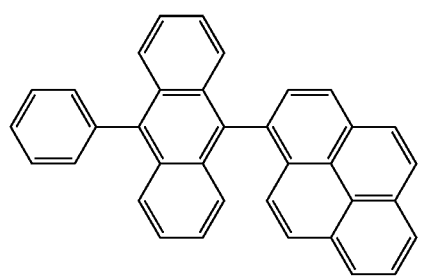

H6
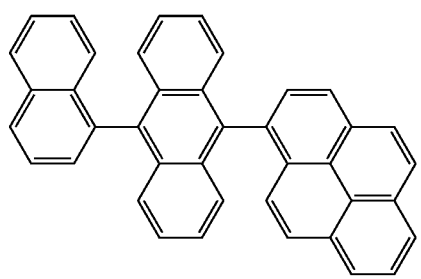

H7
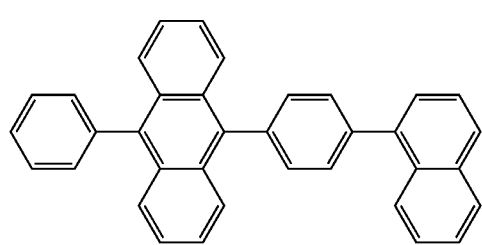

H8
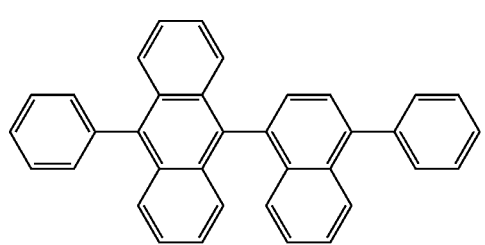

H9
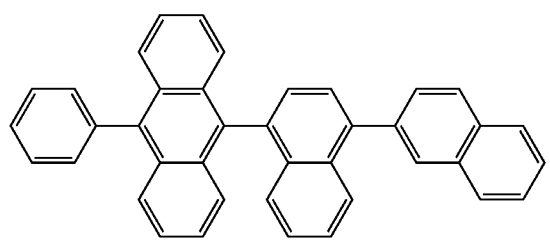

H10
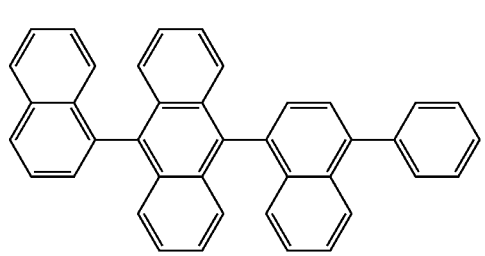

-continued
H11
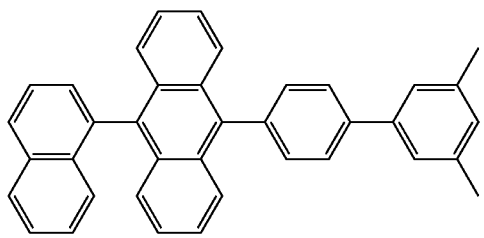
H12
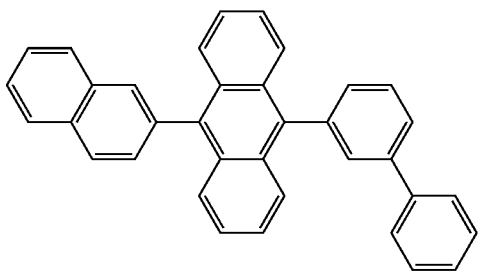
H13
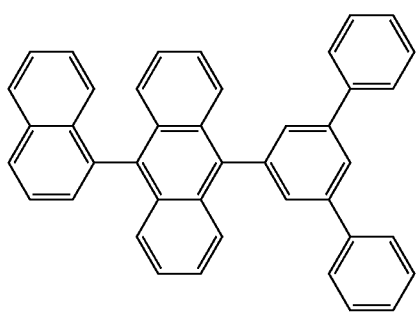
H14
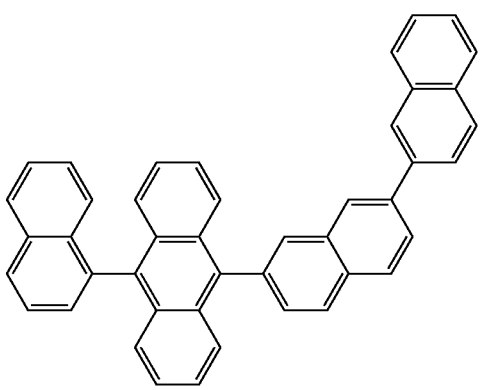
H15
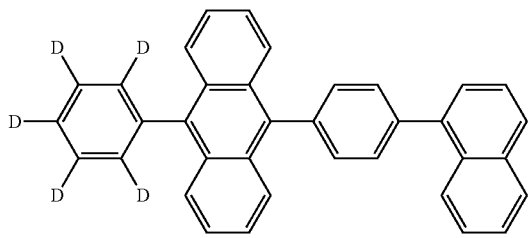
H16
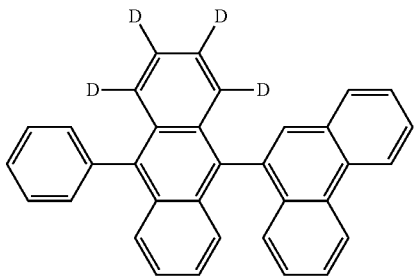
H17
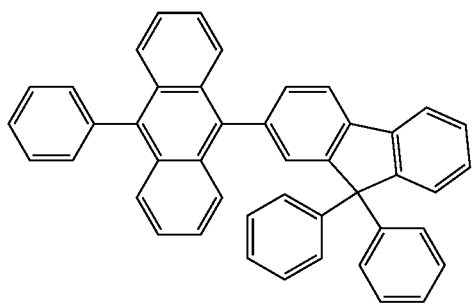
H18
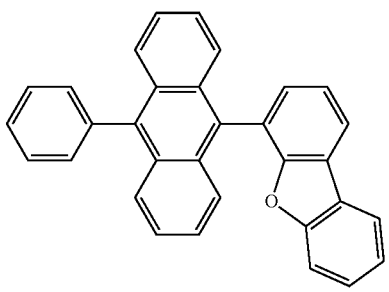
H19
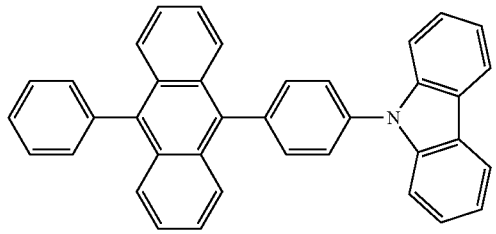
H20
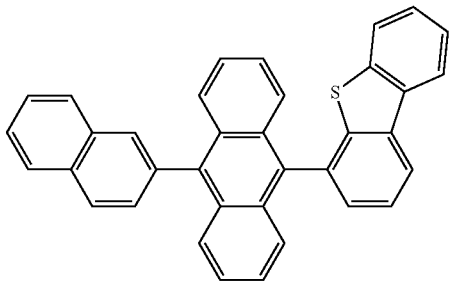

-continued
H21
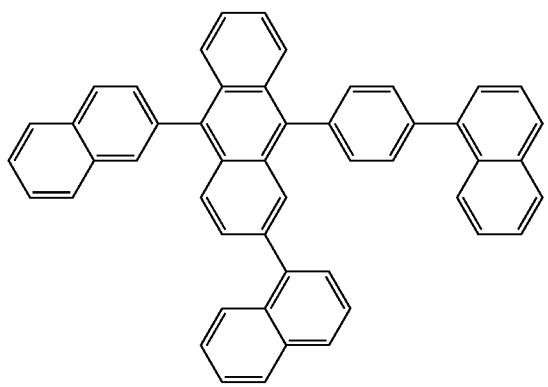
H22
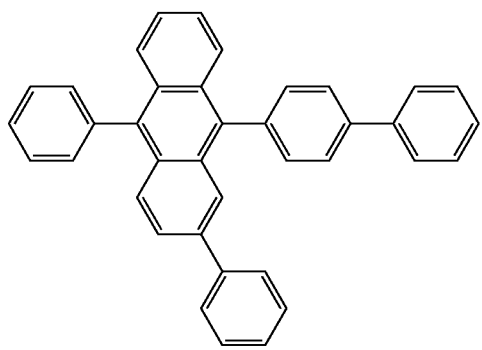
H23
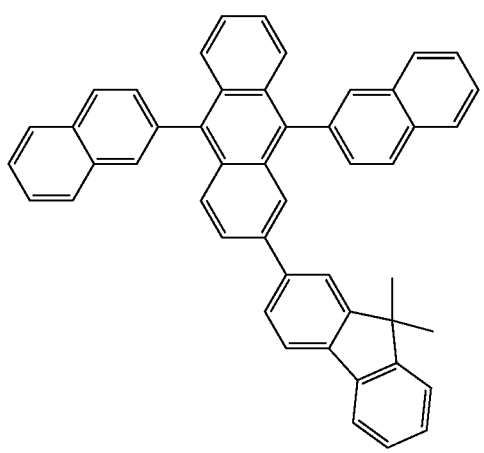
H24
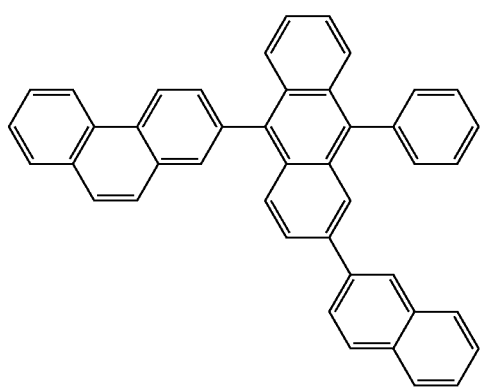
H25
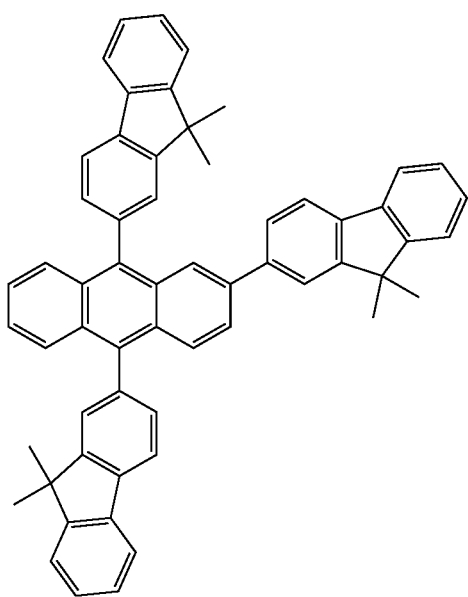
H26
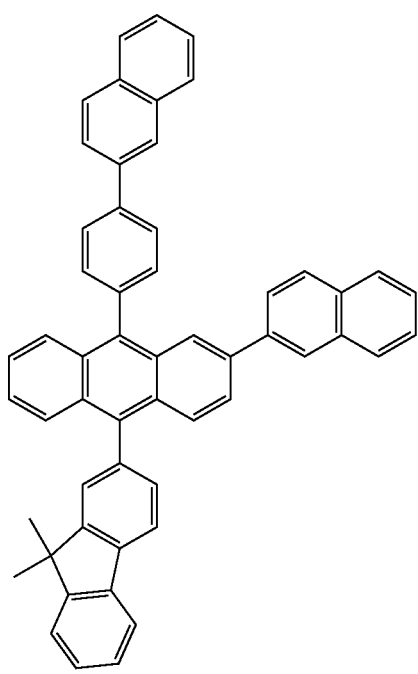

-continued
H27
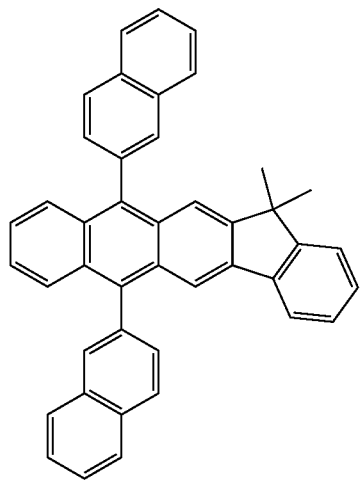
H28
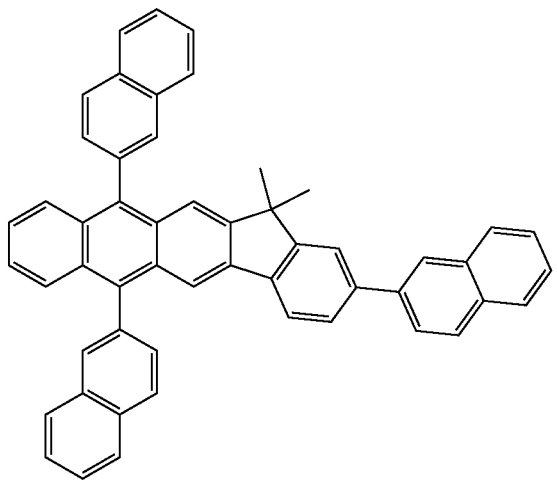
H29
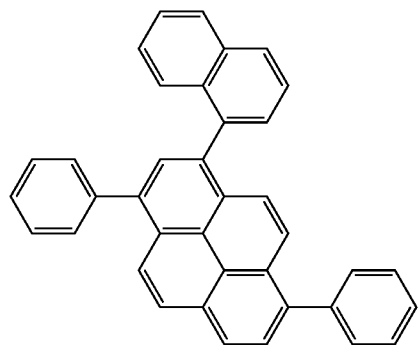
H30
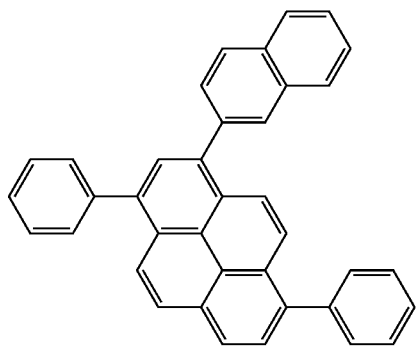
H31
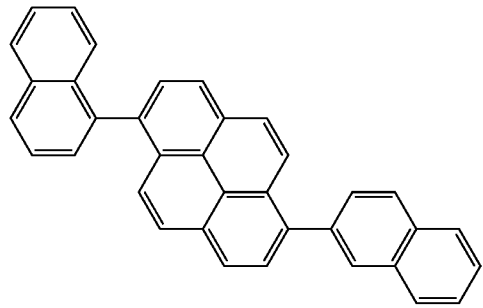
H32
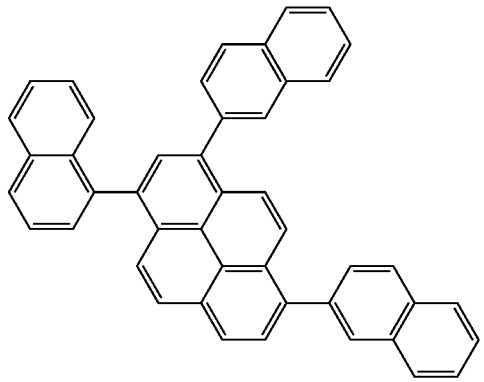
H33
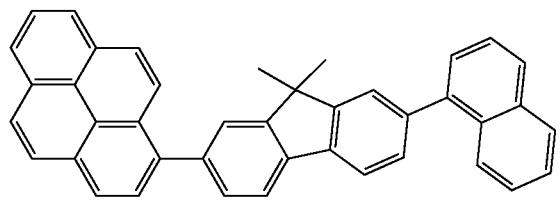
H34
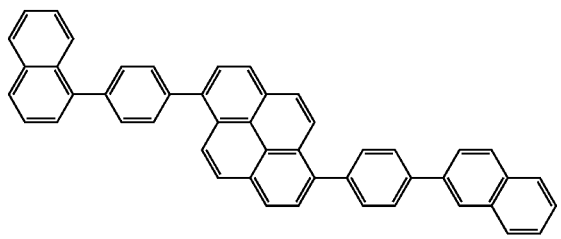

-continued
H35
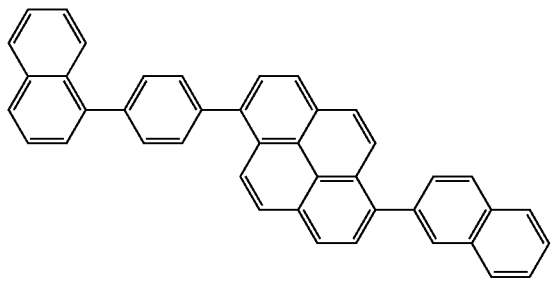
H36
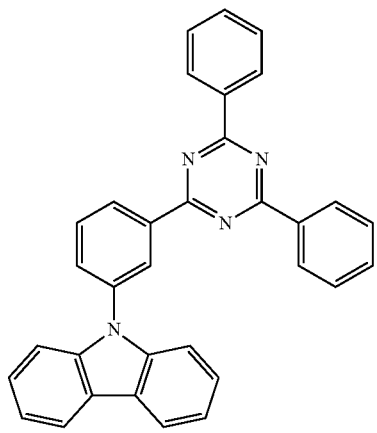
H37
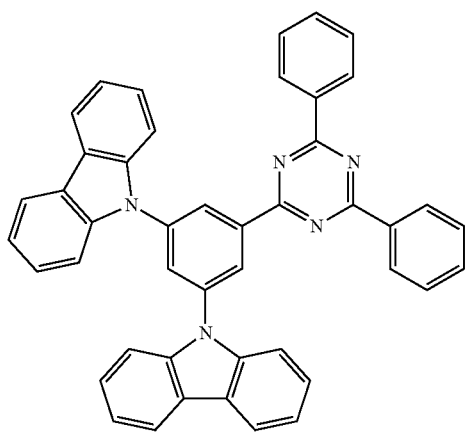
H38
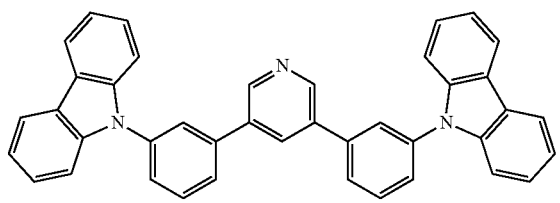
H39
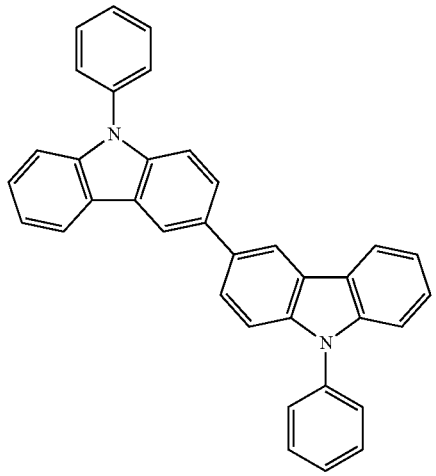
H40
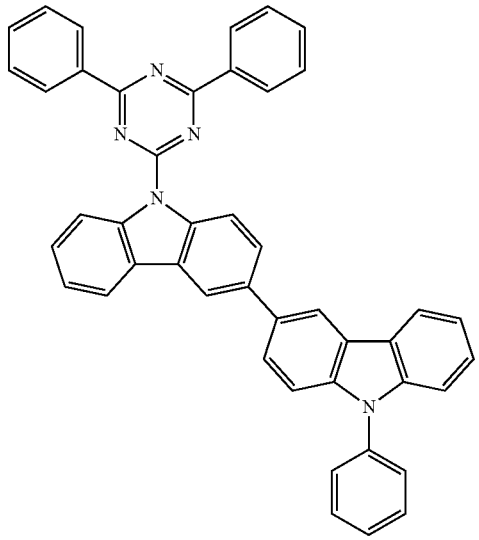

-continued
H41
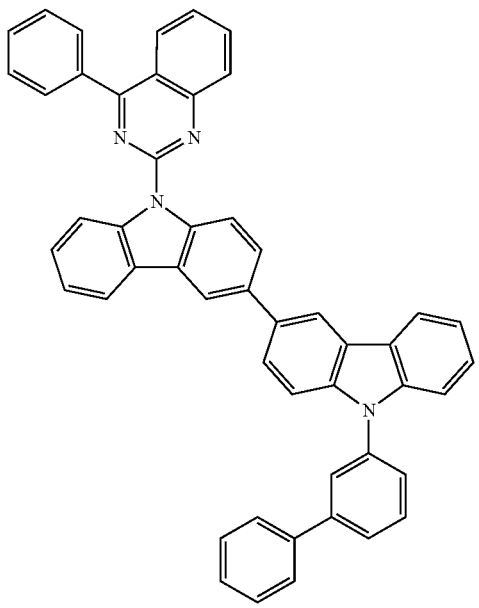
H42
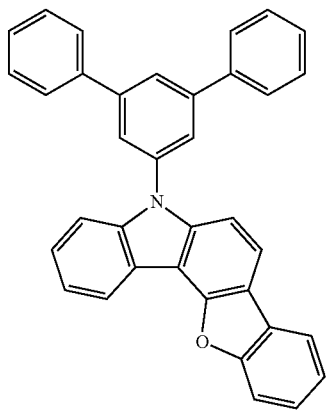
H43
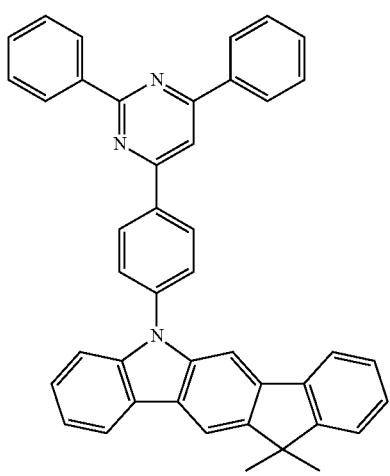
H44
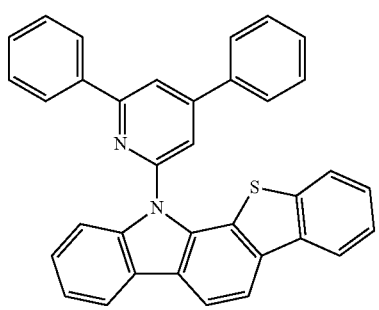
H45
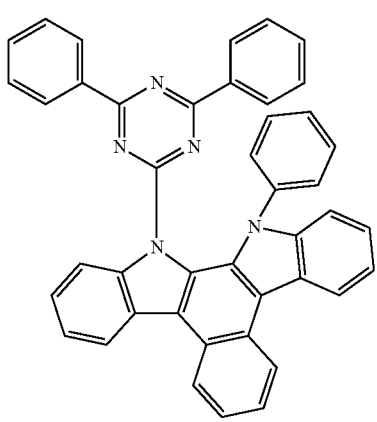
H46
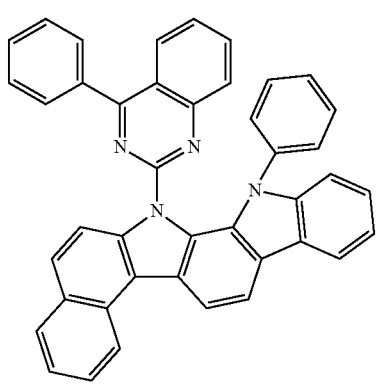

-continued
H47
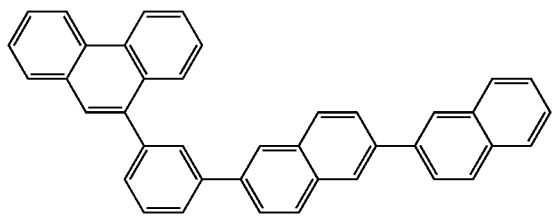
H48
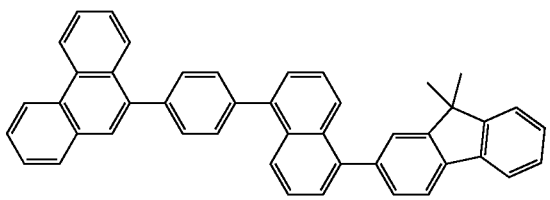
H49
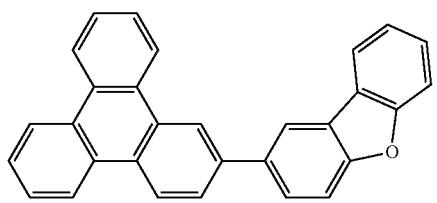
H50
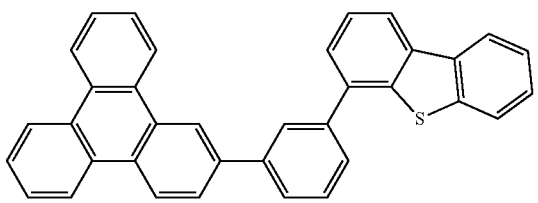
H51
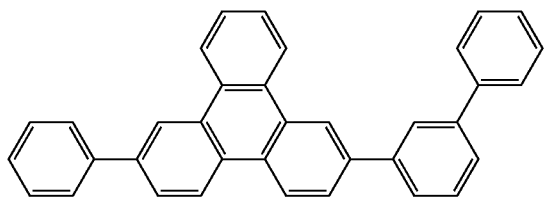
H52
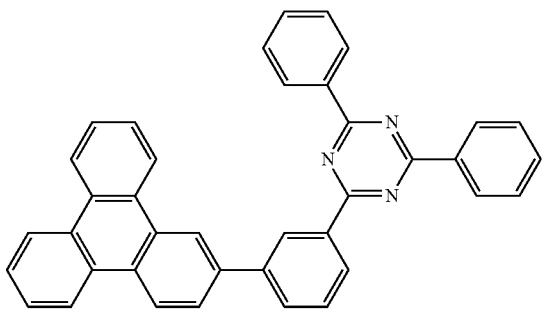
H53
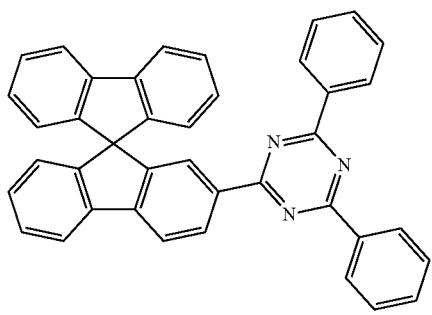
H54
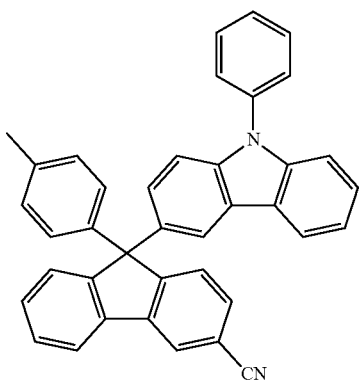
H55
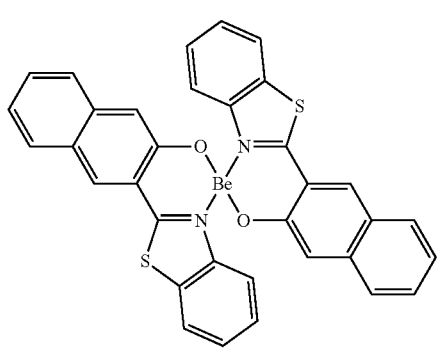
H56
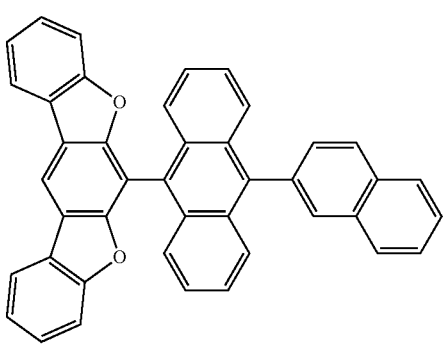

-continued
H57
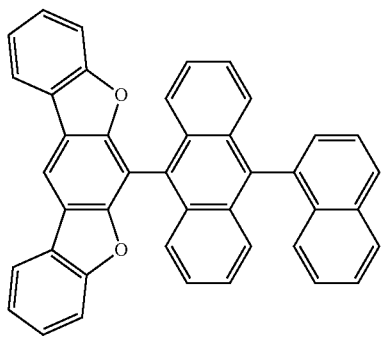
H58
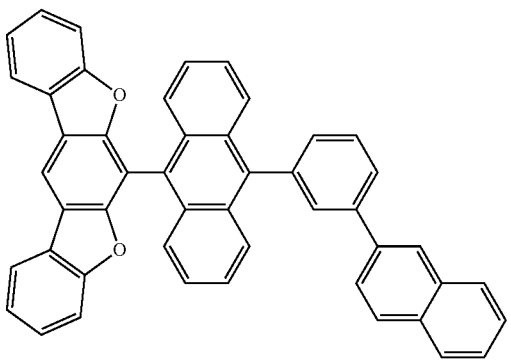
H59
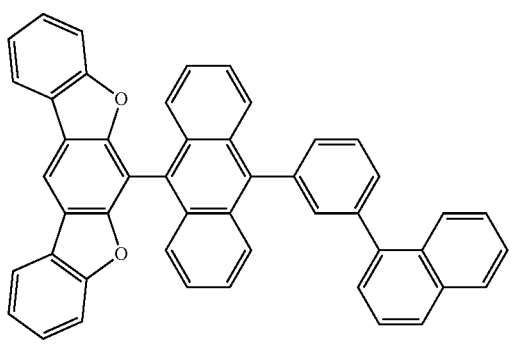
H60
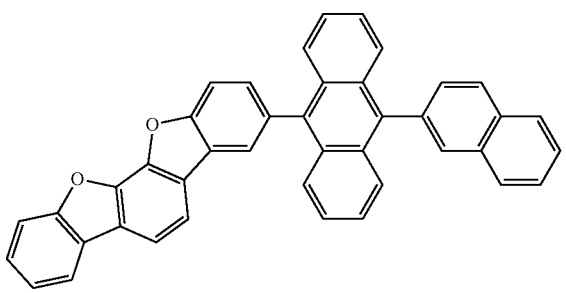
H61
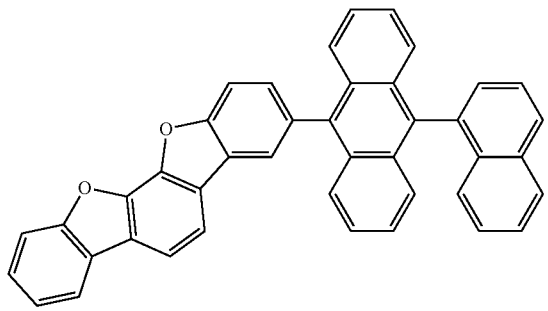
H62
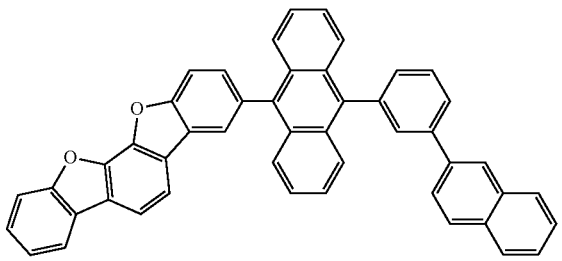
H63
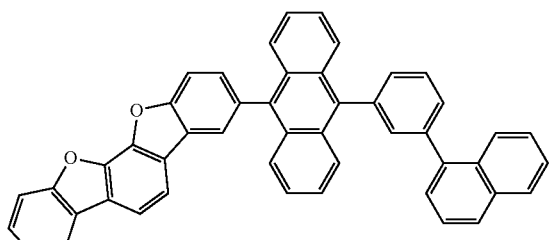
H64
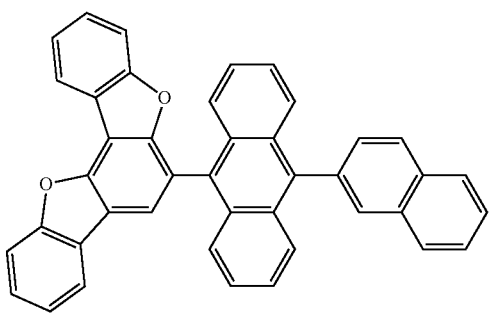

-continued
H65
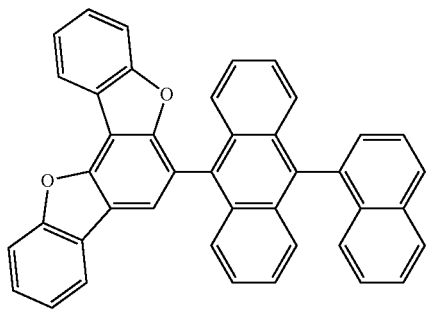
H66
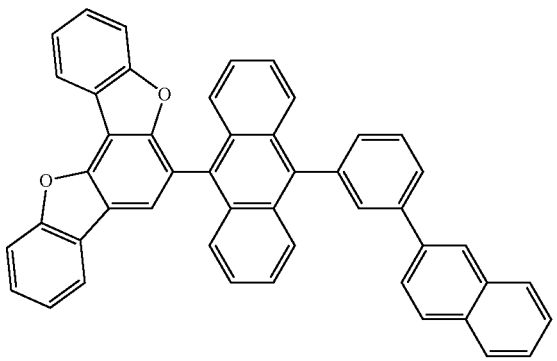
H67
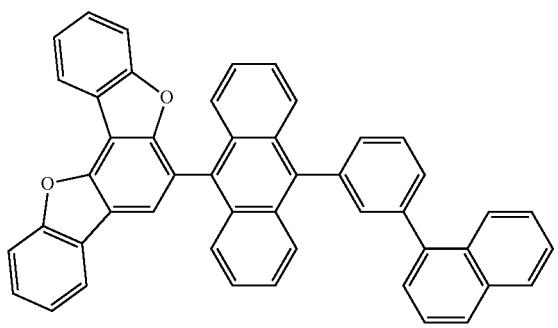
H68
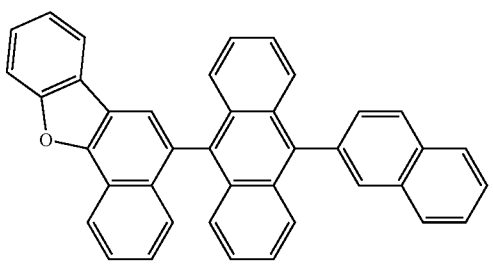
H69
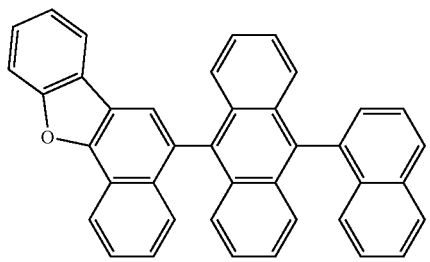
H70
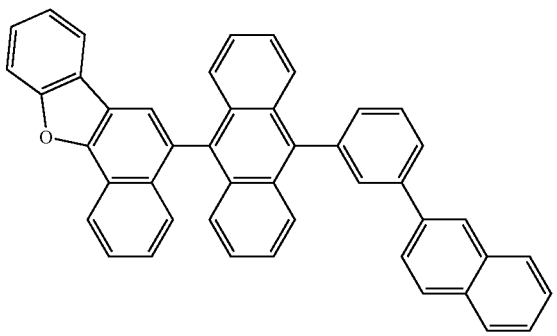
H71
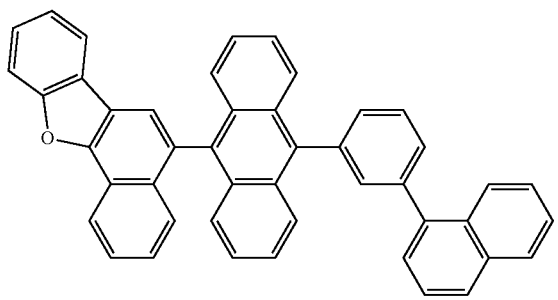
H72
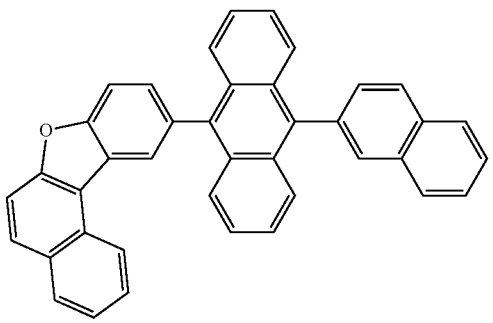

-continued
H73
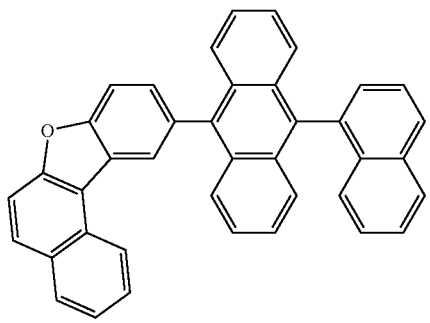
H74
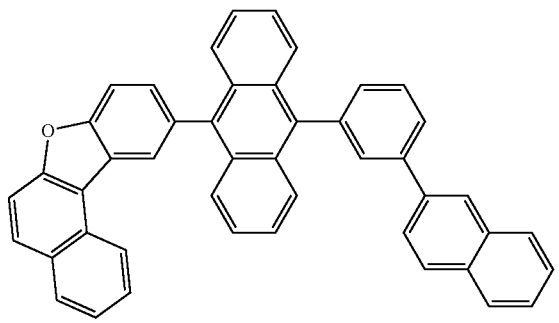
H75
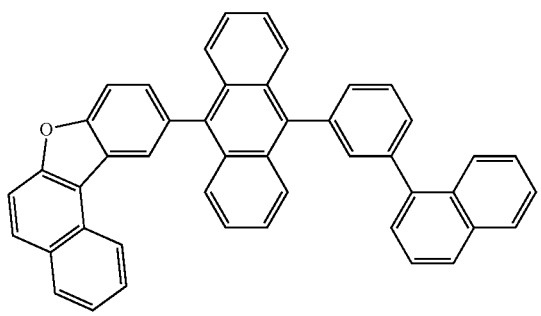
H76
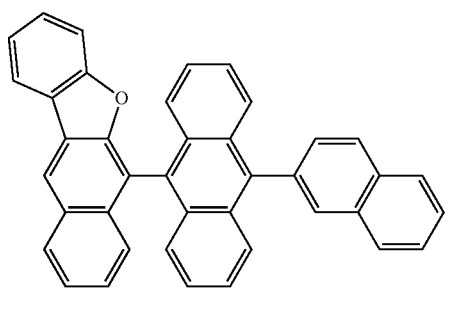
H77
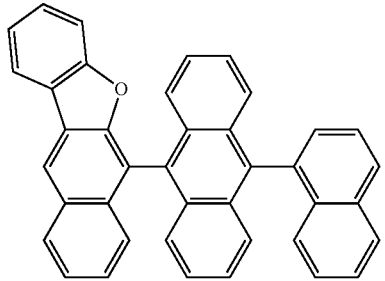
H78
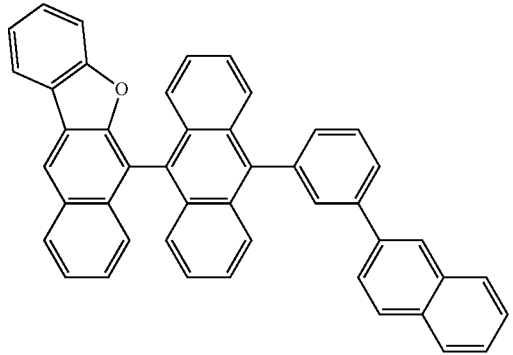
H79
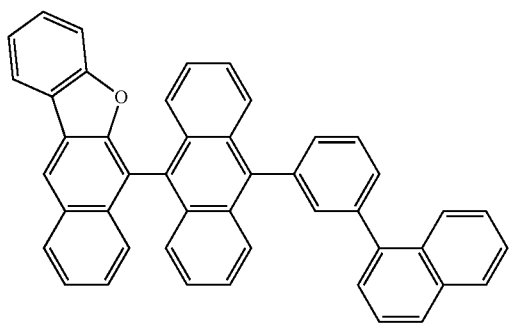
H80
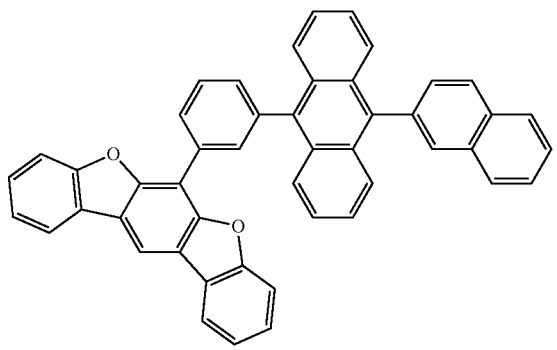

-continued
H81
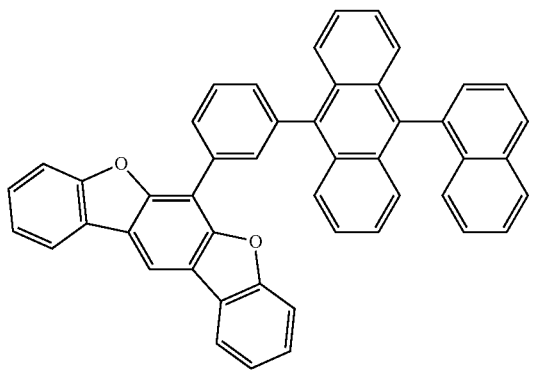
H82
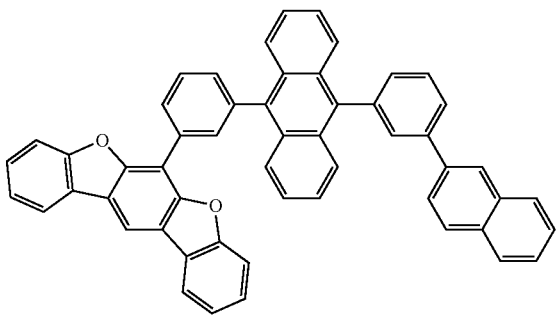
H83
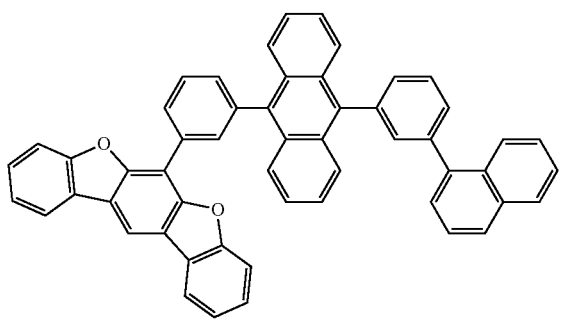
H84
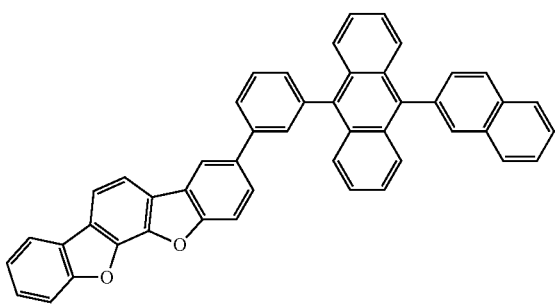
H85
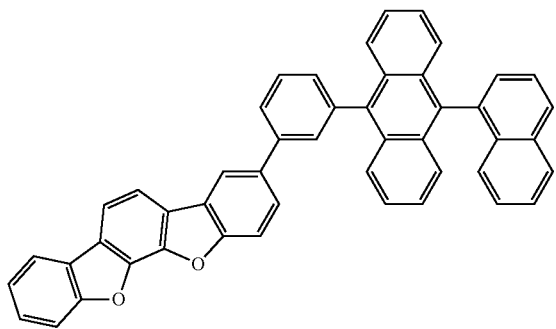
H86
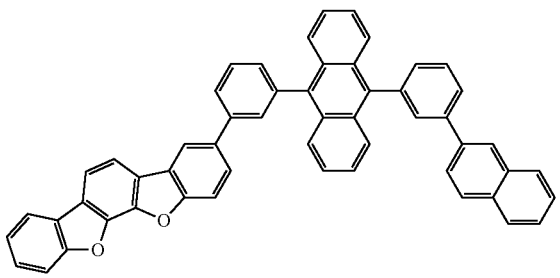
H87
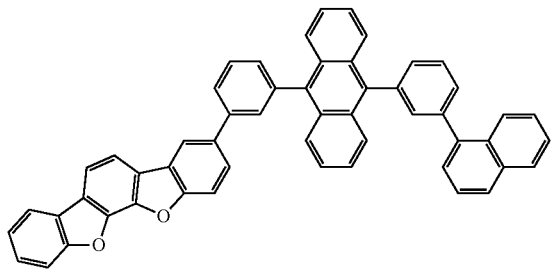
H88
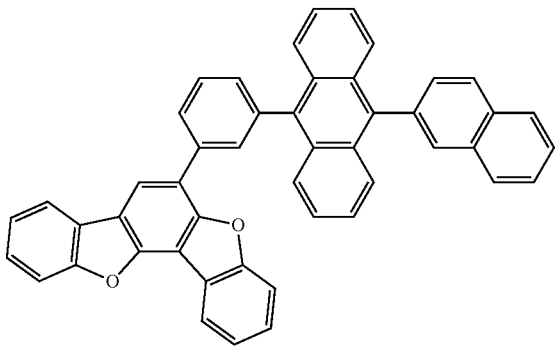

-continued
H89
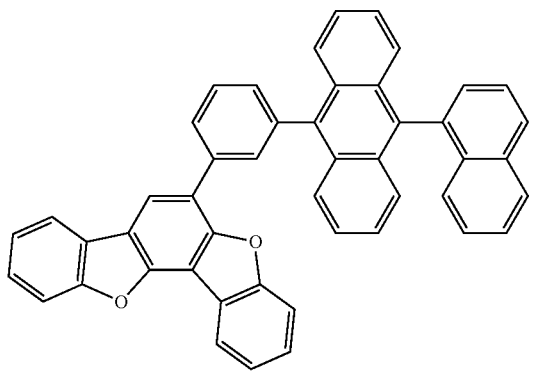
H90
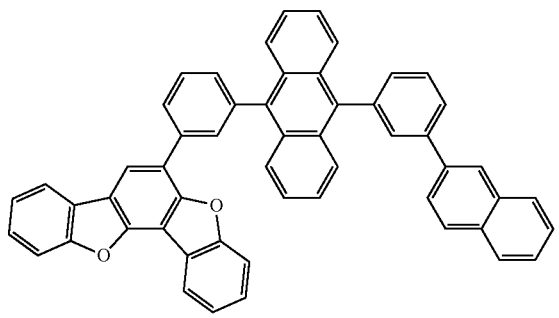
H91
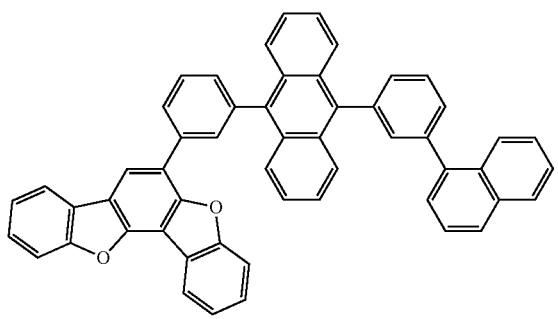
H92
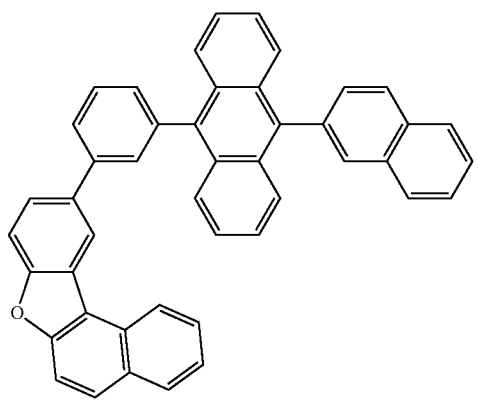
H93
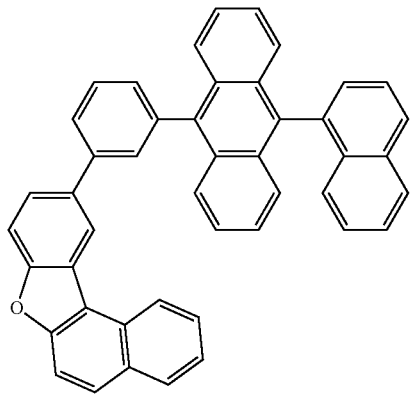
H94
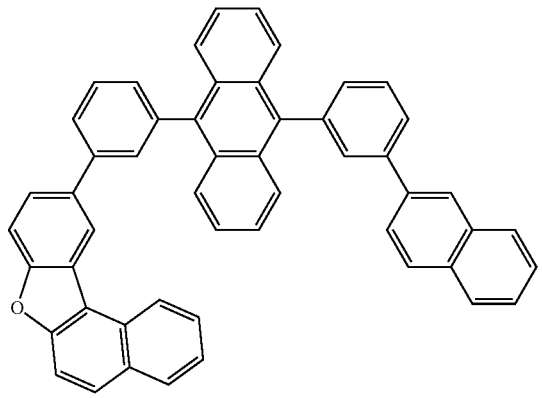
H95
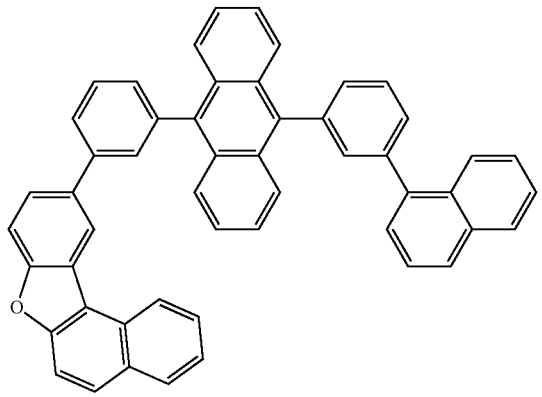
H96
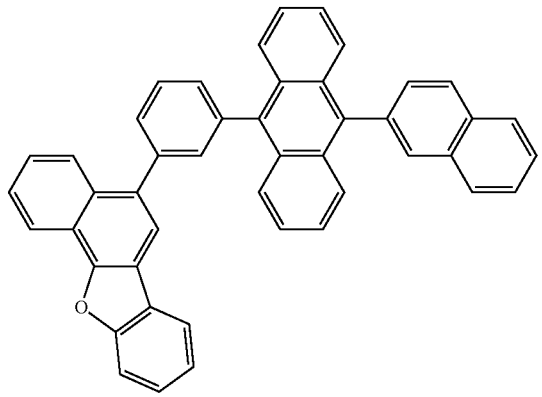

-continued
H97
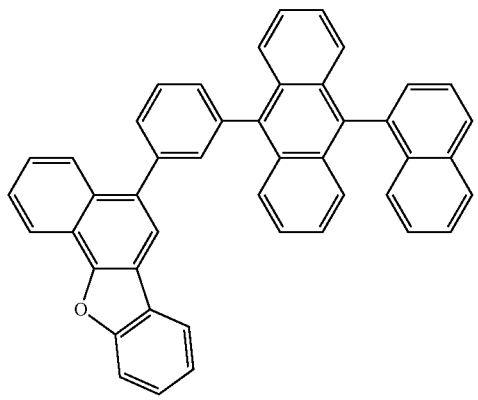
H98
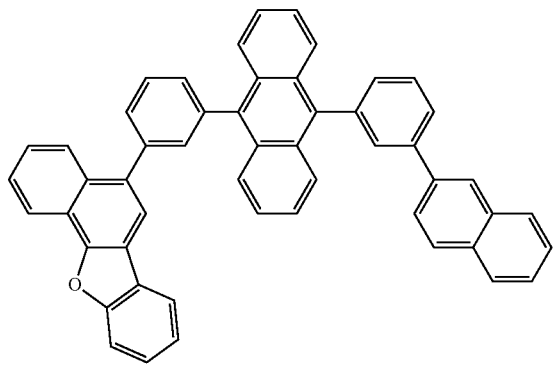
H99
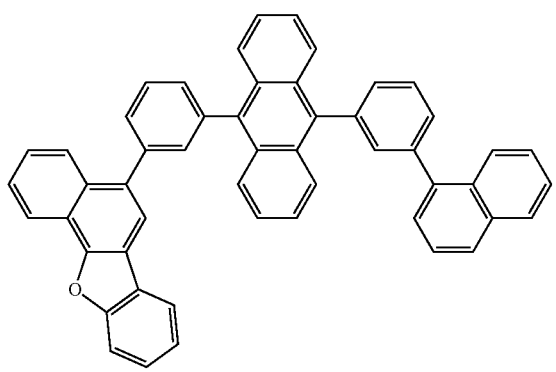
H100
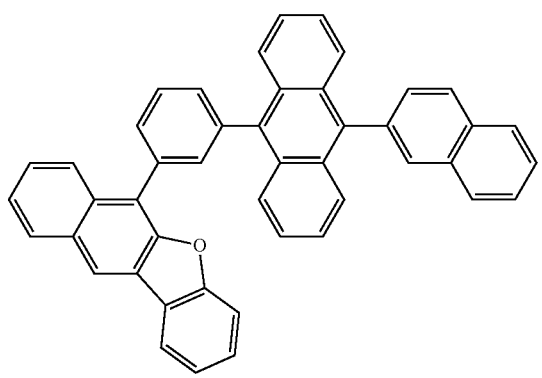
H101
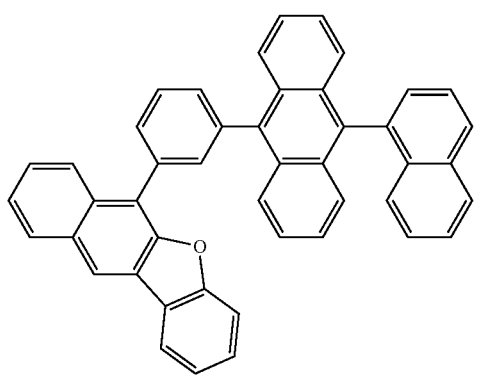
H102
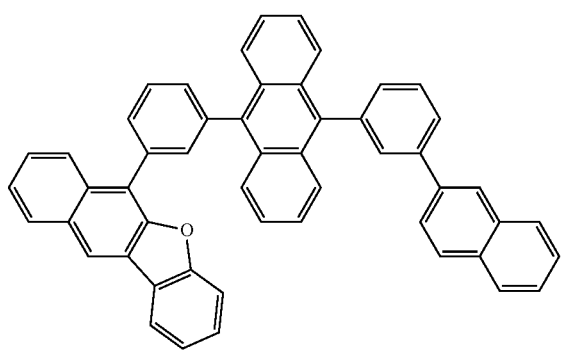

-continued
H103
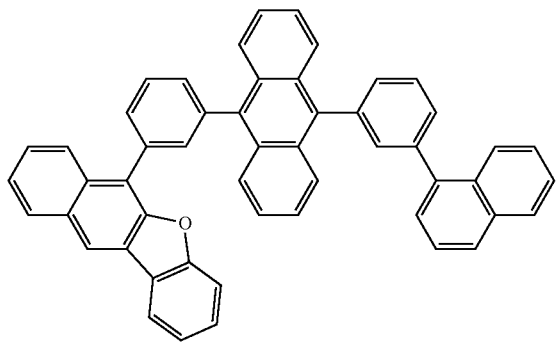
H104
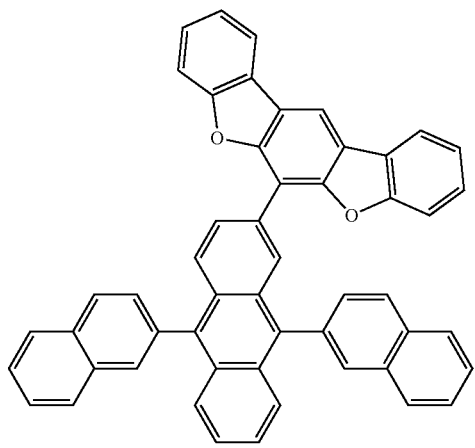
H105
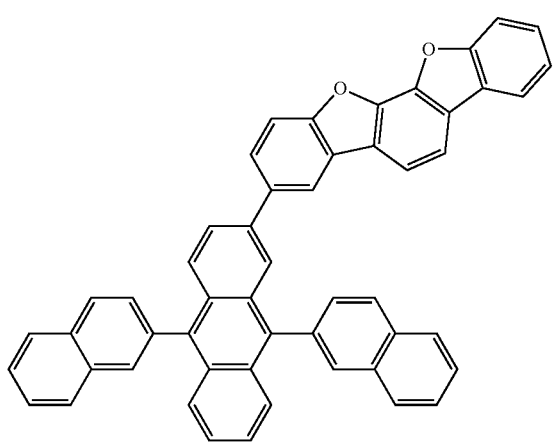
H106
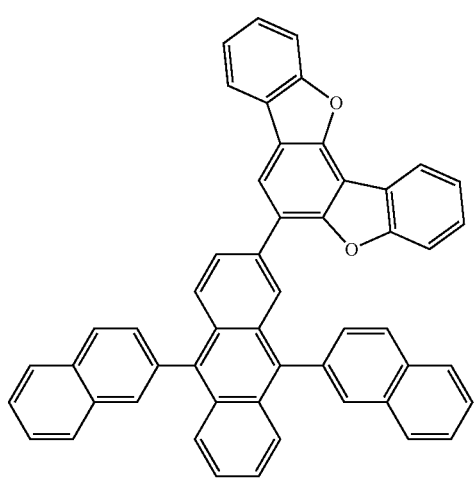
H107
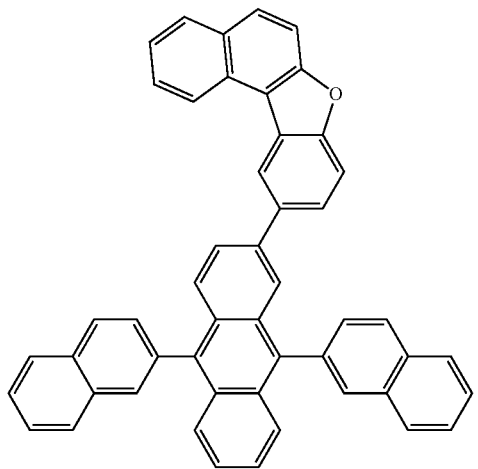
H108
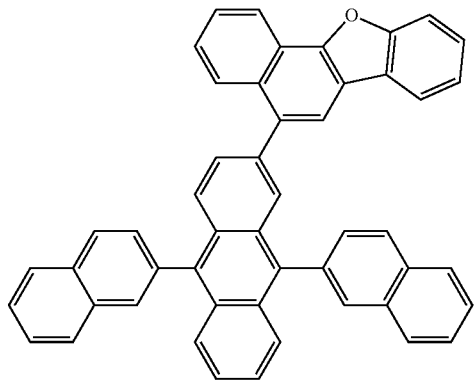

-continued
H109
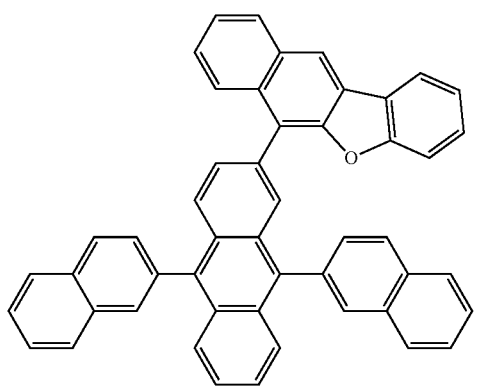
H110
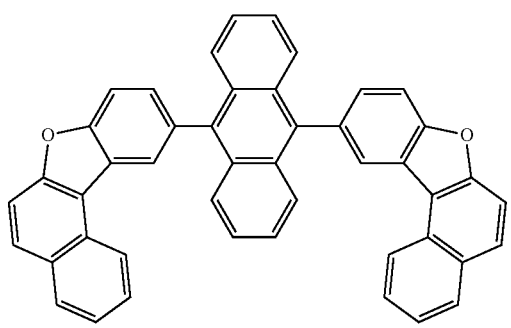
H111
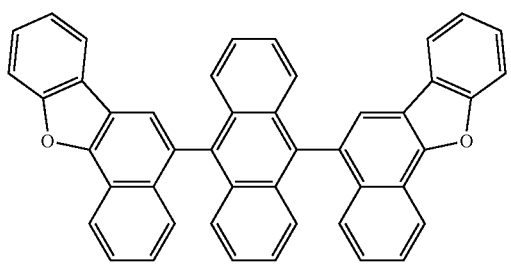
H112
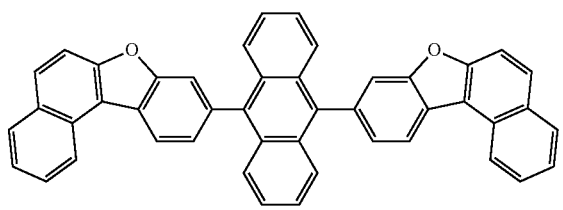
H113
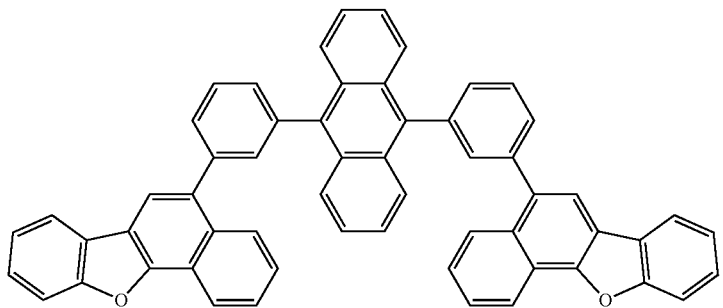
H114
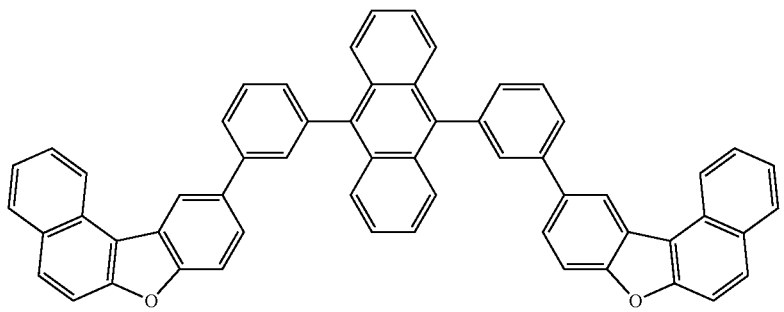

-continued
H115
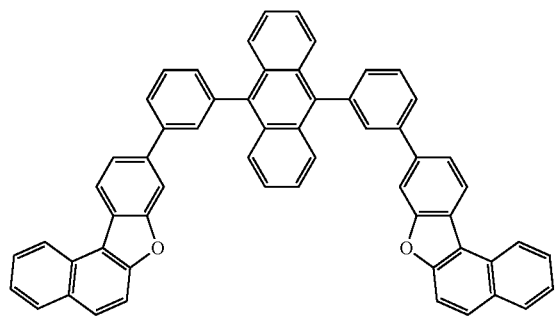
H116
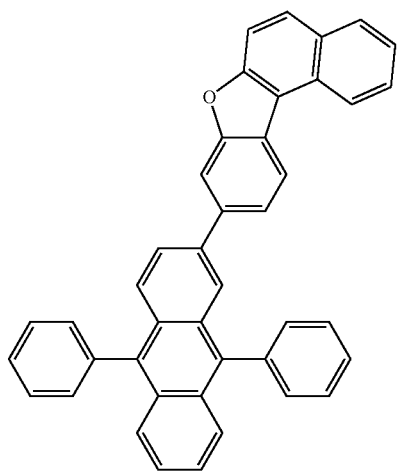
H117
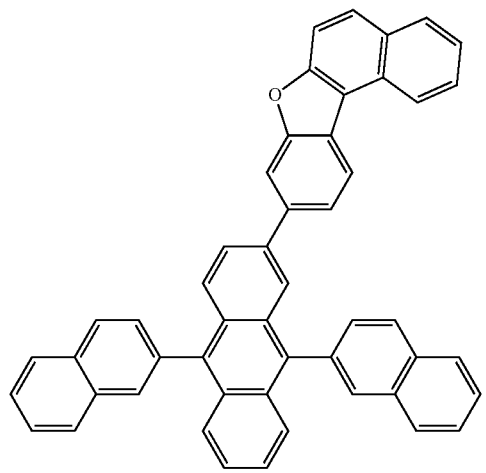
H118
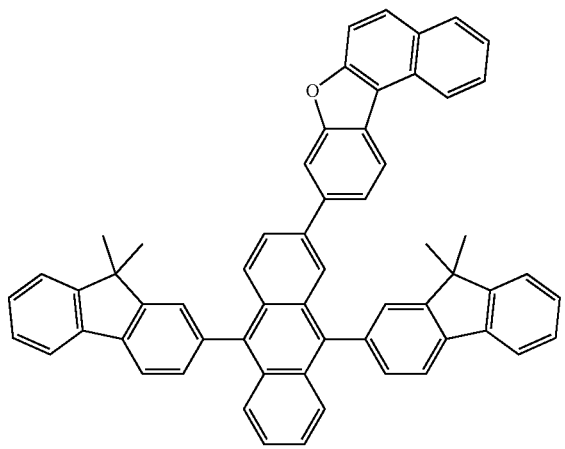
H119
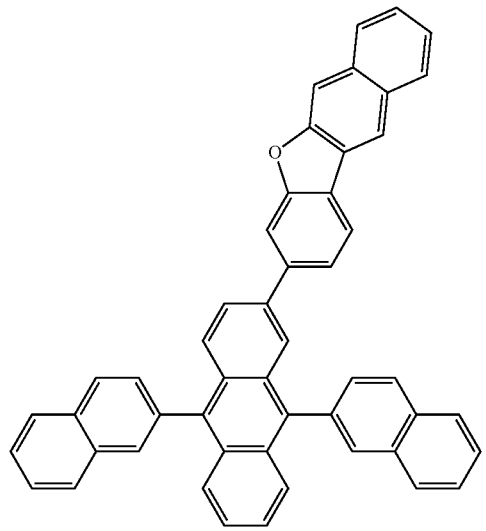
H120
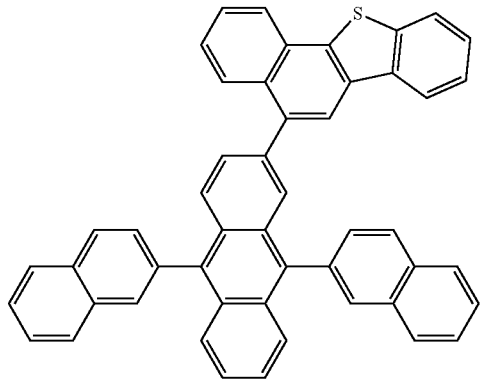

91
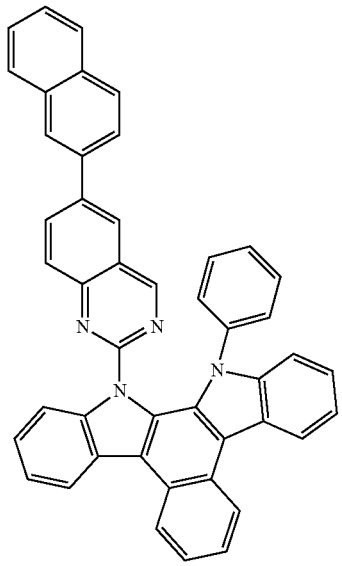
92
-continued
H121
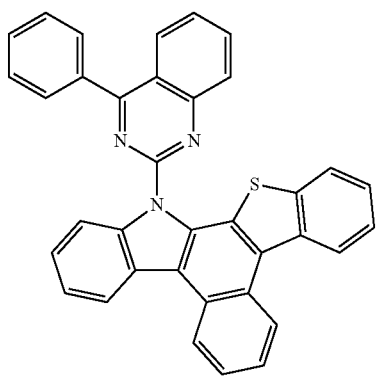
H122
H123
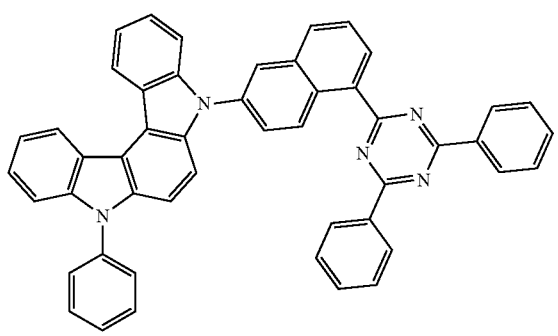
H124
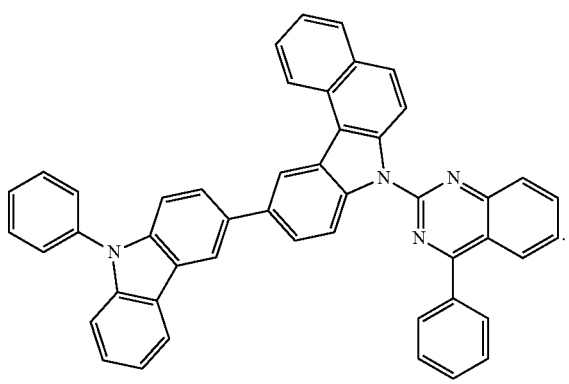

In an embodiment, the host may include a silicon-containing compound (for example, BCPDS used in the following examples and/or the like), a phosphine oxide-containing compound (for example, POPCPA used in the following examples or the like), or a combination thereof.

The present embodiment may further be implemented in various other suitable forms. For example, the host includes only one type or kind of compound or two or more different types or kinds of compounds (for example, the host of the following example includes (e.g., consists of) BCPDS and POPCPA).

Phosphorescent Dopant

In an embodiment, the phosphorescent dopant may include at least one transition metal as a central metal.

The phosphorescent dopant may include a monodentate ligand, a bidentate ligand, a tridentate ligand, a tetradentate ligand, a pentadentate ligand, a hexadentate ligand, or any combination thereof.

The phosphorescent dopant may be electrically neutral.

For example, the phosphorescent dopant may include an organometallic compound represented by Formula 401:

$$m(L_{401})_{xc1}(L_{402})_{xc2}$$ Formula 401

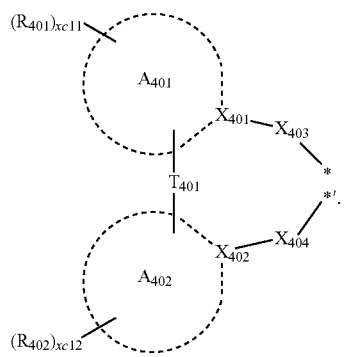

Formula 402

In Formulae 401 and 402,

M may be transition metal (for example, iridium (Ir), platinum (Pt), palladium (Pd), osmium (Os), titanium (Ti), gold (Au), hafnium (Hf), europium (Eu), terbium (Tb), rhodium (Rh), rhenium (Re), or thulium (Tm)), $L_{401}$ may be a ligand represented by Formula 402, and xc1 may be 1, 2, or 3, wherein when xc1 is two or more, two or more of $L_{401}(s)$ may be identical to or different from each other, $L_{402}$ may be an organic ligand, and xc2 may be 0, 1, 2, 3, or 4, and when xc2 is 2 or more, two or more of $L_{402}(s)$ may be identical to or different from each other, $X_{401}$ and $X_{402}$ may each independently be nitrogen or carbon, ring $A_{401}$ and ring $A_{402}$ may each independently be a $C_3$-$C_{60}$ carbocyclic group or a $C_1$-$C_{60}$ heterocyclic group, $T_{401}$ may be a single bond, *—O—*', *—S—*', *—C (=O)—*', *—N($Q_{411}$)*', *—C($Q_{411}$)($Q_{412}$)-*', *—C($Q_1$)=C($Q_{41}$)-*', *—C($Q_{411}$)=*', or *=C($Q_1$)—*', $X_{403}$ and $X_{404}$ may each independently be a chemical bond (for example, a covalent bond or a coordination bond (e.g., a coordinate covalent bond or dative bond)), O, S, N($Q_{413}$), B($Q_{413}$), P($Q_{413}$), C($Q_{413}$)($Q_{414}$), or Si($Q_{413}$)($Q_{414}$), $Q_{411}$ to $Q_{414}$ are the same as described in connection with $Q_1$, $R_{401}$ and $R_{402}$ may each independently be hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{401}$)($Q_{402}$)($Q_{403}$), N($Q_{401}$)($Q_{402}$), —B($Q_{401}$)($Q_{402}$), —C(=O)($Q_{401}$), —S(=O)$_2$($Q_{401}$), or —P(=O)($Q_{401}$)($Q_{402}$), $Q_{401}$ to $Q_{403}$ are the same as described in connection with $Q_1$, xc11 and xc12 may each independently be an integer from 0 to 10,

* and *' in Formula 402 each indicates a binding site to M in Formula 401.

For example, in Formula 402, i) $X_{401}$ is nitrogen, and $X_{402}$ is carbon, or ii) each of $X_{401}$ and $X_{402}$ is nitrogen.

In an embodiment, when xc1 in Formula 402 is 2 or more, two ring $A_{401}$ in two or more of $L_{401}(s)$ may be optionally linked to each other via $T_{402}$, which is a linking group, and two ring $A_{402}$ may optionally be linked to each other via $T_{403}$, which is a linking group (see Compounds PD1 to PD4 and PD7). $T_{402}$ and $T_{403}$ are the same as described in connection with $T_{401}$.

$L_{402}$ in Formula 401 may be an organic ligand. For example, $L_{402}$ may include a halogen group, a diketone group (for example, an acetylacetonate group), a carboxylic acid group (for example, a picolinate group), —C(=O), an isonitrile group, —CN group, a phosphorus group (for example, a phosphine group, a phosphite group, etc.), or any combination thereof.

The phosphorescent dopant may include, for example, one selected from compounds PD1 to PD25, or any combination thereof:

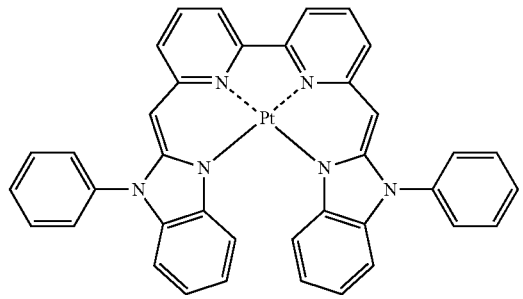

PD1

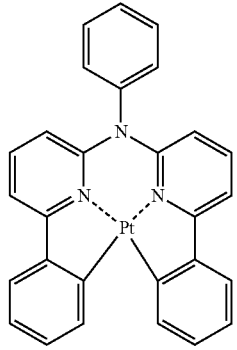

PD2

-continued
PD3
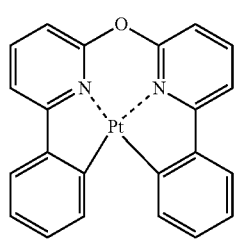
PD4
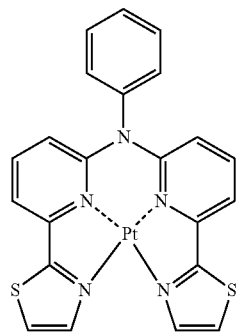
PD5
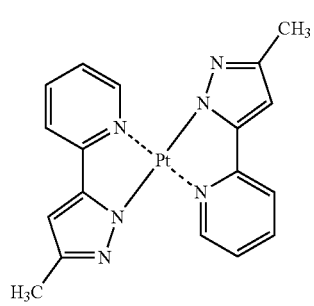
PD6
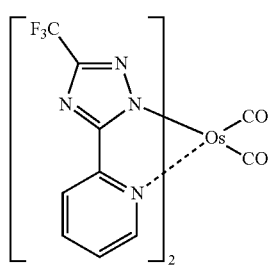
PD7
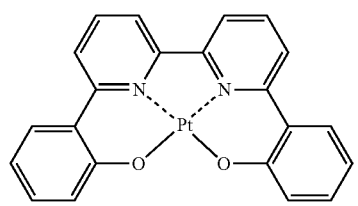
PD8
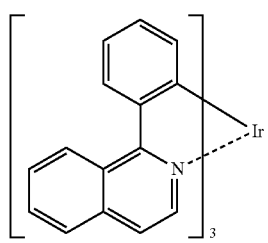
-continued
PD9
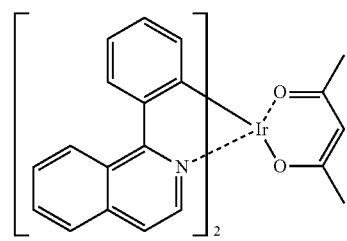
PD10
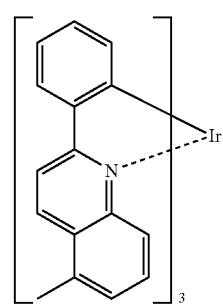
PD11
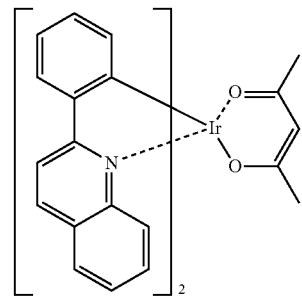
PD12
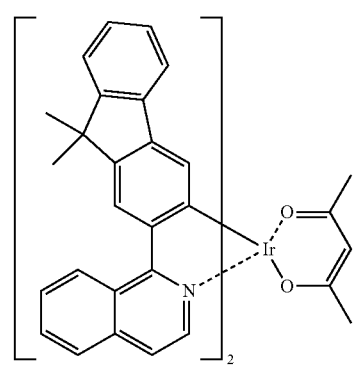
PD13
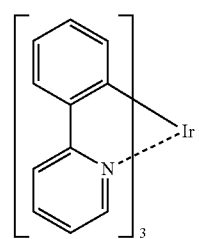

PD14 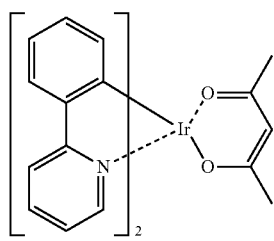
PD15 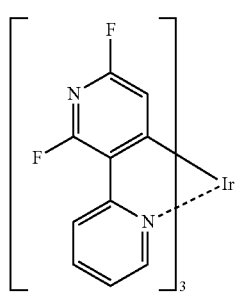
PD16 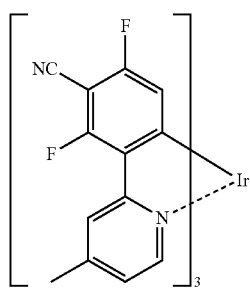
PD17 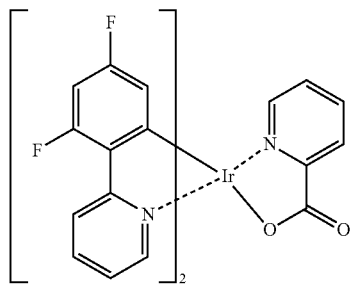
PD18 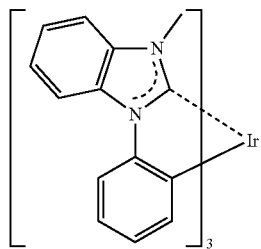
PD19 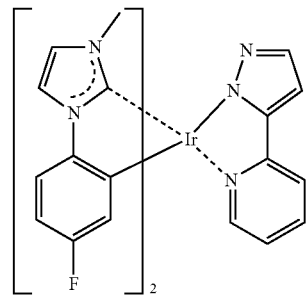
PD20 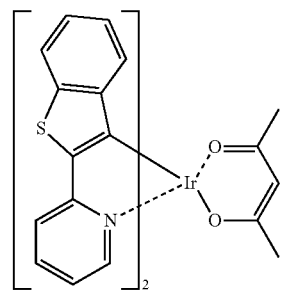
PD21 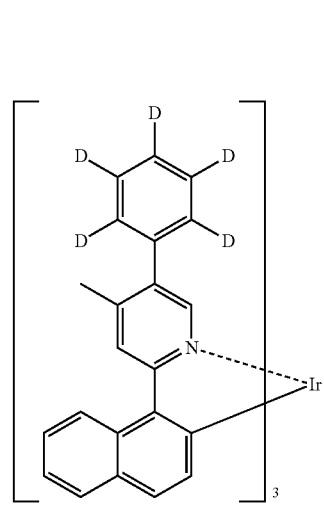
PD22 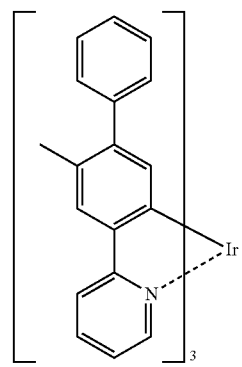

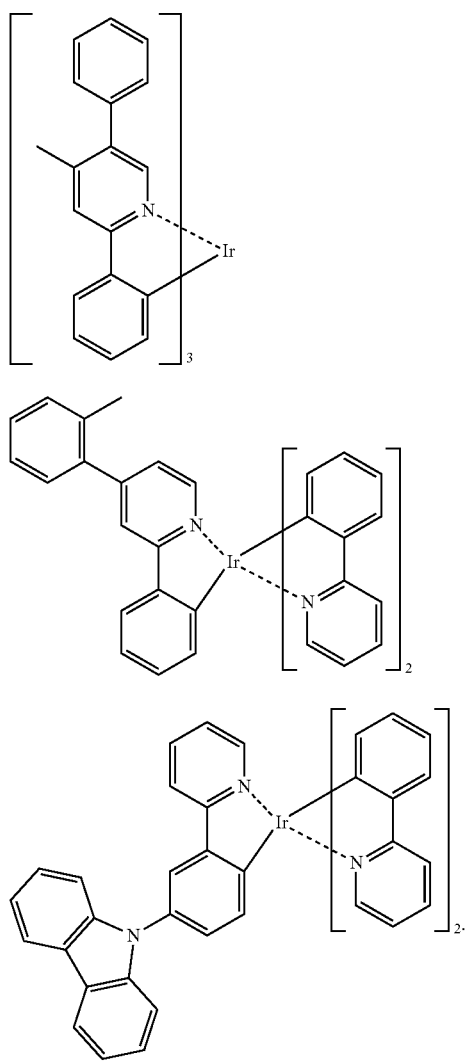

Delayed Fluorescence Material

In some embodiments, the emission layer may include a delayed fluorescence material.

In the present specification, the delayed fluorescence material may be selected from compounds capable of emitting delayed fluorescence based on a delayed fluorescence emission mechanism.

The delayed fluorescent material included in the emission layer may act as a host or a dopant depending on the type or kind of other materials included in the emission layer.

In an embodiment, the difference between the triplet energy level (eV) of the delayed fluorescence material and the singlet energy level (eV) of the delayed fluorescence material may be greater than or equal to 0 eV and less than or equal to 0.5 eV. When the difference between the triplet energy level (eV) of the delayed fluorescent material and the singlet energy level (eV) of the delayed fluorescent material satisfies the above-described range, up-conversion from the triplet state to the singlet state of the delayed fluorescent materials may effectively occur, and thus, the luminescence efficiency of the light-emitting device 10 may be improved.

In an embodiment, the delayed fluorescence material may include i) a material including at least one electron donor (for example, a π electron-rich $C_3$-$C_{60}$ cyclic group, such as a carbazole group) and at least one electron acceptor (for example, a sulfoxide group, a cyano group, or a π electron-deficient nitrogen-containing $C_1$-$C_{60}$ cyclic group), and ii) a material including a $C_8$-$C_{60}$ polycyclic group in which two or more cyclic groups are condensed (e.g., combined together) while sharing boron (B).

In an embodiment, the delayed fluorescence material may include at least one selected from the following compounds DF1 to DF9:

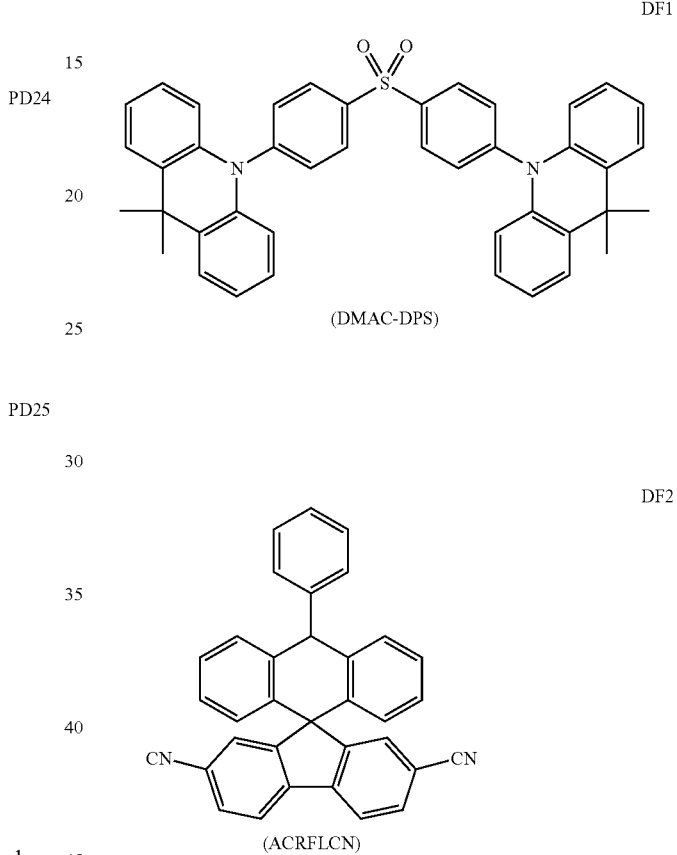

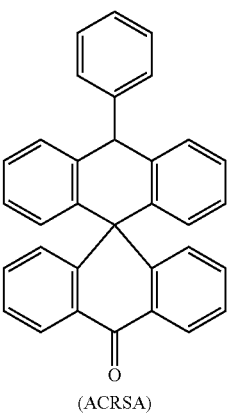

-continued

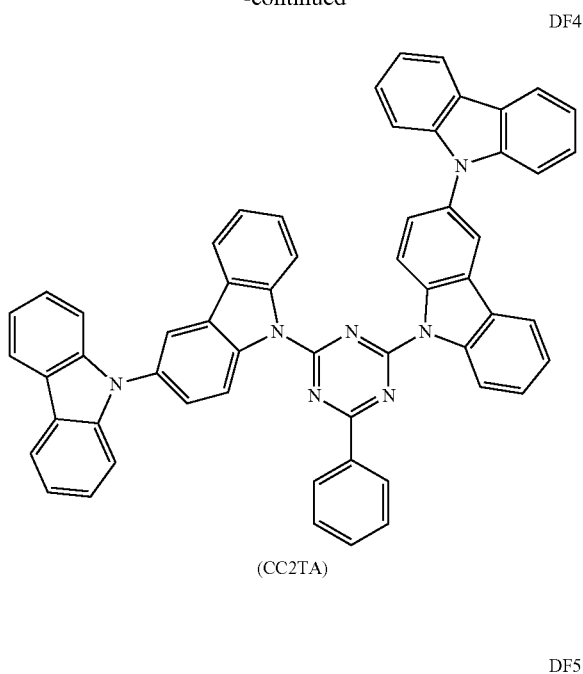

(CC2TA)

(PIC-TRZ)

(PIC-TRZ2)

-continued

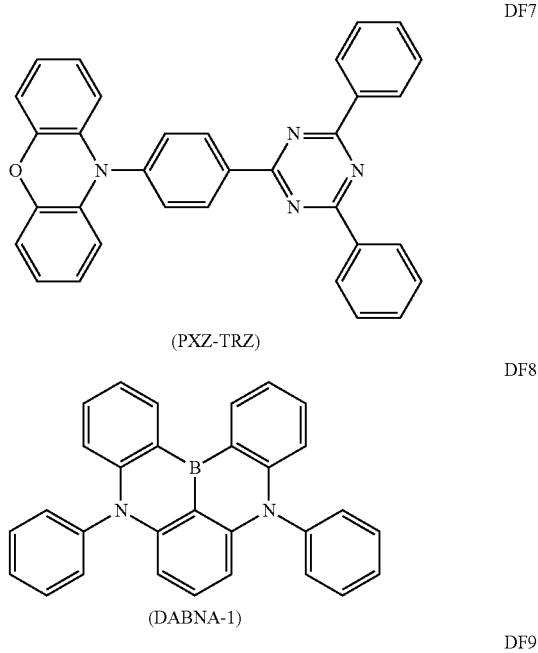

(PXZ-TRZ)

(DABNA-1)

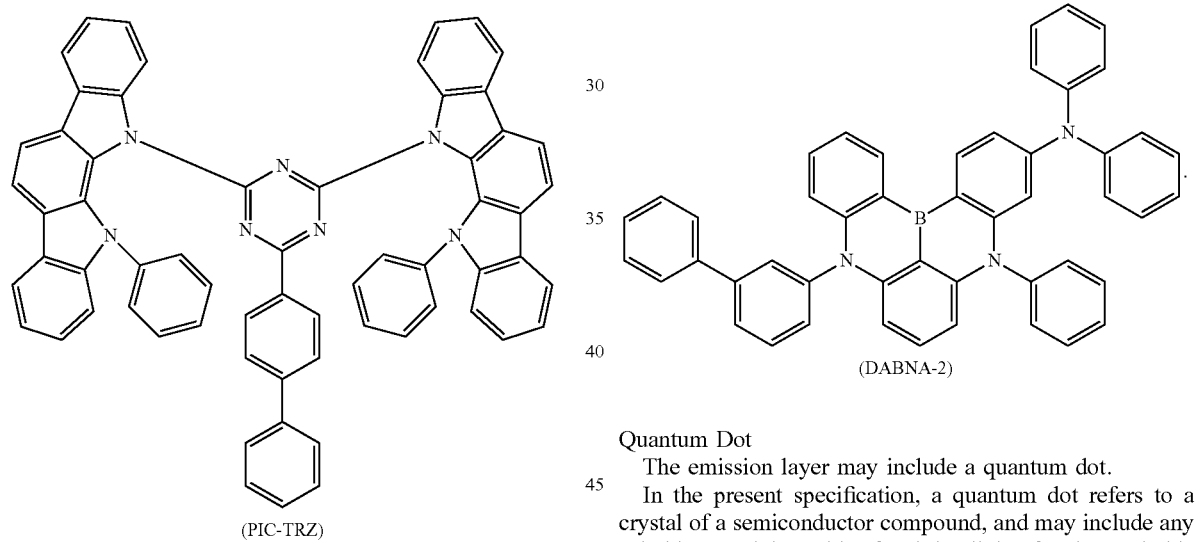

(DABNA-2)

Quantum Dot

The emission layer may include a quantum dot.

In the present specification, a quantum dot refers to a crystal of a semiconductor compound, and may include any suitable material capable of emitting light of various suitable emission wavelengths according to the size of the crystal.

A diameter of the quantum dot may be, for example, in a range of about 1 nm to about 10 nm.

The quantum dot may be synthesized by a wet chemical process, a metal organic chemical vapor deposition process, a molecular beam epitaxy process, and/or any suitable process similar thereto.

According to the wet chemical process, a precursor material is mixed with an organic solvent to grow a quantum dot particle crystal. When the crystal grows, the organic solvent naturally acts as a dispersant coordinated on the surface of the quantum dot crystal and controls the growth of the crystal so that the growth of quantum dot particles can be controlled through a process which is more easily performed than vapor deposition methods, such as metal organic chemical vapor deposition (MOCVD) or molecular beam epitaxy (MBE), and which requires low costs.

The quantum dot may include a Group III-VI semiconductor compound; a Group II-VI semiconductor compound;

a Group III-V semiconductor compound; a Group III-VI semiconductor compound; a Group I-III-VI semiconductor compound; a Group IV-VI semiconductor compound; a Group IV element or compound; or any combination thereof.

For example, the Group III-VI semiconductor compound may include a binary compound, such as $In_2S_3$; a ternary compound, such as AgInS, $AgInS_2$, CuInS, and/or $CuInS_2$; or any combination thereof.

Examples of the Group II-VI semiconductor compound include a binary compound, such as CdSe, CdTe, ZnS, ZnSe, ZnTe, ZnO, HgS, HgSe, HgTe, MgSe, and/or MgS; a ternary compound, such as CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, and/or MgZnS; a quaternary compound, such as CdZnSeS, CdZnSeTe, CdZnSTe, CdHgSeS, CdHgSeTe, CdHgSTe, HgZnSeS, HgZnSeTe, and/or HgZnSTe; or any combination thereof.

Examples of the Group III-V semiconductor compound include a binary compound, such as GaN, GaP, GaAs, GaSb, AlN, AlP, AlAs, AlSb, InN, InP, InAs, InSb, and/or the like; a ternary compound, such as GaNP, GaNAs, GaNSb, GaPAs, GaPSb, AlNP, AlNAs, AlNSb, AlPAs, AlPSb, InGaP, InNP, InAlP, InNAs, InNSb, InPAs, InPSb, GaAlNP, and/or the like; a quaternary compound, such as GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and/or the like; or any combination thereof. In some embodiments, the Group III-V semiconductor compound may further include Group II elements. Examples of the Group III-V semiconductor compound further including Group II elements include InZnP, InGaZnP, InAlZnP, etc.

Examples of the Groups III-VI semiconductor compound include a binary compound, such as GaS, GaSe, $Ga_2Se_3$, GaTe, InS, InSe, $In_2Se_3$, and/or InTe; a ternary compound, such as $InGaS_3$, and/or $InGaSe_3$; and any combination thereof.

Examples of the Group I-III-VI semiconductor compound include a ternary compound, such as AgInS, $AgInS_2$, CuInS, $CuInS_2$, $CuGaO_2$, $AgGaO_2$, and/or $AgAlO_2$; or any combination thereof.

Examples of the Group IV-VI semiconductor compound include a binary compound, such as SnS, SnSe, SnTe, PbS, PbSe, PbTe, and/or the like; a ternary compound, such as SnSeS, SnSeTe, SnSTe, PbSeS, PbSeTe, PbSTe, SnPbS, SnPbSe, SnPbTe, and/or the like; a quaternary compound, such as SnPbSSe, SnPbSeTe, SnPbSTe, and/or the like; or any combination thereof.

The Group IV element or compound may include a single element compound, such as Si or Ge; a binary compound, such as SiC and/or SiGe; or any combination thereof.

Each element included in a multi-element compound such as the binary compound, ternary compound and quaternary compound, may exist in a particle with a uniform concentration or non-uniform concentration.

In some embodiments, the quantum dot may have a single structure or a dual core-shell structure. In the case of the quantum dot having a single structure, the concentration of each element included in the corresponding quantum dot is uniform (e.g., substantially uniform). In an embodiment, the material contained in the core and the material contained in the shell may be different from each other.

The shell of the quantum dot may act as a protective layer to prevent or reduce chemical degeneration of the core to maintain semiconductor characteristics and/or as a charging layer to impart electrophoretic characteristics to the quantum dot. The shell may be a single layer or a multilayer. The interface between the core and the shell may have a concentration gradient that decreases along a direction toward the center of the element present in the shell.

Examples of the shell of the quantum dot may include an oxide of metal, or non-metal, a semiconductor compound, and any combination thereof. Examples of the oxide of metal or non-metal include a binary compound, such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and/or NiO; a ternary compound, such as $MgAl_2O_4$, $CoFe_2O_4$, $NiFe_2O_4$, and/or $CoMn_2O_4$; and any combination thereof. Examples of the semiconductor compound include, as described herein, Group III-VI semiconductor compounds; Group II-VI semiconductor compounds; Group III-V semiconductor compounds; Group III-VI semiconductor compounds; Group I-III-VI semiconductor compounds; Group IV-VI semiconductor compounds; and any combination thereof. In addition, the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, or any combination thereof.

A full width at half maximum (FWHM) of an emission wavelength spectrum of the quantum dot may be about 45 nm or less, for example, about 40 nm or less, for example, about 30 nm or less. In addition, because the light emitted through the quantum dot is emitted in all directions (e.g., substantially every direction), the wide viewing angle can be improved.

In addition, the quantum dot may be, for example, a spherical, pyramidal, multi-arm, and/or cubic nanoparticle, a nanotube, a nanowire, a nanofiber, and/or nanoplate particle.

Because the energy band gap can be adjusted by controlling the size of the quantum dot, light having various suitable wavelength bands can be obtained from the quantum dot emission layer. Therefore, by using quantum dots of different sizes, a light-emitting display that emits light of various suitable wavelengths may be implemented. In one embodiment, the size of the quantum dot may be selected from to emit red, green and/or blue light. In addition, the size of the quantum dot may be configured to emit white light by combining light of various suitable colors.

Electron Transport Region in Interlayer 130

The electron transport region may have: i) a single-layered structure including (e.g., consisting of) a single layer including (e.g., consisting of) a single material, ii) a single-layered structure including (e.g., consisting of) a single layer including (e.g., consisting of) a plurality of different materials, or iii) a multi-layered structure including a plurality of layers including different materials.

The electron transport region may include a buffer layer, a hole blocking layer, an electron control layer, an electron transport layer, an electron injection layer, or any combination thereof.

In an embodiment, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein, for each structure, constituting layers are sequentially stacked from an emission layer.

In an embodiment, the electron transport region (for example, the buffer layer, the hole blocking layer, the electron control layer, or the electron transport layer in the electron transport region) may include a metal-free compound including at least one π electron-deficient nitrogen-containing $C_1$-$C_{60}$ cyclic group.

In an embodiment, the electron transport region may include a compound represented by Formula 601 below:

$$[Ar_{601}]_{xe11}\text{-}[(L_{601})_{xe1}\text{-}R_{601}]_{xe21} \quad \text{Formula 601}$$

wherein, in Formula 601,

Ar$_{601}$ and L$_{601}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xe11 may be 1, 2, or 3, xe1 may be 0, 1, 2, 3, 4, or 5, R$_{601}$ may be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si(O$_{601}$)(O$_{602}$)(O$_{603}$), —C(=O)(Q$_{601}$), —S(=O)$_2$(Q$_{601}$), or —P(=O)(Q$_{601}$)(Q$_{602}$), Q$_{601}$ to Q$_{603}$ are the same as described in connection with Q$_1$, xe21 may be 1, 2, 3, 4, or 5, at least one selected from Ar$_{601}$, L$_{601}$ and R$_{601}$ may each independently be a π electron-deficient nitrogen-containing $C_1$-$C_{60}$ cyclic group unsubstituted or substituted with at least one $R_{10a}$.

For example, when xe11 in Formula 601 is 2 or more, two or more of Ar$_{601}$(S) may be linked via a single bond.

In an embodiment, Ar$_{601}$ in Formula 601 may be a substituted or unsubstituted anthracene group.

In an embodiment, the electron transport region may include a compound represented by Formula 601-1:

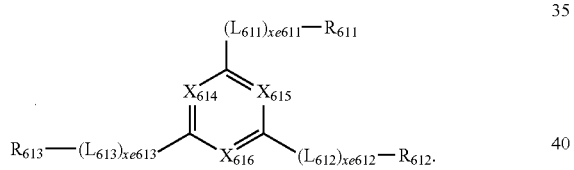

Formula 601-1

In Formula 601-1,

X$_{614}$ may be N or C(R$_{614}$), X$_{615}$ may be N or C(R$_{615}$), X$_{616}$ may be N or C(R$_{616}$), at least one selected from X$_{614}$ to X$_{616}$ may be N, L$_{611}$ to L$_{613}$ are the same as described in connection with L$_{601}$, xe611 to xe613 are the same as described in connection with xe1, R$_{611}$ to R$_{613}$ are the same as described in connection with R$_{601}$, R$_{614}$ to R$_{616}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group substituted or unsubstituted at least one $R_{10a}$.

For example, xe1 and xe611 to xe613 in Formulae 601 and 601-1 may each independently be 0, 1, or 2.

The electron transport region may include one selected from Compounds ET1 to ET45, 2,9-dimethyl-4,7-diphenyl-1,10-phenanthroline (BCP), 4,7-diphenyl-1,10-phenanthroline (Bphen), Alq$_3$, BAlq, TAZ, NTAZ, diphenyl(4-(triphenylsilyl)phenyl)-phosphine oxide (TSPO1), or any combination thereof:

ET1

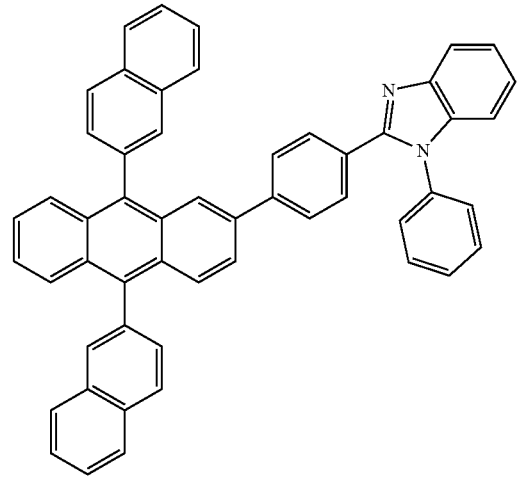

ET2

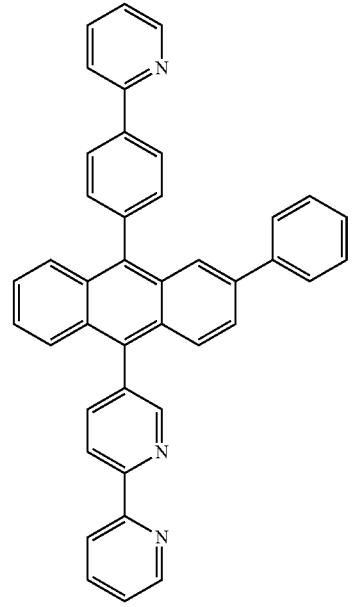

ET3

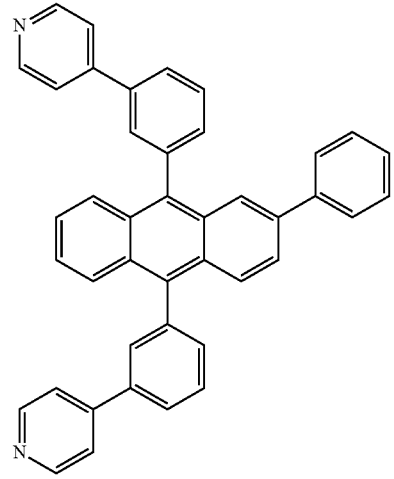

ET4
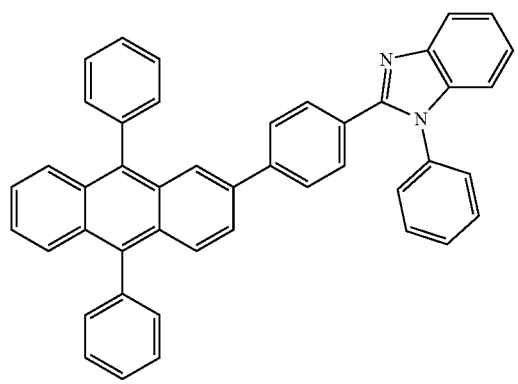
ET5
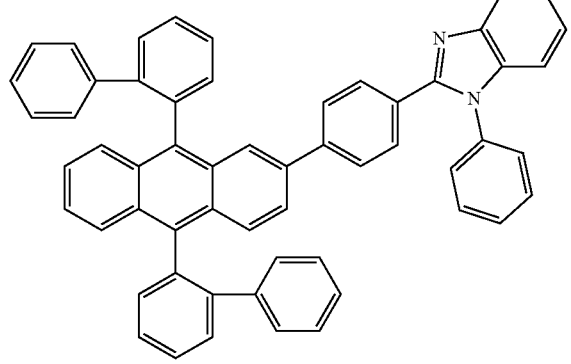
ET6
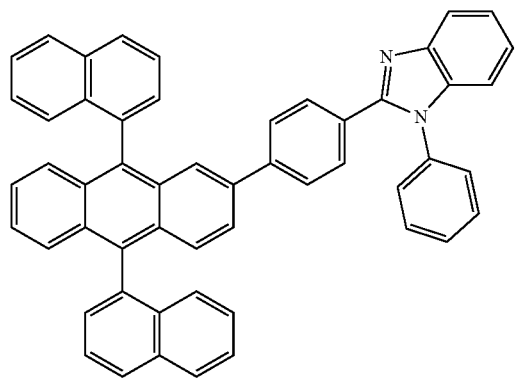
ET7
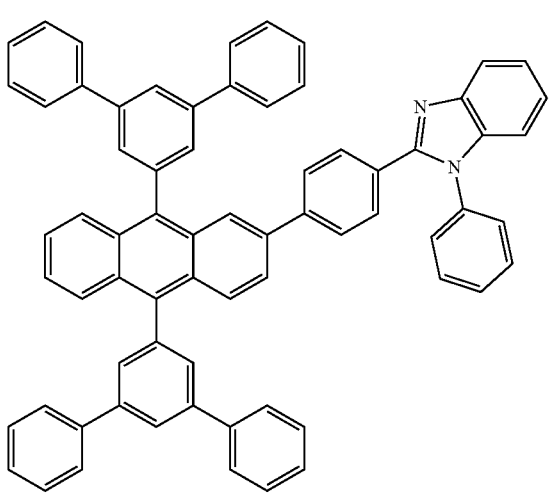
ET8
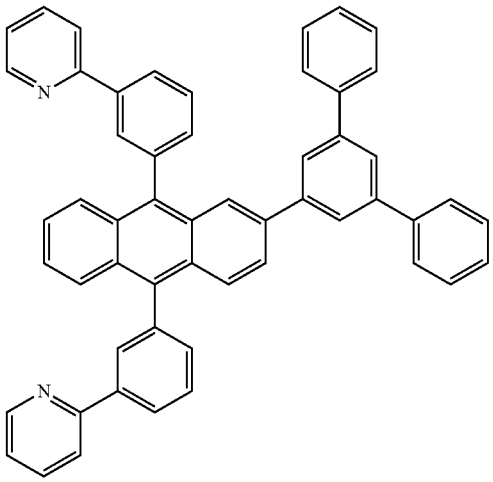
ET9
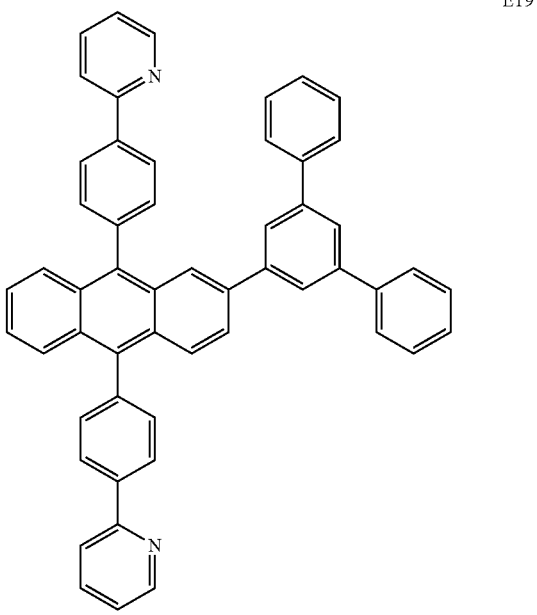

ET10
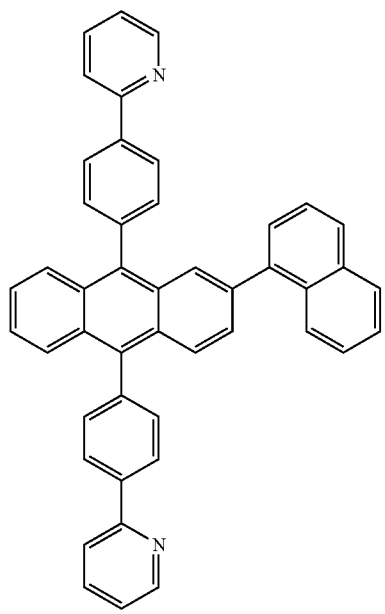
ET11
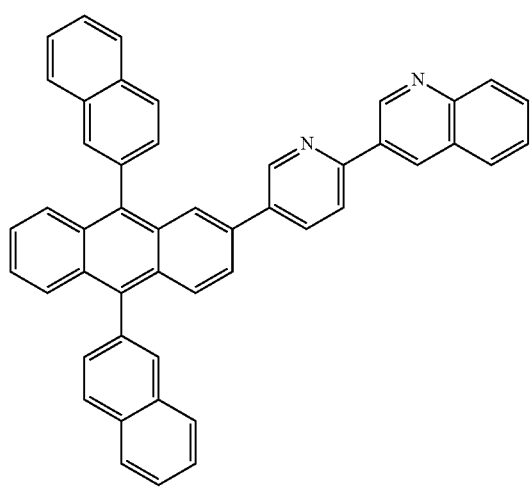
ET12
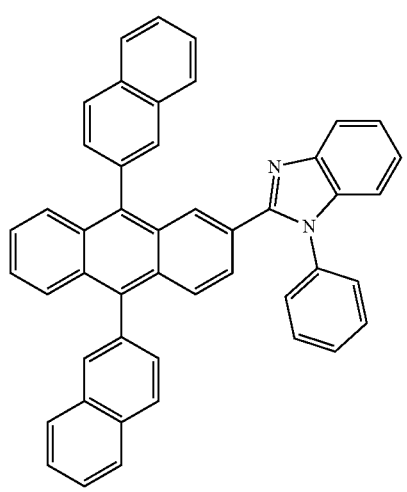
ET13
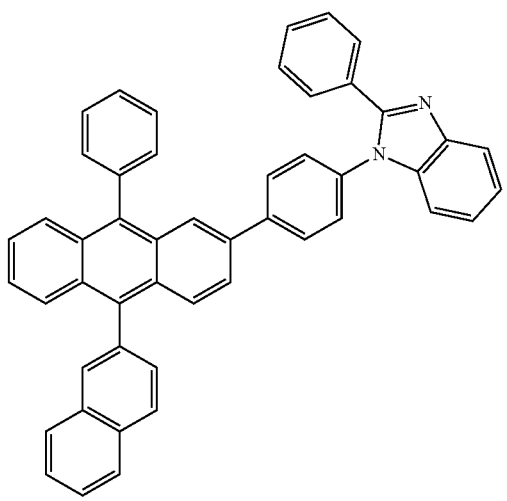
ET14
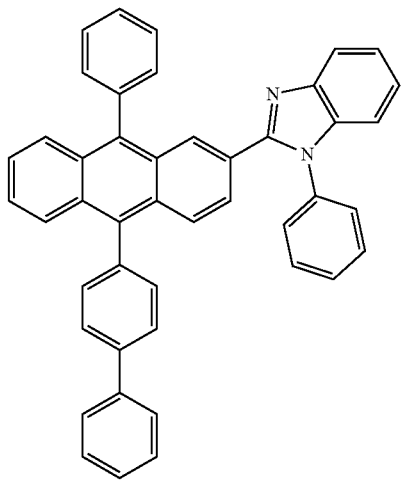
ET15
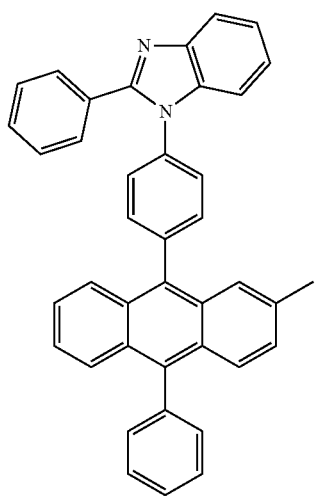

ET16
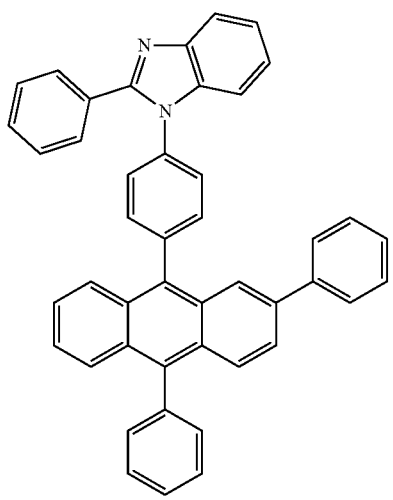
ET17
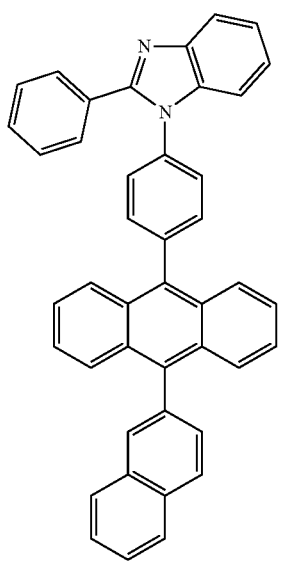
ET18
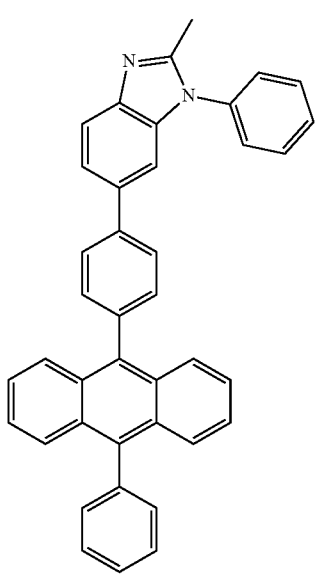
ET19
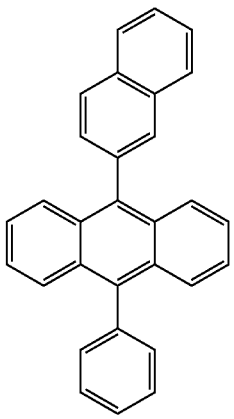
ET20
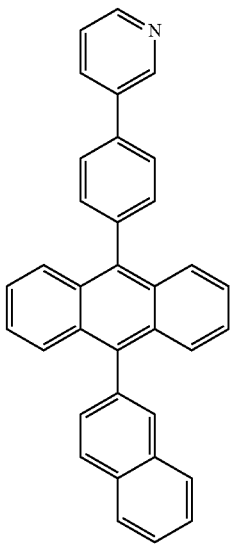
ET21
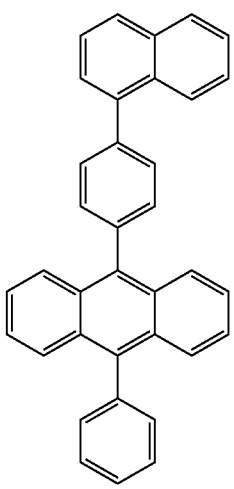

ET22
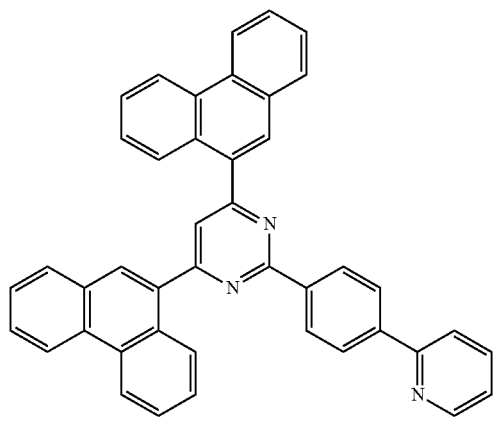
ET25
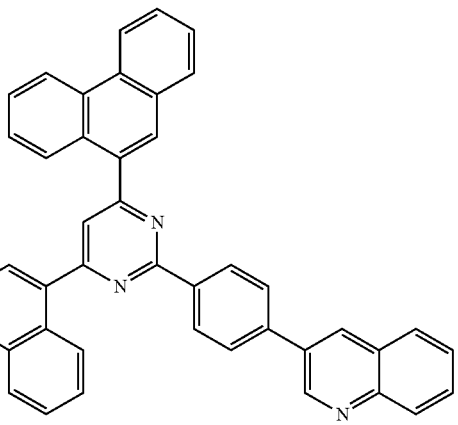
ET23
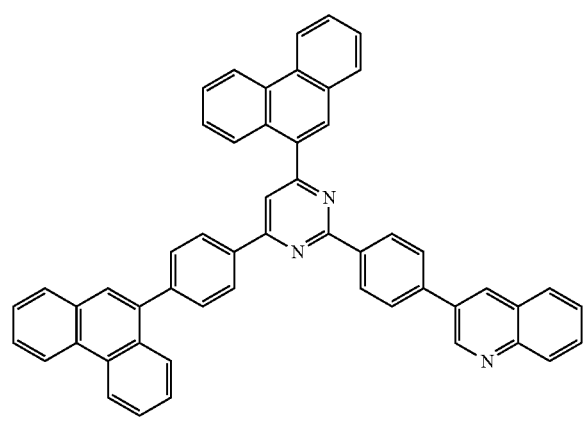
ET26
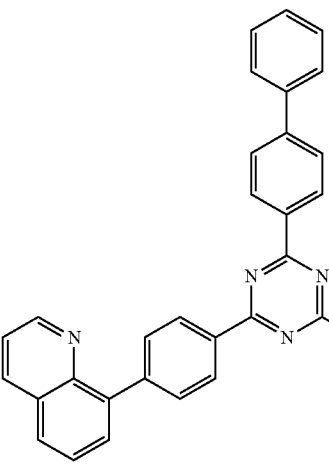
ET24
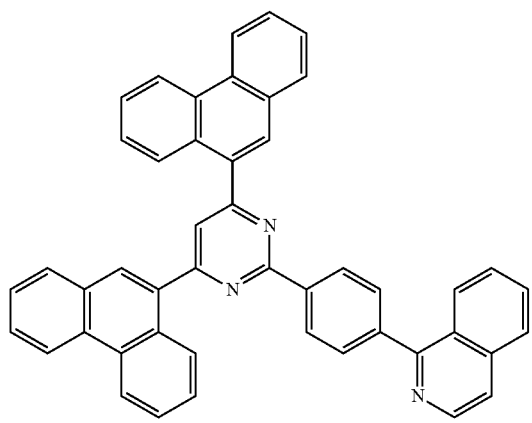
ET27
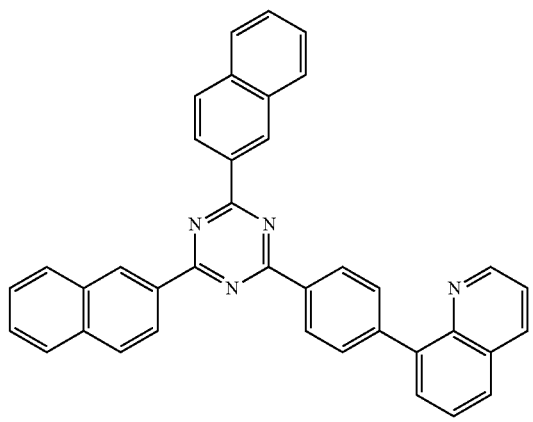

ET28
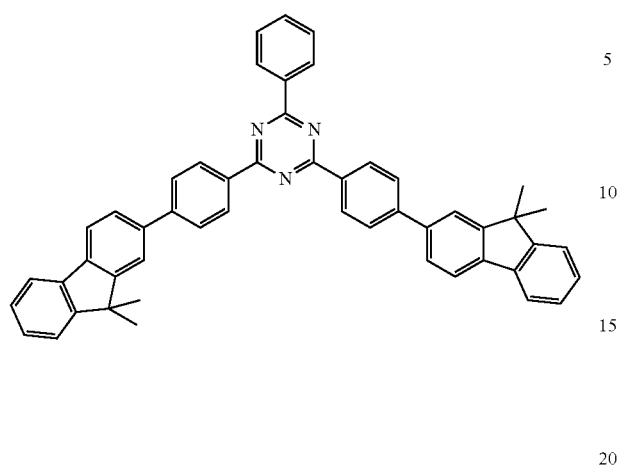
ET31
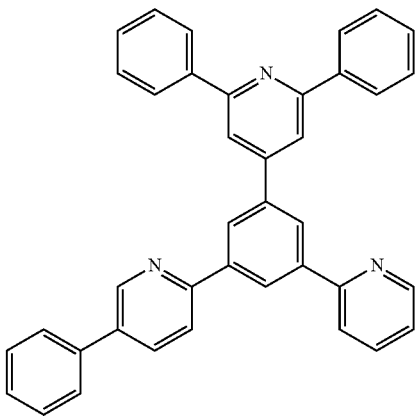
ET29
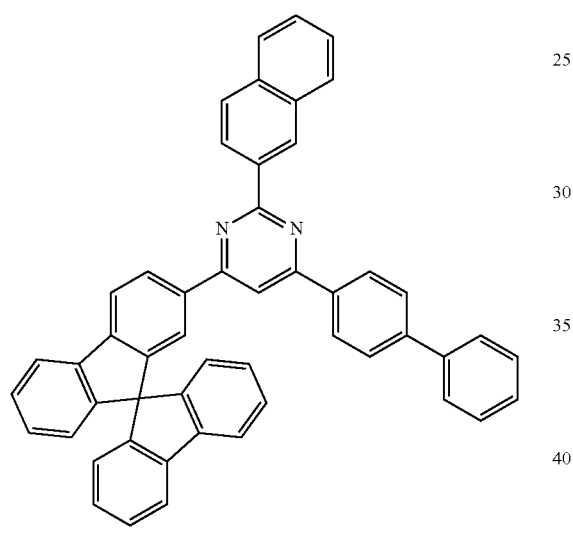
ET32
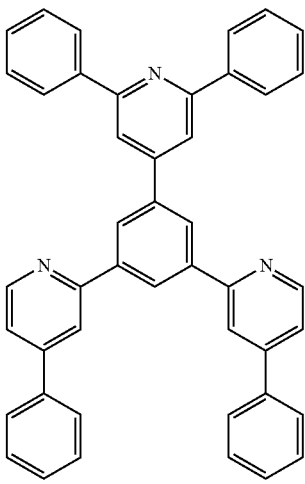
ET30
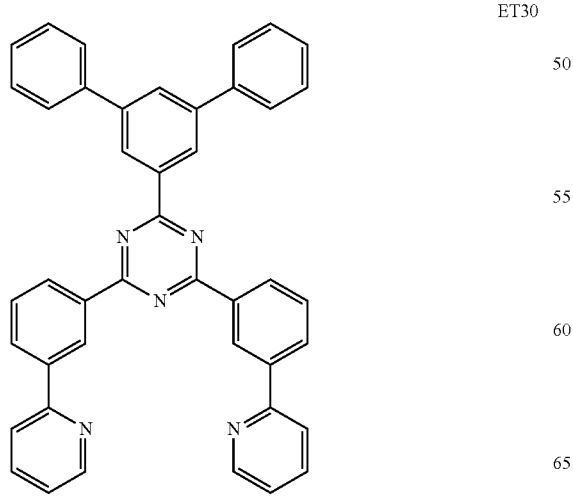
ET33
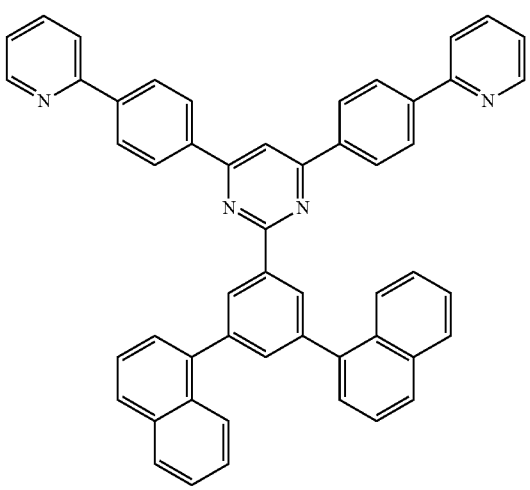

ET34
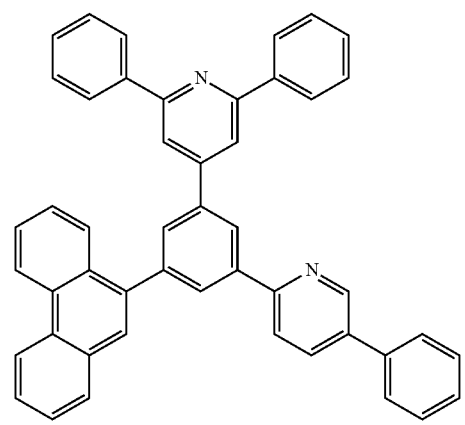
ET35
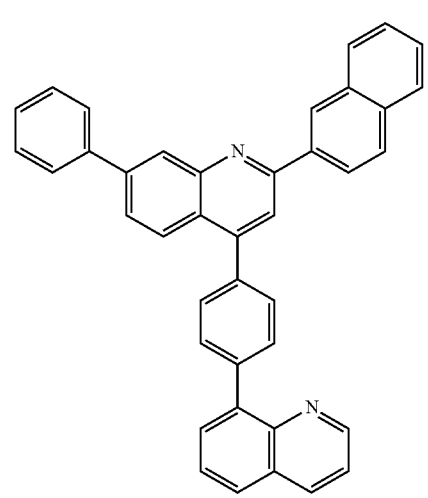
ET36
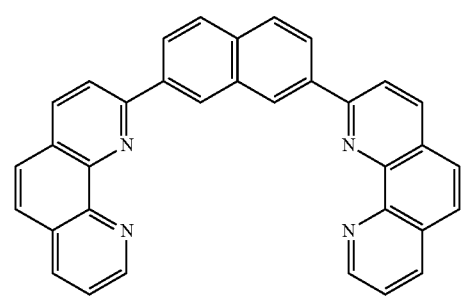
ET37
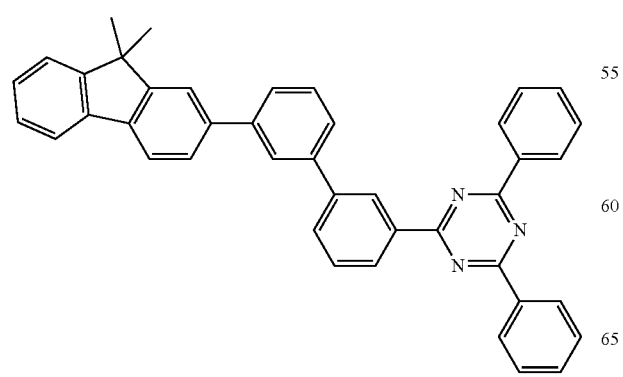
ET38
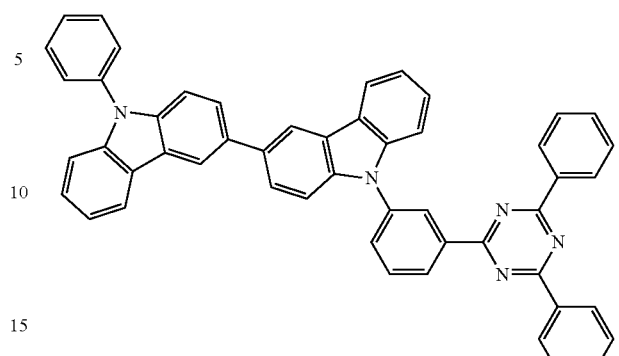
ET39
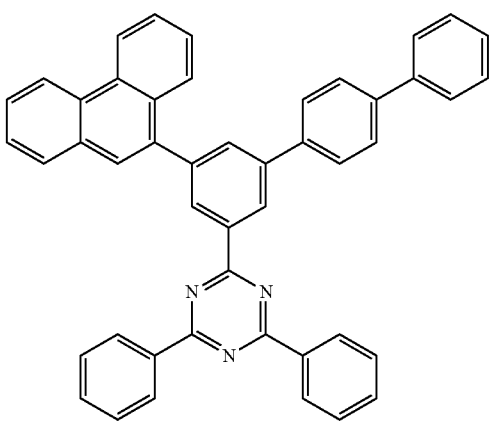
ET40
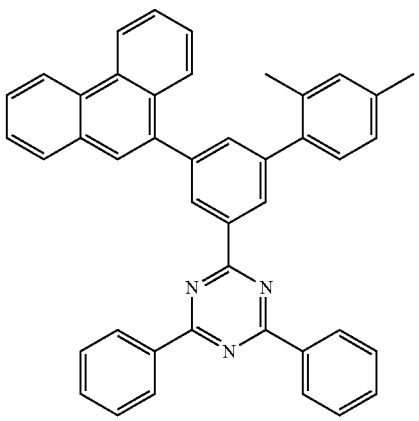

ET41
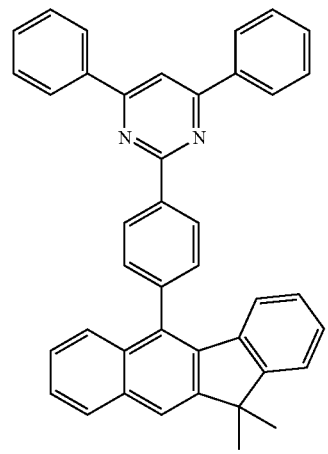
ET42
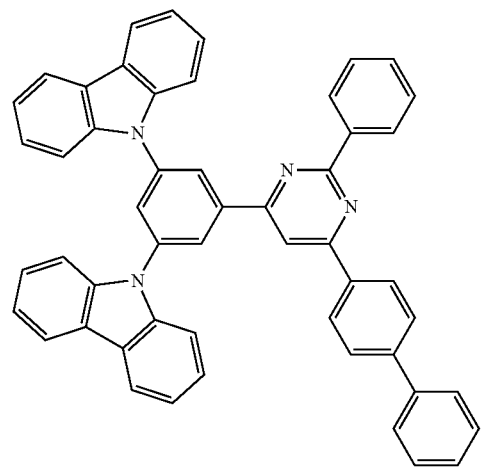
ET43
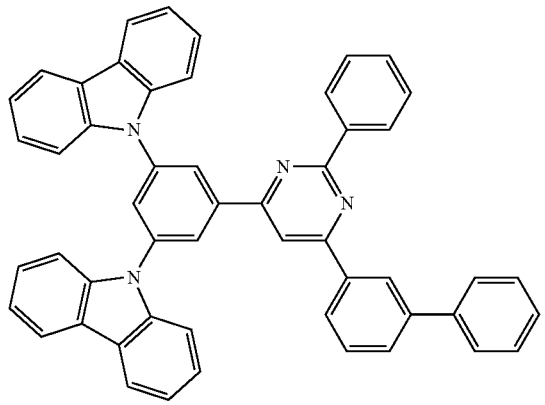
ET44
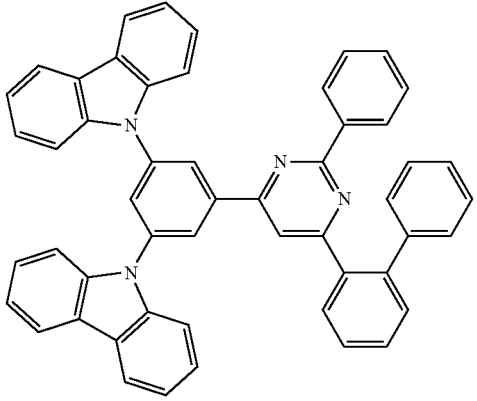
ET45
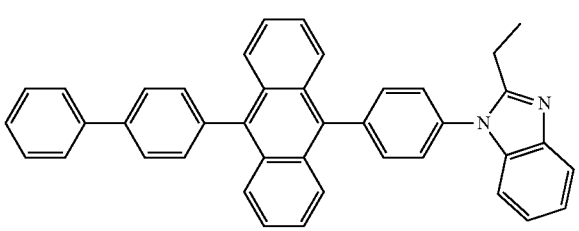
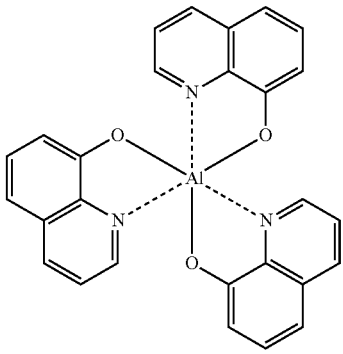
Alq3
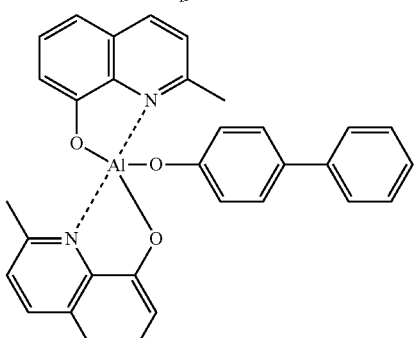
BAlq
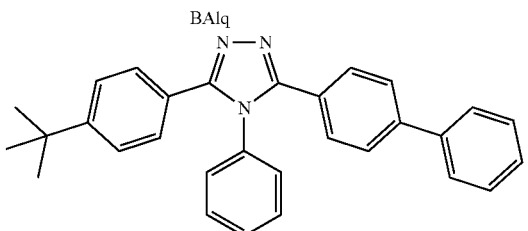
TAZ

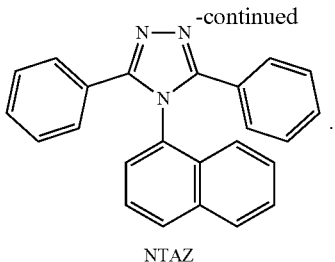

NTAZ

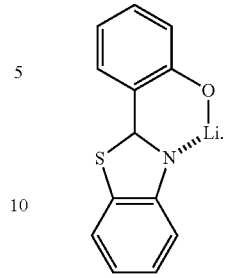

ET-D2

The thickness of the electron transport region may be from about 160 Å to about 5,000 Å, for example, from about 100 Å to about 4,000 Å. When the electron transport region includes a buffer layer, a hole blocking layer, an electron control layer, an electron transport layer, or any combination thereof, the thickness of the buffer layer, the hole blocking layer, or the electron control layer may each independently be from about 20 Å to about 1000 Å, for example, about 30 Å to about 300 Å, and the thickness of the electron transport layer may be from about 100 Å to about 1000 Å, for example, about 150 Å to about 500 Å. When the thicknesses of the buffer layer, hole blocking layer, electron control layer, electron transport layer and/or electron transport layer are within these ranges, suitable or satisfactory hole transporting characteristics may be obtained without a substantial increase in driving voltage.

The electron transport region (for example, the electron transport layer in the electron transport region) may further include, in addition to the materials described above, a metal-containing material.

The metal-containing material may include an alkali metal complex, alkaline earth metal complex, or any combination thereof. The metal ion of an alkali metal complex may be a Li ion, a Na ion, a K ion, a Rb ion, or a Cs ion, and the metal ion of alkaline earth metal complex may be a Be ion, a Mg ion, a Ca ion, a Sr ion, or a Ba ion. A ligand coordinated with the metal ion of the alkali metal complex or the alkaline earth-metal complex may include a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxydiphenyloxadiazole, a hydroxydiphenylthiadiazole, a hydroxyphenylpyridine, a hydroxyphenylbenzimidazole, a hydroxyphenylbenzothiazole, a bipyridine, a phenanthroline, a cyclopentadiene, or any combination thereof.

For example, the metal-containing material may include a Li complex. The Li complex may include, for example, Compound ET-D1 (LiQ) or ET-D2:

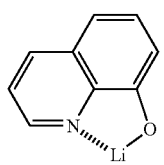

ET-D1

The electron transport region may include an electron injection layer that facilitates the injection of electrons from the second electrode 150. The electron injection layer may directly contact (e.g., physically contact) the second electrode 150.

The electron injection layer may have: i) a single-layered structure including (e.g., consisting of) a single layer including (e.g., consisting of) a single material, ii) a single-layered structure including (e.g., consisting of) a single layer including (e.g., consisting of) a plurality of different materials, or iii) a multi-layered structure including a plurality of layers including different materials.

The electron injection layer may include an alkali metal, alkaline earth metal, a rare earth metal, an alkali metal-containing compound, alkaline earth metal-containing compound, a rare earth metal-containing compound, an alkali metal complex, alkaline earth metal complex, a rare earth metal complex, or any combination thereof.

The alkali metal may include Li, Na, K, Rb, Cs, or any combination thereof. The alkaline earth metal may include Mg, Ca, Sr, Ba, or any combination thereof. The rare earth metal may include Sc, Y, Ce, Tb, Yb, Gd, or any combination thereof.

The alkali metal-containing compound, the alkaline earth metal-containing compound, and the rare earth metal-containing compound may be oxides, halides (for example, fluorides, chlorides, bromides, and/or iodides), and/or tellurides of the alkali metal, the alkaline earth metal, and the rare earth metal, or any combination thereof.

The alkali metal-containing compound may include alkali metal oxides, such as $Li_2O$, $Cs_2O$, and/or $K_2O$, alkali metal halides, such as LiF, NaF, CsF, KF, LiI, NaI, CsI, and/or KI, or any combination thereof. The alkaline earth metal-containing compound may include an alkaline earth metal compound, such as BaO, SrO, CaO, $Ba_xSr_{1-x}O$ (x is a real number satisfying the condition of 0<x<1), $Ba_xCa_{1-x}O$ (x is a real number satisfying the condition of 0<x<1), and/or the like. The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. In an embodiment, the rare earth metal-containing compound may include lanthanide metal telluride. Examples of the lanthanide metal telluride include LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, and $Lu_2Te_3$.

The alkali metal complex, the alkaline earth-metal complex, and the rare earth metal complex may include i) one selected from ions of the alkali metal, the alkaline earth metal, and the rare earth metal and ii), as a ligand bonded to the metal ion, for example, hydroxyquinoline, hydroxyisoquinoline, hydroxybenzoquinoline, hydroxyacridine, hydroxyphenanthridine, hydroxyphenyloxazole, hydroxyphenylthiazole, hydroxydiphenyloxadiazole, hydroxydiphenylthiadiazole, hydroxyphenylpyridine, hydroxyphenyl benzimidazole, hydroxyphenylbenzothiazole, bipyridine, phenanthroline, cyclopentadiene, or any combination thereof.

The electron injection layer may include (e.g., consist of) an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof, as described above. In an embodiment, the electron injection layer may further include an organic material (for example, a compound represented by Formula 601).

In an embodiment, the electron injection layer may include (e.g., consist of) i) an alkali metal-containing compound (for example, an alkali metal halide), ii) a) an alkali metal-containing compound (for example, an alkali metal halide); and b) an alkali metal, an alkaline earth metal, a rare earth metal, or any combination thereof. In an embodiment, the electron injection layer may be a KI:Yb co-deposited layer, an RbI:Yb co-deposited layer, and/or the like.

When the electron injection layer further includes an organic material, alkali metal, alkaline earth metal, rare earth metal, an alkali metal-containing compound, an alkaline earth metal-containing compound, a rare earth metal-containing compound, alkali metal complex, alkaline earth-metal complex, rare earth metal complex, or any combination thereof may be homogeneously or non-homogeneously dispersed in a matrix including the organic material.

A thickness of the electron injection layer may be in a range of about 1 Å to about 100 Å, and, for example, about 3 Å to about 90 Å. When the thickness of the electron injection layer is within the range described above, the electron injection layer may have suitable or satisfactory electron injection characteristics without a substantial increase in driving voltage.

Second Electrode 150

The second electrode 150 may be on the interlayer 130 having such a structure. The second electrode 150 may be a cathode, which is an electron injection electrode, and as the material for the second electrode 150, a metal, an alloy, an electrically conductive compound, or any combination thereof, each having a low work function, may be used.

In an embodiment, the second electrode 150 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), ITO, IZO, or a combination thereof. The second electrode 150 may be a transmissive electrode, a semi-transmissive electrode, or a reflective electrode.

The second electrode 150 may have a single-layered structure or a multi-layered structure including two or more layers.

Capping Layer

A first capping layer may be outside the first electrode 110, and/or a second capping layer may be outside the second electrode 150. In more detail, the light-emitting device 10 may have a structure in which the first capping layer, the first electrode 110, the interlayer 130, and the second electrode 150 are sequentially stacked in this stated order, a structure in which the first electrode 110, the interlayer 130, the second electrode 150, and the second capping layer are sequentially stacked in this stated order, or a structure in which the first capping layer, the first electrode 110, the interlayer 130, the second electrode 150, and the second capping layer are sequentially stacked in this stated order.

Light generated in an emission layer of the interlayer 130 of the light-emitting device 10 may be extracted toward the outside through the first electrode 110, which is a semi-transmissive electrode or a transmissive electrode, and the first capping layer or light generated in an emission layer of the interlayer 130 of the light-emitting device 10 may be extracted toward the outside through the second electrode 150, which is a semi-transmissive electrode or a transmissive electrode, and the second capping layer.

The first capping layer and the second capping layer may increase external luminescence efficiency according to the principle of constructive interference. Accordingly, the light extraction efficiency of the light-emitting device 10 is increased, so that the luminescence efficiency of the light-emitting device 10 may be improved.

Each of the first capping layer and second capping layer may include a material having a refractive index (at a wavelength of 589 nm) of 1.6 or more.

The first capping layer and the second capping layer may each independently be an organic capping layer including an organic material, an inorganic capping layer including an inorganic material, or a composite capping layer including an organic material and an inorganic material.

At least one selected from the first capping layer and the second capping layer may each independently include carbocyclic compounds, heterocyclic compounds, an amine group-containing compounds, porphyrine derivatives, phthalocyanine derivatives, a naphthalocyanine derivatives, alkali metal complexes, alkaline earth-based complexes, or any combination thereof. The carbocyclic compound, the heterocyclic compound, and the amine group-containing compound may be optionally substituted with a substituent containing O, N, S, Se, Si, F, Cl, Br, I, or any combination thereof.

In an embodiment, at least one selected from the first capping layer and the second capping layer may each independently include an amine group-containing compound.

In an embodiment, at least one selected from the first capping layer and the second capping layer may each independently include a compound represented by Formula 201, a compound represented by Formula 202, or any combination thereof.

In one or more embodiments, at least one selected from the first capping layer and the second capping layer may each independently include a compound selected from Compounds HT28 to HT33, Compounds CP1 to CP6, β-NPB, or any combination thereof, but embodiments of the present disclosure are not limited thereto:

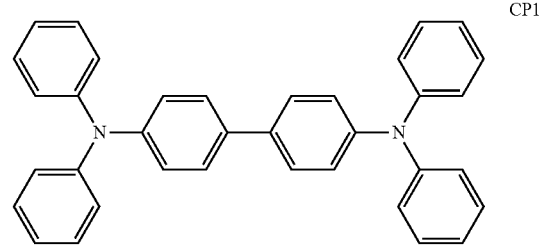

CP1

CP2

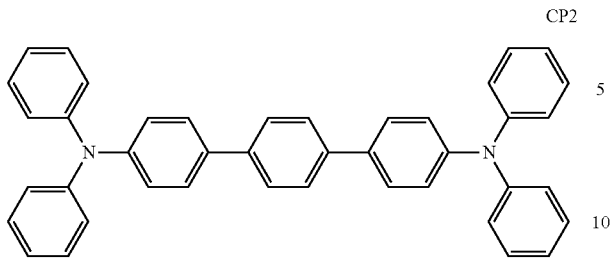

CP3

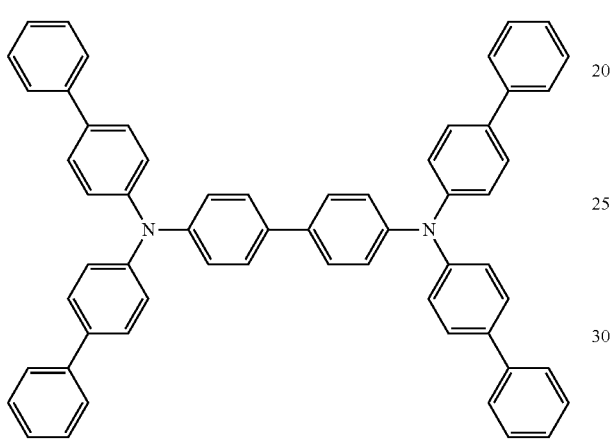

CP4

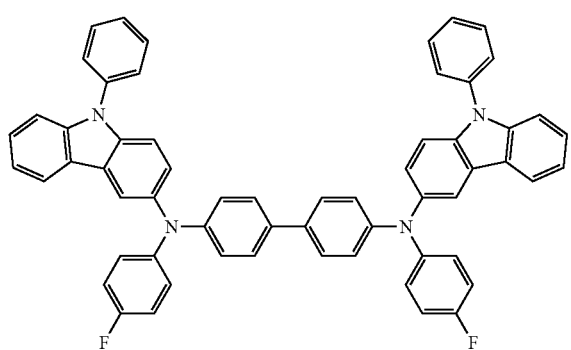

CP5

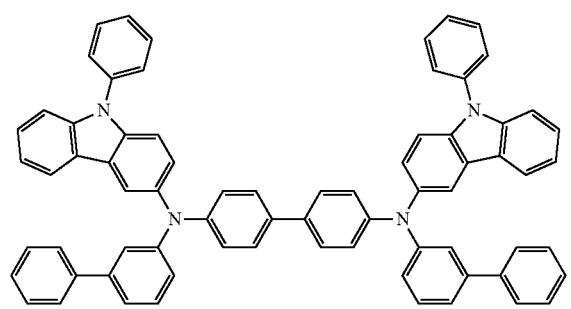

CP6

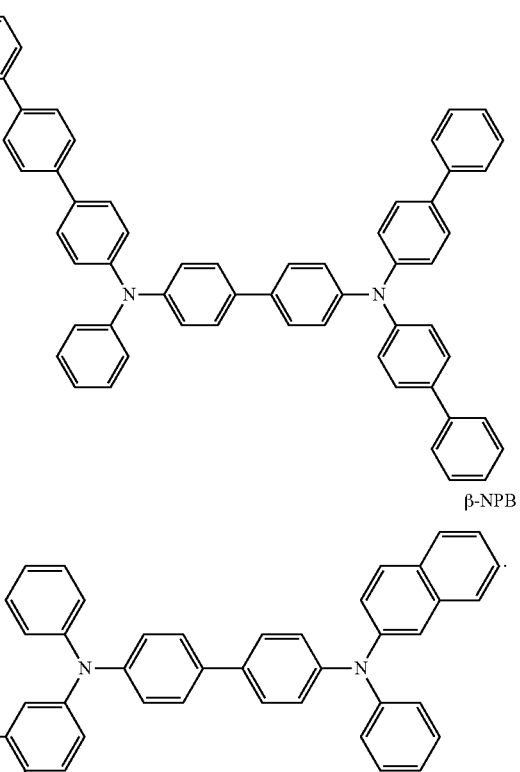

β-NPB

Electronic Apparatus

The light-emitting device may be included in various suitable electronic apparatuses. In an embodiment, the electronic apparatus including the light-emitting device may be a light-emitting apparatus, an authentication apparatus, and/or the like.

The electronic apparatus (for example, light-emitting apparatus) may further include, in addition to the light-emitting device, i) a color filter, ii) a color conversion layer, or iii) a color filter and a color conversion layer. The color filter and/or the color conversion layer may be in at least one traveling direction of light emitted from the light-emitting device. In an embodiment, the light emitted from the light-emitting device may be blue light or white light. The light-emitting device may be the same as described above. In an embodiment, the color conversion layer may include quantum dots.

The electronic apparatus may include a first substrate. The first substrate may include a plurality of subpixel areas, the color filter may include a plurality of color filter areas respectively corresponding to the subpixel areas, and the color conversion layer may include a plurality of color conversion areas respectively corresponding to the subpixel areas.

A pixel-defining film may be located among the subpixel areas to define each of the subpixel areas.

The color filter may further include a plurality of color filter areas and light-blocking patterns located among the color filter areas, and the color conversion layer may include a plurality of color conversion areas and light-blocking patterns located among the color conversion areas.

The color filter areas (or the color conversion areas) may include a first area emitting first color light, a second area emitting second color light, and/or a third area emitting third color light, and the first color light, the second color light, and/or the third color light may have different maximum emission wavelengths from one another. In an embodiment, the first color light may be red light, the second color light may be green light, and the third color light may be blue light. In an embodiment, the color filter areas (or the color conversion areas) may include quantum dots. In more detail, the first area may include a red quantum dot, the second area may include a green quantum dot, and the third area may not include a quantum dot. The quantum dot is the same as described elsewhere in the present specification. The first area, the second area, and/or the third area may each include a scatterer.

In an embodiment, the light-emitting device may emit a first light, the first area may absorb the first light to emit a first first-color light, the second area may absorb the first light to emit a second first-color light, and the third area may absorb the first light to emit a third first-color light. In this regard, the first first-color light, the second first-color light, and the third-first light may have different maximum emission wavelengths from one another. In more detail, the first light may be blue light, the first first-color light may be red light, the second first-color light may be green light, and the third first-color light may be blue light.

The electronic apparatus may further include a thin-film transistor in addition to the light-emitting device 1 as described above. The thin-film transistor may include a source electrode, a drain electrode, and an activation layer, wherein any one selected from the source electrode and the drain electrode may be electrically coupled to any one selected from the first electrode and the second electrode of the light-emitting device.

The thin-film transistor may include a gate electrode, a gate insulating film, etc.

The activation layer may include crystalline silicon, amorphous silicon, organic semiconductor, oxide semiconductor, and/or the like.

The electronic apparatus may further include a sealing portion that seals the light-emitting device. The sealing portion and/or the color conversion layer may be placed between the color filter and the light-emitting device. The sealing portion allows light from the light-emitting device to be extracted to the outside, while concurrently (e.g., simultaneously) preventing or reducing penetration of ambient air and moisture into the light-emitting device. The sealing portion may be a sealing substrate including a transparent glass and/or a plastic substrate. The sealing portion may be a thin-film encapsulation layer including at least one layer of an organic layer and/or an inorganic layer. When the sealing portion is a thin film encapsulation layer, the electronic apparatus may be flexible.

Various suitable functional layers may be additionally on the sealing portion, in addition to the color filter and/or the color conversion layer, according to the use of the electronic apparatus. The functional layers may include a touch screen layer, a polarizing layer, and/or the like. The touch screen layer may be a pressure-sensitive touch screen layer, a capacitive touch screen layer, and/or an infra-red touch screen layer. The authentication apparatus may be, for example, a biometric authentication apparatus that authenticates an individual by using biometric information of a living body (for example, fingertips, pupils, etc.).

The authentication apparatus may further include, in addition to the light-emitting device, a biometric information collector.

The electronic apparatus may be applied to various suitable displays, light sources, lighting, personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram displays, ultrasonic diagnostic devices, and/or endoscope displays), fish finders, various suitable measuring instruments, meters (for example, meters for a vehicle, an aircraft, and/or a vessel), projectors, and/or the like.

Figure 2:
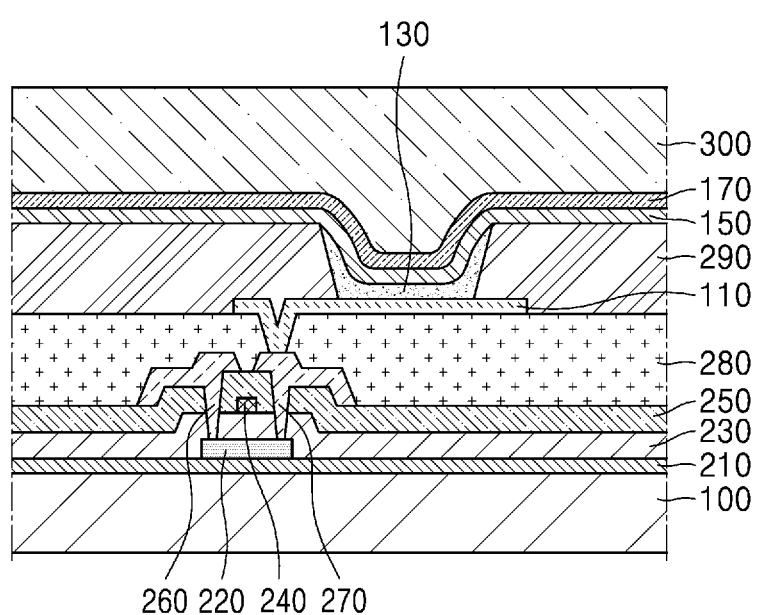
FIG. 2 is a schematic view of an electronic apparatus according to an embodiment.
Figure 3:
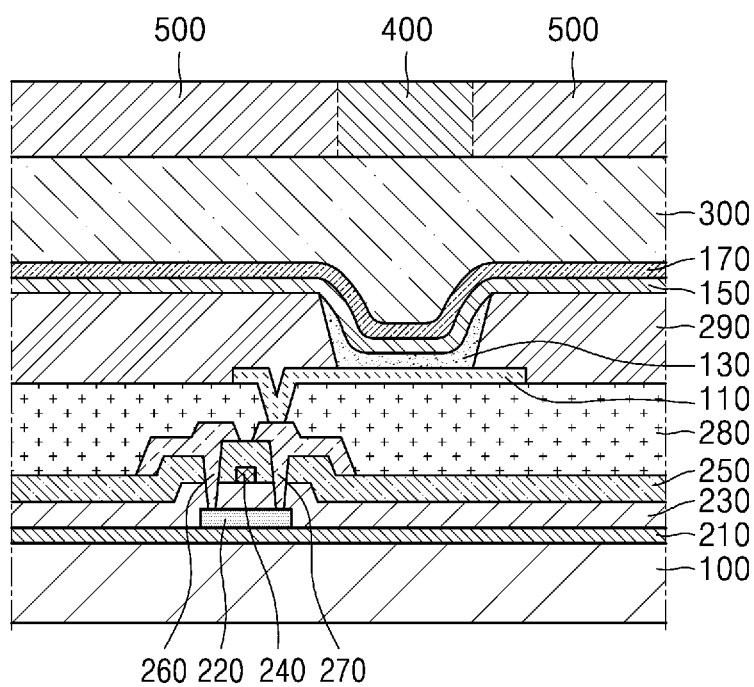
FIG. 3 is a schematic view of an electronic apparatus according to an embodiment.

Description of FIGS. 2 and 3

FIG. 2 is a cross-sectional view showing a light-emitting apparatus according to an embodiment of the present disclosure.

The light-emitting apparatus of FIG. 2 includes a substrate 100, a thin-film transistor (TFT), a light-emitting device, and an encapsulation portion 300 that seals the light-emitting device.

The substrate 100 may be a flexible substrate, a glass substrate, and/or a metal substrate. A buffer layer 210 may be formed on the substrate 100. The buffer layer 210 may prevent or reduce penetration of impurities through the substrate 100 and may provide a flat surface on the substrate 100.

A TFT may be on the buffer layer 210. The TFT may include an activation layer 220, a gate electrode 240, a source electrode 260, and a drain electrode 270.

The activation layer 220 may include an inorganic semiconductor such as silicon or polysilicon, an organic semiconductor, and/or an oxide semiconductor, and may include a source region, a drain region and a channel region.

A gate insulating film 230 for insulating the activation layer 220 from the gate electrode 240 may be on the activation layer 220, and the gate electrode 240 may be on the gate insulating film 230.

An interlayer insulating film 250 is on the gate electrode 240. The interlayer insulating film 250 may be placed between the gate electrode 240 and the source electrode 260 to insulate the gate electrode 240 from the source electrode 260 and between the gate electrode 240 and the drain electrode 270 to insulate the gate electrode 240 from the drain electrode 270.

The source electrode 260 and the drain electrode 270 may be on the interlayer insulating film 250. The interlayer insulating film 250 and the gate insulating film 230 may be formed to expose the source region and the drain region of the activation layer 220, and the source electrode 260 and the drain electrode 270 may be in contact (e.g., physical contact) with the exposed portions of the source region and the drain region of the activation layer 220.

The TFT is electrically coupled to a light-emitting device to drive the light-emitting device, and is covered by a passivation layer 280. The passivation layer 280 may include an inorganic insulating film, an organic insulating film, or a combination thereof. A light-emitting device is provided on the passivation layer 280. The light-emitting device may include a first electrode 110, an interlayer 130, and a second electrode 150.

The first electrode 110 may be formed on the passivation layer 280. The passivation layer 280 does not completely cover the drain electrode 270 and exposes a portion of the drain electrode 270, and the first electrode 110 is coupled to the exposed portion of the drain electrode 270.

A pixel defining layer 290 containing an insulating material may be on the first electrode 110. The pixel defining layer 290 exposes a region of the first electrode 110, and an interlayer 130 may be formed in the exposed region of the first electrode 110. The pixel defining layer 290 may be a polyimide and/or polyacrylic organic film. In some embodiments, at least some layers of the interlayer 130 may extend beyond the upper portion of the pixel defining layer 290 to be located in the form of a common layer.

The second electrode 150 may be on the interlayer 130, and a capping layer 170 may be additionally formed on the second electrode 150. The capping layer 170 may cover the second electrode 150.

The encapsulation portion 300 may be on the capping layer 170. The encapsulation portion 300 may be on a light-emitting device to protect the light-emitting device from moisture and/or oxygen. The encapsulation portion 300 may include: an inorganic film including silicon nitride (SiNx), silicon oxide (SiOx), indium tin oxide, indium zinc oxide, or any combination thereof; an organic film including polyethylene terephthalate, polyethylene naphthalate, polycarbonate, polyimide, polyethylene sulfonate, polyoxymethylene, polyarylate, hexamethyldisiloxane, an acrylic resin (for example, polymethyl methacrylate, polyacrylic acid, and/or the like), an epoxy-based resin (for example, aliphatic glycidyl ether (AGE), and/or the like), or a combination thereof; or a combination of the inorganic film and the organic film.

FIG. 3 shows a cross-sectional view showing a light-emitting apparatus according to an embodiment of the present disclosure.

The light-emitting apparatus of FIG. 3 is the same as the light-emitting apparatus of FIG. 2, except that a light-blocking pattern 500 and a functional region 400 are additionally on the encapsulation portion 300. The functional region 400 may be a combination of i) a color filter area, ii) a color conversion area, or iii) a combination of the color filter area and the color conversion area. In an embodiment, the light-emitting device included in the light-emitting apparatus of FIG. 3 may be a tandem light-emitting device.

Manufacturing Method

Respective layers included in the hole transport region, the emission layer, and respective layers included in the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec, depending on a material to be included in a layer to be formed and the structure of a layer to be formed.

Definition of at Least Some of the Terms

The term "$C_3$-$C_{60}$ carbocyclic group," as used herein, refers to a cyclic group consisting of carbon only and having three to sixty carbon atoms, and the term "$C_1$-$C_{60}$ heterocyclic group," as used herein, refers to a cyclic group that has one to sixty carbon atoms and further has, in addition to carbon, a heteroatom. The $C_3$-$C_{60}$ carbocyclic group and the $C_1$-$C_{60}$ heterocyclic group may each be a monocyclic group consisting of one ring or a polycyclic group in which two or more rings are condensed with each other (e.g., combined together with each other). For example, the number of ring-forming atoms of the $C_1$-$C_{60}$ heterocyclic group may be from 3 to 61.

The term "cyclic group," as used herein, may include the $C_3$-$C_{60}$ carbocyclic group, and the $C_1$-$C_{60}$ heterocyclic group.

The term "π electron-rich $C_3$-$C_{60}$ cyclic group," as used herein, refers to a cyclic group that has three to sixty carbon atoms and does not include *—N=*' as a ring-forming moiety, and the term "π electron-deficient nitrogen-containing $C_1$-$C_{60}$ cyclic group," as used herein, refers to a heterocyclic group that has one to sixty carbon atoms and includes *—N=*' as a ring-forming moiety.

For example,
the $C_3$-$C_{60}$ carbocyclic group may be i) group T1 or ii) a condensed cyclic group in which two or more groups T1 are condensed with (e.g., combined together with) each other (for example, a cyclopentadiene group, an adamantane group, a norbornane group, a benzene group, a pentalene group, a naphthalene group, an azulene group, an indacene group, acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indeno phenanthrene group, or an indenoanthracene group),
the $C_1$-$C_{60}$ heterocyclic group may be i) group T2, ii) a condensed cyclic group in which two or more groups T2 are condensed with (e.g., combined together with) each other, or iii) a condensed cyclic group in which at least one group T2 and at least one group T1 are condensed with (e.g., combined together with) each other (for example, a pyrrole group, a thiophene group, a furan group, an indole group, a benzoindole group, a naphthon indole group, an isoindole group, a benzoisoindole group, a naphthon isoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.), the π electron-rich $C_3$-$C_{60}$ cyclic group may be i) group T1, ii) a condensed cyclic group in which two or more groups T1 are condensed with (e.g., combined together with) each other, iii) group T3, iv) a condensed cyclic group in which two or more groups T3 are condensed with (e.g., combined together with) each other, or v) a condensed cyclic group in which at least one group T3 and at least one group T1 are condensed with (e.g., combined together with) each other (for example, the $C_3$-$C_{60}$ carbocyclic group, a pyrrole group, a thiophene group, a furan group, an indole group, a benzoindole group, a naphthon indole group, an isoindole group, a benzoisoindole group, a naphthon isoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, etc.), the π electron-deficient nitrogen-containing $C_1$-$C_{60}$ cyclic group may be i) group T4, ii) a condensed cyclic group in which two or more group T4 are condensed with (e.g., combined together with) each other, iii) a condensed cyclic group in which at least one group T4 and at least one group T1 are condensed with (e.g., combined together with) each other, iv) a condensed cyclic group in which at least one group T4 and at least one group T3 are condensed with (e.g., combined together with) each other, or v) a condensed cyclic group in which at least one group T4, at least one group T1, and at least one group T3 are condensed with (e.g., combined together with) one another (for example, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.), group T1 may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane (or a bicyclo[2.2.1]heptane) group, a norbornene group, a bicyclo[1.1.1]pentane group, a bicyclo[2.1.1]hexane group, a bicyclo[2.2.2]octane group, or a benzene group, group T2 may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group, group T3 may be a furan group, a thiophene group, a 1H-pyrrole group, a silole group, or a borole group, and group T4 may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The terms "the cyclic group," "the $C_3$-$C_{60}$ carbocyclic group," "the $C_1$-$C_{60}$ heterocyclic group," "the π electron-rich $C_3$-$C_{60}$ cyclic group," and "the π electron-deficient nitrogen-containing $C_1$-$C_{60}$ cyclic group," as used herein, refer to a group condensed to (e.g., combined together with) any cyclic group or a polyvalent group (for example, a divalent group, a trivalent group, a tetravalent group, etc.), depending on the structure of a formula in connection with which the terms are used. In an embodiment, "a benzene group" may be a benzo group, a phenyl group, a phenylene group, and/or the like, which may be easily understand by one of ordinary skill in the art according to the structure of a formula including the "benzene group."

Examples of the monovalent $C_3$-$C_{60}$ carbocyclic group and the monovalent $C_1$-$C_{60}$ heterocyclic group include a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, and examples of the divalent $C_3$-$C_{60}$ carbocyclic group and the monovalent $C_1$-$C_{60}$ heterocyclic group include a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic condensed polycyclic group, and a substituted or unsubstituted divalent non-aromatic condensed heteropolycyclic group.

The term "$C_1$-$C_{60}$ alkyl group," as used herein, refers to a linear or branched aliphatic hydrocarbon monovalent group that has one to sixty carbon atoms, and examples thereof include a methyl group, an ethyl group, an n-propyl group, an isopropyl group, an n-butyl group, a sec-butyl group, an isobutyl group, a tert-butyl group, an n-pentyl group, a tert-pentyl group, neopentyl group, an isopentyl group, a sec-pentyl group, 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group. The term "$C_1$-$C_{60}$ alkylene group," as used herein, refers to a divalent group having substantially the same structure as the $C_1$-$C_{60}$ alkyl group.

The term "$C_2$-$C_{60}$ alkenyl group," as used herein, refers to a monovalent hydrocarbon group having at least one carbon-carbon double bond at a main chain (e.g., in the middle) or at a terminal end (e.g., the terminus) of the $C_2$-$C_{60}$ alkyl group, and examples thereof include an ethenyl group, a propenyl group, and a butenyl group. The term "$C_2$-$C_{60}$ alkenylene group," as used herein, refers to a divalent group having substantially the same structure as the $C_2$-$C_{60}$ alkenyl group.

The term "$C_2$-$C_{60}$ alkynyl group," as used herein, refers to a monovalent hydrocarbon group having at least one carbon-carbon triple bond in at a main chain (e.g., in the middle) or at a terminal end (e.g., the terminus) of the $C_2$-$C_{60}$ alkyl group, and examples thereof include an ethynyl group, and a propynyl group. The term "$C_1$-$C_{60}$ alkynylene group," as used herein, refers to a divalent group having substantially the same structure as the $C_1$-$C_{60}$ alkynyl group.

The term "$C_1$-$C_{60}$ alkoxy group," as used herein, refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group," as used herein, refers to a monovalent saturated hydrocarbon cyclic group having 3 to 10 carbon atoms, and examples thereof include a cyclopropyl group, a cyclobutyl group, a cyclopentyl group, a cyclohexyl group, a cycloheptyl group, a cyclooctyl group, an adamantanyl group, a norbornanyl group (or bicyclo[2.2.1]heptyl group), a bicyclo[1.1.1]pentyl group, a bicyclo[2.1.1]hexyl group, and a bicyclo[2.2.2]octyl group. The term "$C_3$-$C_{10}$ cycloalkylene group," as used herein, refers to a divalent group having substantially the same structure as the $C_3$-$C_{10}$ cycloalkyl group.

The term "$C_1$-$C_{10}$ heterocycloalkyl group," as used herein, refers to a monovalent cyclic group that further includes, in addition to a carbon atom, at least one heteroatom as a ring-forming atom and has 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group," as used herein refers to a divalent group having substantially the same structure as the $C_1$-$C_{10}$ heterocycloalkyl group.

The term "$C_3$-$C_{10}$ cycloalkenyl group," as used herein, refers to a monovalent cyclic group that has three to ten carbon atoms and at least one carbon-carbon double bond in the ring thereof and no aromaticity (e.g., is not aromatic), and examples thereof include a cyclopentenyl group, a cyclohexenyl group, and a cycloheptenyl group. The term "$C_3$-$C_{10}$ cycloalkenylene group," as used herein, refers to a divalent group having substantially the same structure as the $C_3$-$C_{10}$ cycloalkenyl group.

The term "$C_1$-$C_{10}$ heterocycloalkenyl group," as used herein, refers to a monovalent cyclic group that has, in addition to a carbon atom, at least one heteroatom as a ring-forming atom, 1 to 10 carbon atoms, and at least one carbon-carbon double bond in the cyclic structure thereof. Examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group," as used herein, refers to a divalent group having substantially the same structure as the $C_1$-$C_{10}$ heterocycloalkenyl group.

The term "$C_6$-$C_{60}$ aryl group," as used herein, refers to a monovalent group having a carbocyclic aromatic system having six to sixty carbon atoms, and the term "$C_6$-$C_{60}$ arylene group," as used herein, refers to a divalent group having a carbocyclic aromatic system having six to sixty carbon atoms. Examples of the $C_6$-$C_{60}$ aryl group include a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, and an ovalenyl group. When the $C_6$-$C_{60}$ aryl group and the $C_6$-$C_{60}$ arylene group each include two or more rings, the rings may be condensed with each other (e.g., combined together with each other).

The term "$C_1$-$C_{60}$ heteroaryl group" as used herein refers to a monovalent group having a heterocyclic aromatic system that has, in addition to a carbon atom, at least one heteroatom as a ring-forming atom, and 1 to 60 carbon atoms. The term "$C_1$-$C_{60}$ heteroarylene group," as used herein, refers to a divalent group having a heterocyclic aromatic system that has, in addition to a carbon atom, at least one heteroatom as a ring-forming atom, and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, and a naphthyridinyl group. When the $C_1$-$C_{60}$ heteroaryl group and the $C_1$-$C_{60}$ heteroarylene group each include two or more rings, the rings may be condensed with each other (e.g., combined together with each other).

The term "monovalent non-aromatic condensed polycyclic group," as used herein, refers to a monovalent group (for example, having 8 to 60 carbon atoms) having two or more rings condensed to each other (e.g., combined together with each other), only carbon atoms as ring-forming atoms, and no aromaticity in its entire molecular structure (e.g., is not aromatic when considered as a whole). Examples of the monovalent non-aromatic condensed polycyclic group include an indenyl group, a fluorenyl group, a spiro-bifluorenyl group, a benzofluorenyl group, an indeno phenanthrenyl group, and an indeno anthracenyl group. The term "divalent non-aromatic condensed polycyclic group," as used herein, refers to a divalent group having substantially the same structure as a monovalent non-aromatic condensed polycyclic group.

The term "monovalent non-aromatic condensed heteropolycyclic group," as used herein, refers to a monovalent group (for example, having 1 to 60 carbon atoms) having two or more rings condensed to each other (e.g., combined together with each other), at least one heteroatom other than carbon atoms, as a ring-forming atom, and no aromaticity in its entire molecular structure (e.g., is not aromatic when considered as a whole). Examples of the monovalent non-aromatic condensed heteropolycyclic group are a pyrrolyl group, a thiophenyl group, a furanyl group, an indolyl group, a benzoindolyl group, a naphthon indolyl group, an isoindolyl group, a benzoisoindolyl group, a naphthoisoindolyl group, a benzosilolyl group, a benzothiophenyl group, a benzofuranyl group, a carbazolyl group, a dibenzosilolyl group, a dibenzothiophenyl group, a dibenzofuranyl group, an azacarbazolyl group, an azafluorenyl group, an azadibenzosilolyl group, an azadibenzothiophenyl group, an azadibenzofuranyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a benzopyrazolyl group, a benzimidazolyl group, a benzoxazolyl group, a benzothiazolyl group, a benzoxadiazolyl group, a benzothiadiazolyl group, an imidazopyridinyl group, an imidazopyrimidinyl group, an imidazotriazinyl group, an imidazopyrazinyl group, an imidazopyridazinyl group, an indeno carbazolyl group, an indolocarbazolyl group, a benzofurocarbazolyl group, a benzothienocarbazolyl group, a benzosilolocarbazolyl group, a benzoindolocarbazolyl group, a benzocarbazolyl group, a benzonaphthofuranyl group, a benzonaphthothiophenyl group, a benzonaphthosilolyl group, a benzofurodibenzofuranyl group, a benzofurodibenzothiophenyl group, and a benzothienodibenzothiophenyl group. The term "divalent non-aromatic heterocondensed polycyclic group," as used herein, refers to a divalent group having substantially the same structure as a monovalent non-aromatic heterocondensed polycyclic group.

The term "$C_6$-$C_{60}$ aryloxy group," as used herein, indicates —$OA_{102}$ (wherein $A_{102}$ is the $C_6$-$C_{60}$ aryl group), and the term "$C_6$-$C_{60}$ arylthio group," as used herein, indicates —$SA_{103}$ (wherein $A_{103}$ is the $C_6$-$C_{60}$ aryl group).

The term "$R_{10a}$," as used herein, refers to:
deuterium (-D), —F, —Cl, —Br, —I, a hydroxyl group, a cyano group, or a nitro group;
a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof;
a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof; or
—Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$).

$Q_1$ to $Q_3$, $Q_{11}$ to $Q_{13}$, $Q_{21}$ to $Q_{23}$ and $Q_{31}$ to $Q_{33}$ used herein may each independently be: hydrogen; deuterium; —F; —Cl; —Br; —I; a hydroxyl group; a cyano group; a nitro group; $C_1$-$C_{60}$ alkyl group; $C_2$-$C_{60}$ alkenyl group; $C_2$-$C_{60}$ alkynyl group; $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

The term "hetero atom," as used herein, refers to any atom other than a carbon atom. Examples of the heteroatom are O, S, N, P, Si, B, Ge, Se, and any combination thereof.

The term "Ph," as used herein, refers to a phenyl group, the term "Me," as used herein, refers to a methyl group, the term "Et," as used herein, refers to an ethyl group, the term "ter-Bu" or "Bu$^t$," as used herein, refers to a tert-butyl group, and the term "OMe," as used herein, refers to a methoxy group.

The term "biphenyl group," as used herein, refers to "a phenyl group substituted with a phenyl group." In other words, the "biphenyl group" is a substituted phenyl group having a $C_6$-$C_{60}$ aryl group as a substituent.

The term "terphenyl group," as used herein, refers to "a phenyl group substituted with a biphenyl group." In other words, the "terphenyl group" is a substituted phenyl group having, as a substituent, a $C_6$-$C_{60}$ aryl group substituted with a $C_6$-$C_{60}$ aryl group.

* and *', as used herein, unless defined otherwise, each refer to a binding site to a neighboring atom in a corresponding formula.

Method of Manufacturing Light-Emitting Device

A method of manufacturing a light-emitting device according to another aspect of an embodiment includes forming a hole transport region on a first electrode,
wherein, the forming of the hole transport region includes a solution process using a hole transport composition.

The hole transport composition may be understand based on the description provided in the present specification.

The solution process may be performed by spin coating, slot coating, dip coating, bar coating, roll coating, gravure coating, microgravure coating, wire coating, spray coating, inkjet printing, nozzle printing, screen printing, flexo printing, offset printing, and/or casting.

In an embodiment, the forming of the hole transport region may further include thermally curing and/or photocuring the azide-based compound and a polymer compound, and/or removing the solvent,
wherein the removing of the solvent may be performed at a temperature of 150° C. to 250° C., for example, 180° C. to 220° C.

According to an embodiment, the method of manufacturing the light-emitting device may further include forming an emission layer on the hole transport region, wherein:
the forming of the emission layer may include a solution process using a second composition, and the second composition may include a host material, a dopant material, and a second solvent.

Regarding the second composition, the second solvent is the same as described above, and the host material and the dopant material are the same as described above.

Hereinafter, a compound according to embodiments and an light-emitting device according to embodiments will be described in more detail with reference to Synthesis Examples and Examples. The wording "B was used instead of A" used in describing Synthesis Examples refers to that an identical molar equivalent of B was used in place of A.

SYNTHESIS EXAMPLE

Synthesis Example 1: Synthesis of Compound 1

A mixture of 5-bromoindoline (10 g, 47 mmol) and POCl$_3$ (50 mL) was stirred at 100° C. for 8 hours, and then the reactants were added to water having a temperature of 0° C. and the resultant was neutralized using NaOH. The neutralized brown precipitate was purified by column and recrystallized in acetone to obtain a yellow solid (5.2 g, 57%).

In a flask under a nitrogen atmosphere, the yellow intermediate (5.2 g, 9 mmol) and sodium azide (2.8 g, 43 mol, 4.8 eq) were dissolved in a dimethylformamide (DMF) solvent, and then, stirred for 12 hours at room temperature, and purified by column, thereby obtaining Compound 1 having a yield of 95%.

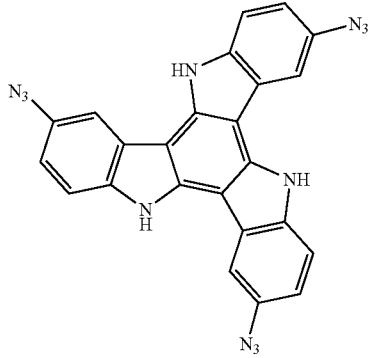

Compound 1

Synthesis Example 2: Synthesis of Compound 2

A mixture of 2-indolinone (10 g, 75 mmol) and POCl$_3$ (50 mL) was stirred at 100° C. for 8 hours, and then the reactants were added to water having a temperature of 0° C. and the resultant was neutralized using NaOH. The neutralized brown precipitate was purified by column and recrystallized in acetone to obtain a yellow solid (5.3 g, 61%).

In a flask under a nitrogen atmosphere, the first yellow intermediate (5.3 g, 15 mmol) and sodium hydride (1.2 g, 53 mmol, 3.5 eq) were dissolved in a DMF solvent, stirred at room temperature for 30 minutes, and then 1-bromo-2-iodoethane (14 g, 60 mmol, 4 eq) was added thereto via a syringe and refluxed for 2 hours. The reactants were added to water and extracted with DCM, and water was removed therefrom by using MgSO$_4$. Column purification was performed thereon to obtain a second yellow Intermediate (8.2 g, 82%). In a flask under a nitrogen atmosphere, the second yellow intermediate (8.2 g, 12 mmol) and sodium azide (3.8 g, 59 mol, 4.8 eq) were dissolved in a DMF solvent, and then, stirred for 12 hours at room temperature, and purified by column, thereby obtaining Compound 2 having a yield of 92%.

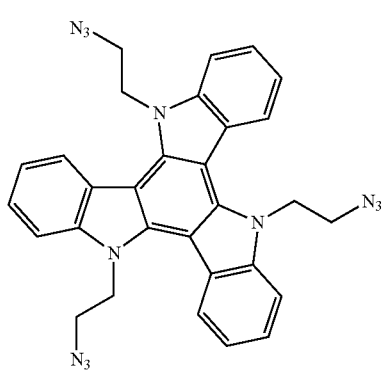

Compound 2

Synthesis Example 3: Synthesis of Compound 3

A mixture of 2-indolinone (10 g, 75 mmol) and POCl$_3$ (50 mL) was stirred at 100° C. for 8 hours, and then the reactants were added to water having a temperature of 0° C. and the resultant was neutralized using NaOH. The neutralized brown precipitate was purified by column and recrystallized in acetone to obtain a yellow solid (5.3 g, 61%).

In a flask under a nitrogen atmosphere, the first yellow intermediate (5.3 g, 15 mmol) and sodium hydride (1.2 g, 53 mmol, 3.5 eq) were dissolved in a DMF solvent, stirred at room temperature for 30 minutes, and then 1-bromo-10-iododecane (21 g, 60 mmol, 4 eq) was added thereto via a syringe and refluxed for 2 hours. The reactants were added to water and extracted with DCM, and water was removed therefrom by using MgSO$_4$. Column purification was performed thereon to obtain a second yellow Intermediate (10.3 g, 68%).

In a flask under a nitrogen atmosphere, the second yellow intermediate (10.3 g, 10 mmol) and sodium azide (3.2 g, 49 mol, 4.8 eq) were dissolved in a DMF solvent, and then, stirred for 12 hours at room temperature, and purified by column, thereby obtaining Compound 3 having a yield of 90%.

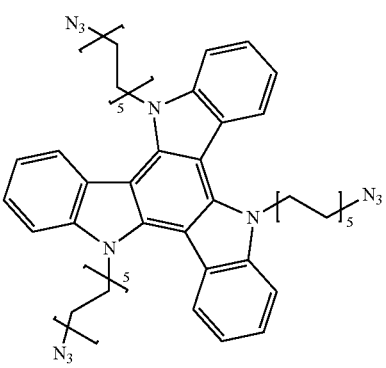

Compound 3

Synthesis Example 4: Synthesis of Compound 4

A mixture of 2-indolinone (10 g, 75 mmol) and POCl$_3$ (50 mL) were stirred at 100° C. for 8 hours, and then the reactants were added to water having a temperature of 0° C. and the resultant was neutralized using NaOH. The neutralized brown precipitate was purified by column and recrystallized in acetone to obtain a yellow solid (5.3 g, 61%).

In a flask under a nitrogen atmosphere, the first yellow intermediate (5.3 g, 15 mmol) and sodium hydride (1.2 g, 53 mmol, 3.5 eq) were dissolved in a DMF solvent, stirred at room temperature for 30 minutes, and then 1-chloro-20-iodoicosane (26 g, 60 mmol, 4 eq) was added thereto via a syringe and refluxed for 2 hours. The reactants were added to water and extracted with DCM, and water was removed therefrom by using MgSO$_4$. Column purification was performed thereon to obtain a second yellow Intermediate (8.3 g, 63%).

In a flask under a nitrogen atmosphere, the second yellow intermediate (8.3 g, 9.5 mmol) and sodium azide (3.0 g, 46 mol, 4.8 eq) were dissolved in a DMF solvent, and then, stirred for 12 hours at room temperature, and purified by column, thereby obtaining Compound 4 having a yield of 86%.

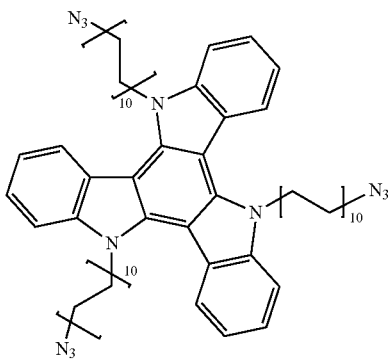

Compound 4

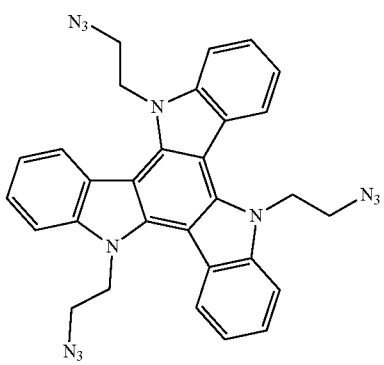

Compound 2

$^1$H NMR results of the compounds synthesized according to Synthesis Examples above are shown in Table 1 below.

TABLE 1

| Compound No. | $^1$H NMR (CDCl$_3$, 400 MHz) |
|---|---|
| 1 | 11.8 (s, 3H), 8.03 (s, 3H), 7.5-7.8 (m, 6H), |
| 2 | 8.3 (d, 3H), 7.3-7.7 (m, 9H), 3.9 (t, 6H), 1.9 (t, 6H) |
| 3 | 8.3 (d, 3H), 7.3-7.7 (m, 9H), 4.2 (t, 6H), 1.7 (m, 6H), 1.5 (t, 6H), 1.2-1.4 (m, 42H) |
| 4 | 8.3 (d, 3H), 7.3-7.7 (m, 9H), 4.2 (t, 6H), 1.7 (m, 6H), 1.5 (t, 6H), 1.2-1.4 (m, 102H) |

Synthesis methods for compounds other than the compounds shown in Table 1 may be easily recognized by those skilled in the technical field by referring to the synthesis paths and source materials described above.

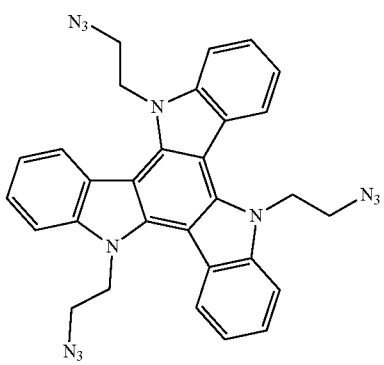

Compound 3

EXAMPLES

Preparation of Hole Transport Composition 1

1.5% compound 1 in an anisole solvent was used as a hole transport composition 1.

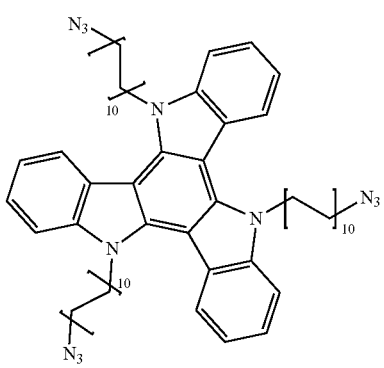

Compound 4

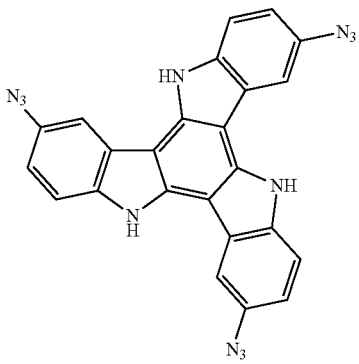

Compound 1

Manufacture of Hole Transport Compositions 2 to 4 and Comparative Compositions 1 to 5

Hole transport compositions 2 to 4 and comparative compositions 1 to 5 were prepared in substantially the same manner as used to prepare hole transport composition 1, except that the compounds shown in Table 2 were used instead of Compound 1.

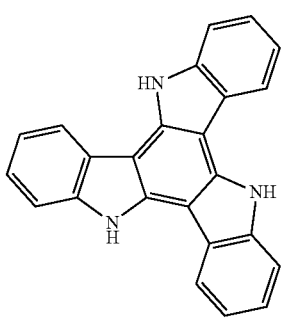

Triindole

Compound A

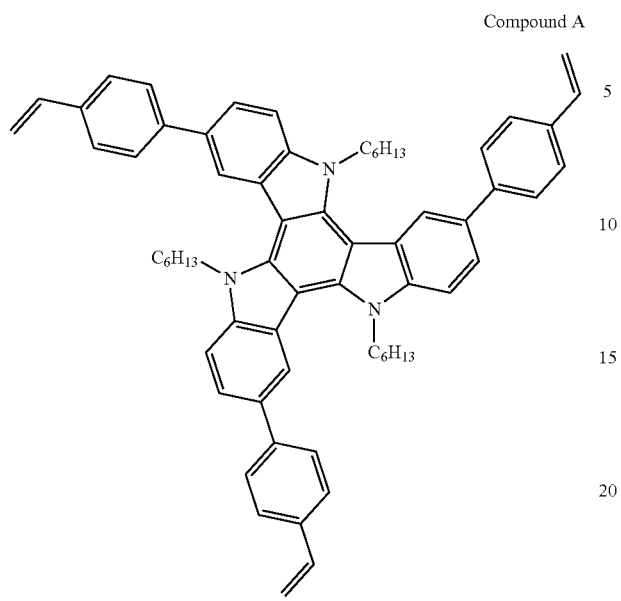

Compound B

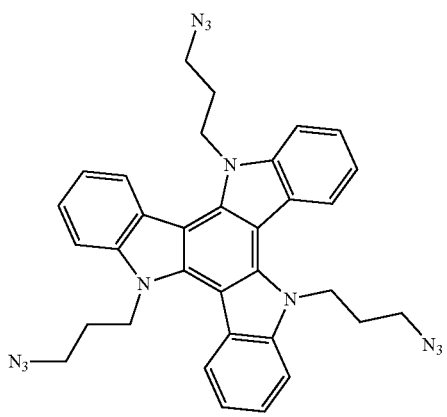

Compound C

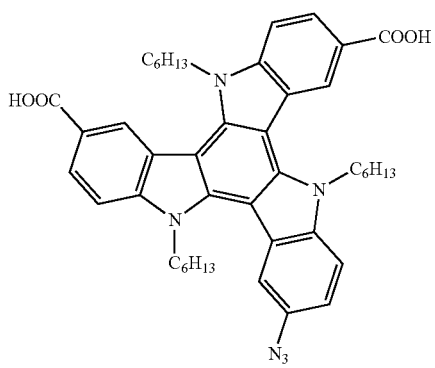

Compound D

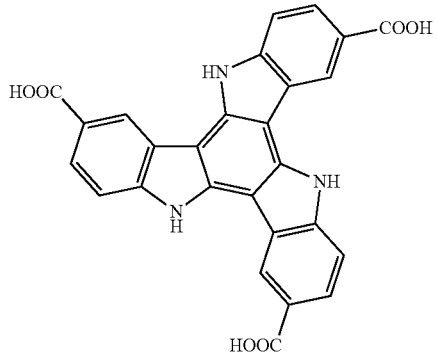

Evaluation Example 1

The hole transport compositions 1 to 4 and the comparative compositions 1 to 5 were each used to form a single film with a thickness of 400 Å, and then, heat treated at 200° C. for 30 minutes to measure the ultraviolet (UV) spectrum of the single film.

50 μl of methyl benzoate was dropped on each single film, and then left intact for 30 minutes. Then, the solvent was absorbed by using a wipe, and the respective singe films were left at 100° C. for 1 minute. The UV spectrum of each single film was measured.

For each single film, the residual film ratio calculated as set forth below is shown in Table 2.

Residual film ratio=(the UV measurement area after dropping the solvent (methyl benzoate)(solvent treatment) and leaving for 30 minutes)/(the UV measurement area before solvent treatment)

In addition, regarding the hole transport compositions 1 to 4 and the comparison compositions 1 to 5, hole mobility was measured using space charge limited current, and the results are shown in Table 2 below.

TABLE 2

| Composition | Compound | Residual film ratio (%) | Hole mobility (cm²/Vs) |
|---|---|---|---|
| Hole transport composition 1 | Compound 1 | 100 | $1.2 \times 10^{-2}$ |
| Hole transport composition 2 | Compound 2 | 100 | $8.5 \times 10^{-3}$ |
| Hole transport composition 3 | Compound 3 | 100 | $5.6 \times 10^{-3}$ |
| Hole transport composition 4 | Compound 4 | 100 | $1.2 \times 10^{-3}$ |
| Comparison composition 1 | Triindole | 0 | $2.0 \times 10^{-2}$ |
| Comparison composition 2 | Compound A | 100 | $5.4 \times 10^{-4}$ |
| Comparison composition 3 | Compound B | 100 | $0.9 \times 10^{-3}$ |
| Comparison composition 4 | Compound C | 100 | $7.0 \times 10^{-4}$ |
| Comparison composition 5 | Compound D | 0 | $2.6 \times 10^{-4}$ |

Referring to Table 2, it can be seen that a hole transport composition including the heterocyclic compound according to an embodiment facilitates the formation of a single film and has excellent hole mobility. For example, hole transport compositions 1 to 4 had better hole mobility than comparative compositions 2 to 5. In the case of comparative composition 1 and comparative composition 5, a single film was not formed.

Light-emitting devices including the heterocyclic compound according to embodiments of the present disclosure may have high efficiency and long lifespan.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims, and equivalents thereof.

What is claimed is:

1. A heterocyclic compound represented by Formula 1:

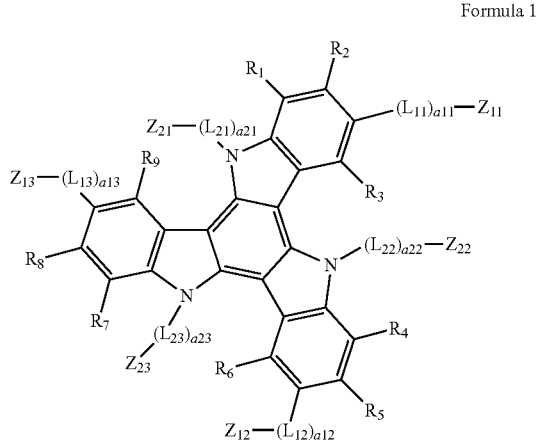

Formula 1 wherein, in Formula 1, $L_{11}$ to $L_{13}$ and $L_{21}$ to $L_{23}$ are each independently a $C_2$-$C_{20}$ alkenylene group unsubstituted or substituted with at least one $R_{10a}$, or a $C_2$-$C_{20}$ alkynylene group unsubstituted or substituted with at least one $R_{10a}$, a11 to a13 and a21 to a23 are each independently 0, 1, 2, 3, 4, or 5, wherein at least one selected from a11 to a13 and a21 to a23 is 1, 2, 3, 4, or 5, $Z_{11}$ to $Z_{13}$, $Z_{21}$ to $Z_{23}$, and $R_1$ to $R_9$ are each independently hydrogen, deuterium, an azide group (—$N_3$), —F, —Cl, —Br, —I, a hydroxyl group, a cyano group, a nitro group, an amidino group, a hydrazino group, a hydrazono group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a $C_1$-$C_{60}$ heteroaryloxy group unsubstituted or substituted with at least one $R_{10a}$, a $C_1$-$C_{60}$ heteroarylthio group unsubstituted or substituted with at least one $R_{10a}$, a monovalent non-aromatic condensed polycyclic group unsubstituted or substituted with at least one $R_{10a}$, a monovalent non-aromatic condensed heteropolycyclic group unsubstituted or substituted with at least one $R_{10a}$, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), or —P(=S)($Q_1$)($Q_2$), at least one selected from $Z_{11}$ to $Z_{13}$, $Z_{21}$ to $Z_{23}$, and $R_1$ to $R_9$ is —$N_3$, when each of $Z_{11}$ to $Z_{13}$ is —$N_3$, at least one selected from -($L_{21}$)$_{a21}$-$Z_{21}$, -($L_{22}$)$_{a22}$-$Z_{22}$, and -($L_{23}$)$_{a23}$-$Z_{23}$ is hydrogen, $R_{10a}$ is:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof; or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ are each independently: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

2. The heterocyclic compound of claim 1, wherein $Z_{11}$ to $Z_{13}$ are each —$N_3$.

3. The heterocyclic compound of claim 1, wherein $Z_{21}$ to $Z_{23}$ are each —$N_3$.

4. The heterocyclic compound of claim 1, wherein the heterocyclic compound is represented by one selected from Formulae 2A and 2B:

Formula 2A

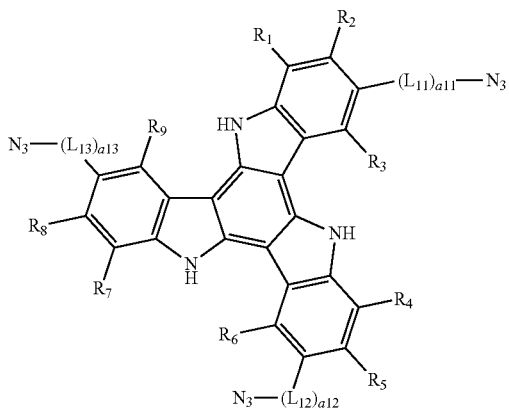

Formula 2B

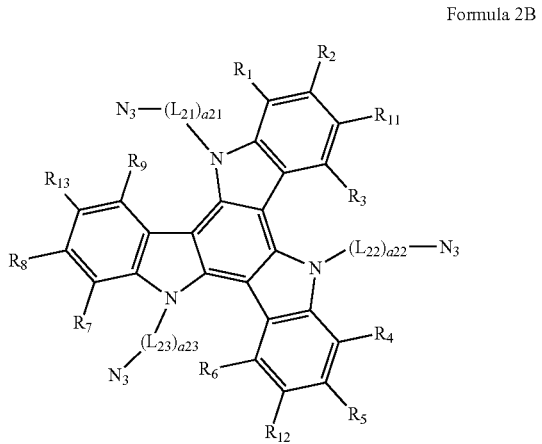

wherein, in Formulae 2A and 2B, $L_{11}$ to $L_{13}$, $L_{21}$ to $L_{23}$, $Z_{11}$ to $Z_{13}$, $Z_{21}$ to $Z_{23}$, and $R_1$ to $R_9$ are the same as described in claim 1, $R_{11}$ to $R_{13}$ are each independently hydrogen, deuterium, —F, —Cl, —Br, —I, a hydroxyl group, a cyano group, a nitro group, an amidino group, a hydrazino group, a hydrazono group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a $C_1$-$C_{60}$ heteroaryloxy group unsubstituted or substituted with at least one $R_{10a}$, a $C_1$-$C_{60}$ heteroarylthio group unsubstituted or substituted with at least one $R_{10a}$, a monovalent non-aromatic condensed polycyclic group unsubstituted or substituted with at least one $R_{10a}$, a monovalent non-aromatic condensed heteropolycyclic group unsubstituted or substituted with at least one $R_{10a}$, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), or —P(=S)($Q_1$)($Q_2$), and $R_{10a}$ is the same as described in claim 1.

5. The heterocyclic compound of claim 1, wherein $R_1$ to $R_9$ are each independently:

hydrogen, deuterium, —F, —Cl, —Br, —I, a cyano group, a $C_1$-$C_{20}$ alkyl group, or a $C_1$-$C_{20}$ alkoxy group, a $C_1$-$C_{20}$ alkyl group or a $C_1$-$C_{20}$ alkoxy group, each substituted with deuterium, —F, —Cl, —Br, —I, a cyano group, a phenyl group, a biphenyl group, or any combination thereof; or a group represented by one selected from Formulae 5-1 to 5-26 and Formulae 6-1 to 6-55:

5-1
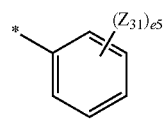

5-2
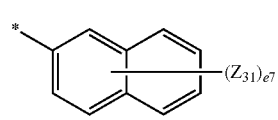

5-3
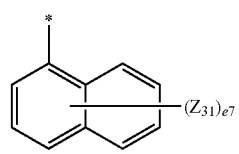

5-4
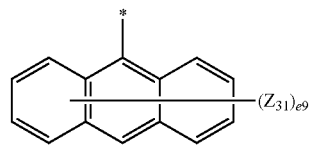

5-5
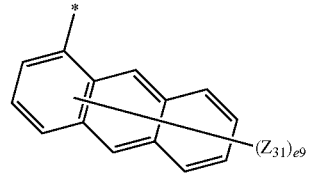

5-6
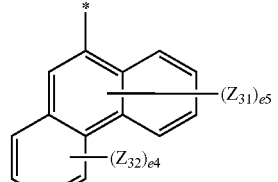

5-7
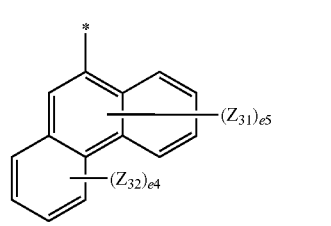

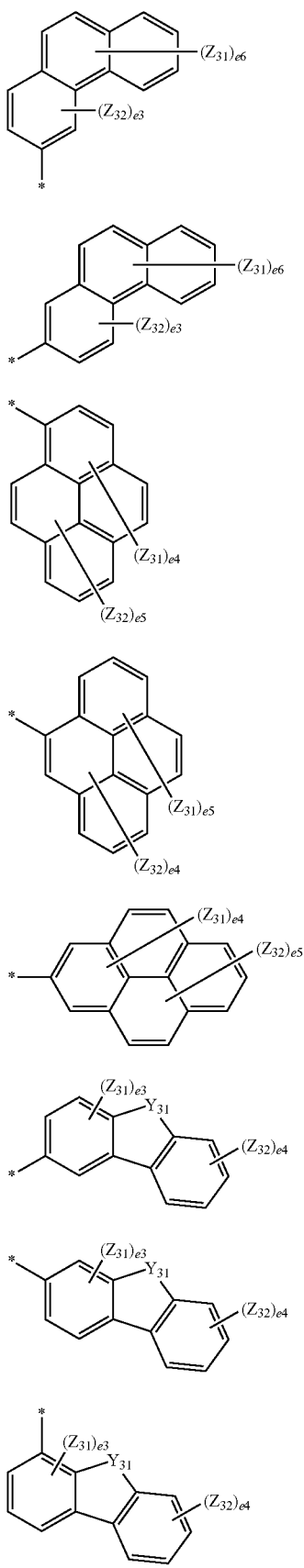
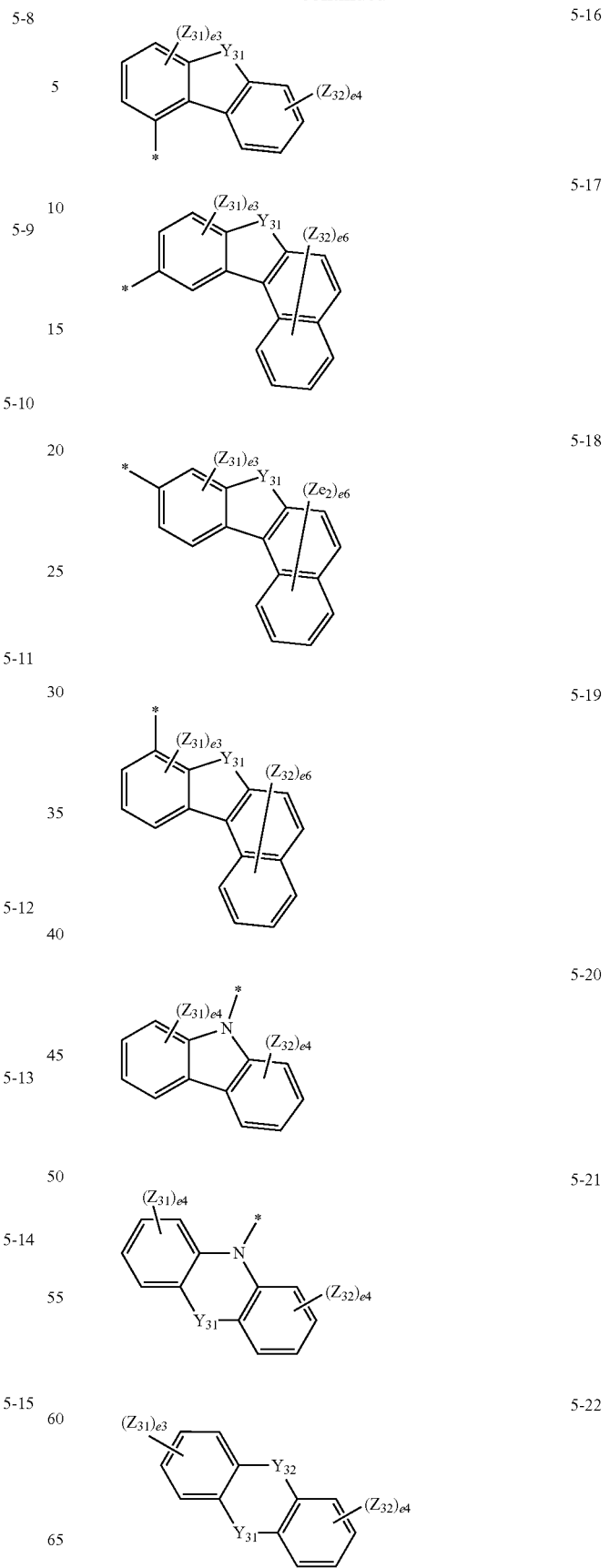

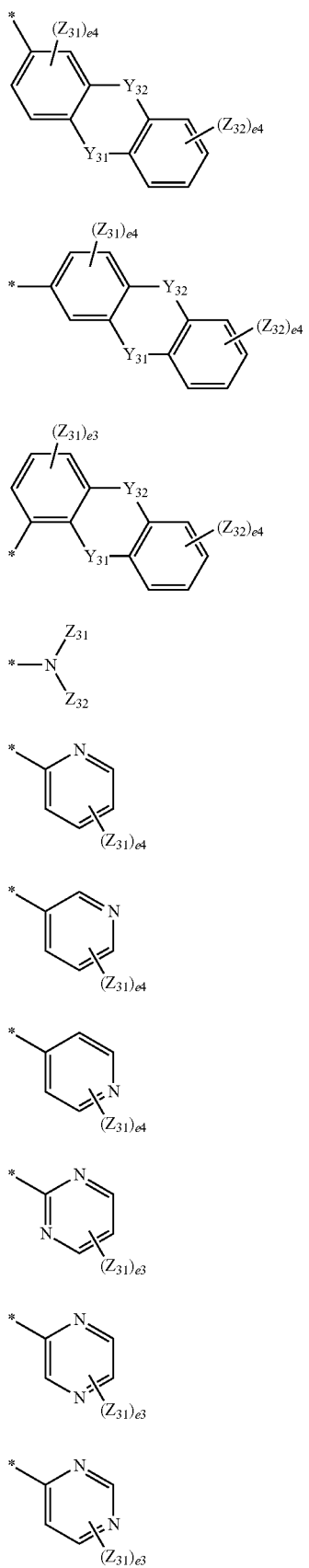
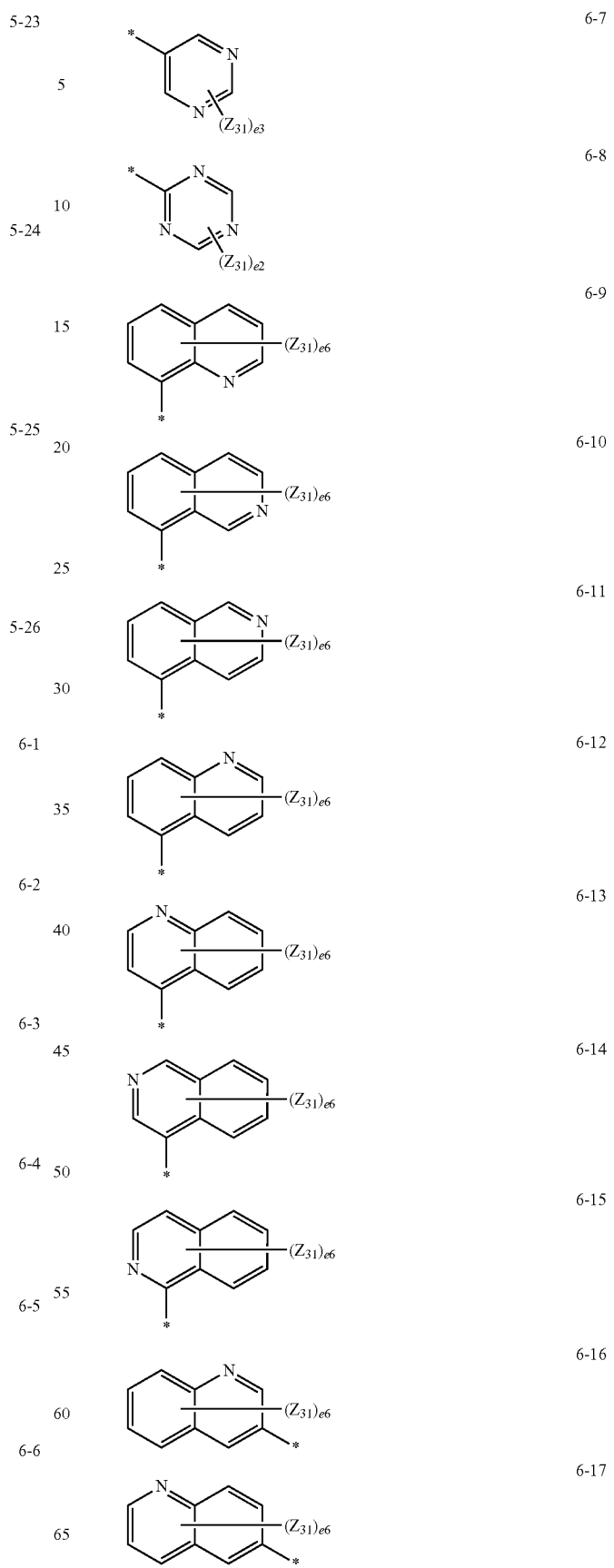

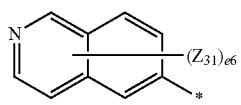 6-4
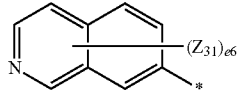 6-5
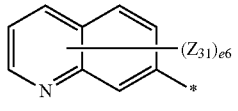 6-6
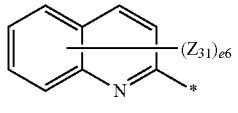 6-7
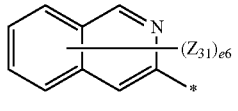 6-8
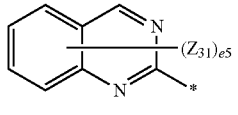 6-9
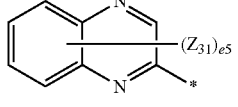 6-10
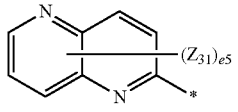 6-11
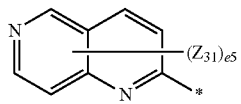 6-12
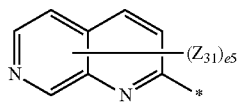 6-13
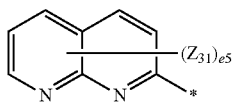 6-14
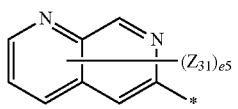 6-15
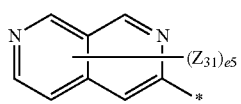 6-16
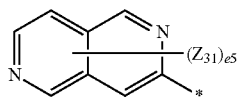 6-17
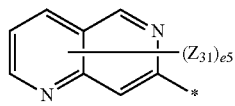 6-18
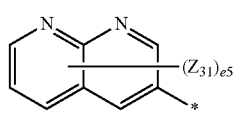 6-19
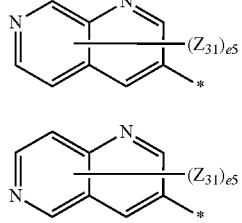 6-20
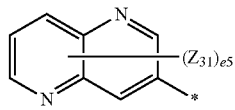 6-21
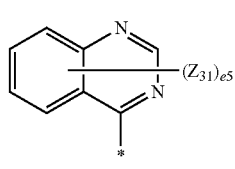 6-22
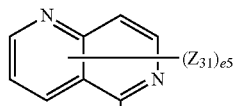 6-23
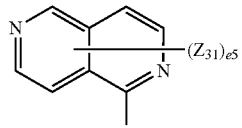 6-24
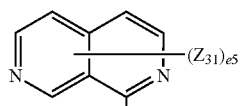 6-25
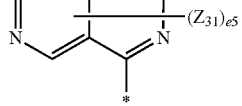 6-26
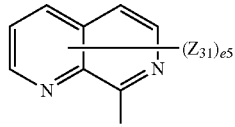 6-27
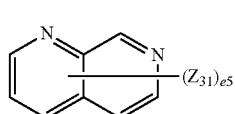 6-28

6-43 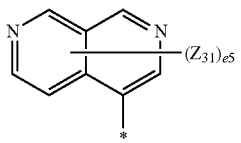

6-44 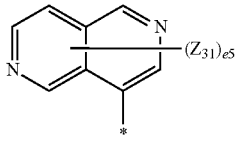

6-45 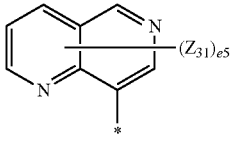

6-46 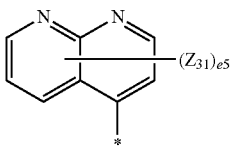

6-47 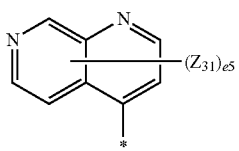

6-48 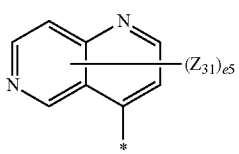

6-49 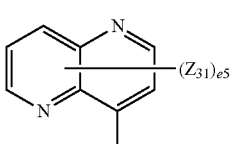

6-50 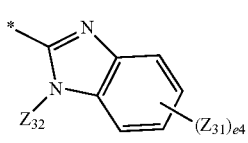

6-51 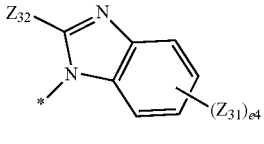

6-52 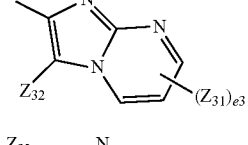

6-53 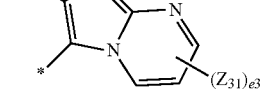

6-54 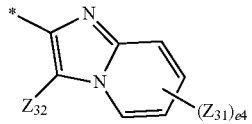

6-55 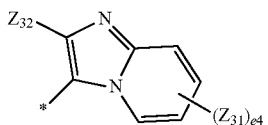

wherein, in Formulae 5-1 to 5-26 and 6-1 to 6-55, $Y_{31}$ and $Y_{32}$ are each independently O, S, $C(Z_{33})(Z_{34})$, $N(Z_{33})$, or $Si(Z_{33})(Z_{34})$, $Z_{31}$ to $Z_{34}$ are each independently selected from hydrogen, deuterium, —F, —Cl, —Br, —I, a hydroxyl group, a hydroxyl group, a cyano group, a nitro group, an amidino group, a hydrazino group, a hydrazono group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a biphenyl group, a terphenyl group, a naphthyl group, a fluorenyl group, a spiro-bifluorenyl group, a phenanthrenyl group, an anthracenyl group, a triphenylenyl group, a pyridinyl group, a pyrimidinyl group, a carbazolyl group, and a triazinyl group, e2 is 1 or 2,
e3 is an integer from 1 to 3,
e4 is an integer from 1 to 4,
e5 is an integer from 1 to 5,
e6 is an integer from 1 to 6,
e7 is an integer from 1 to 7,
e9 is an integer from 1 to 9, and
* indicates a binding site to a neighboring atom.

6. The heterocyclic compound of claim 1, wherein $R_1$ to $R_9$ are each independently:

hydrogen, deuterium, —F, —Cl, —Br, —I, a cyano group, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with deuterium, —F, —Cl, —Br, —I, a cyano group, a phenyl group, a biphenyl group, or any combination thereof;

a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a carbazolyl group, an acridinyl group, a dibenzofuranyl group, a dibenzothiophenyl group, a benzocarbazolyl group, or a dibenzocarbazolyl group; or a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a carbazolyl group, an acridinyl group, a dibenzofuranyl group, a dibenzothiophenyl group, a benzocarbazolyl group, or a dibenzocarbazolyl group, each substituted with deuterium, —F, —Cl, —Br, —I, a cyano group, a $C_1$-$C_{20}$ alkyl group, a $C_1$-$C_{20}$ alkoxy group, a phenyl group, a biphenyl group, or any combination thereof.

7. The heterocyclic compound of claim 1, wherein the heterocyclic compound is represented by one selected from Formulae 3A-3 and 3B-2:

Formula 3A-3

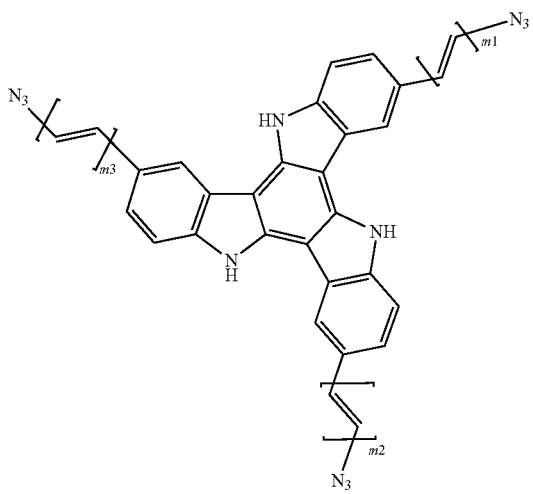

Formula 3B-2

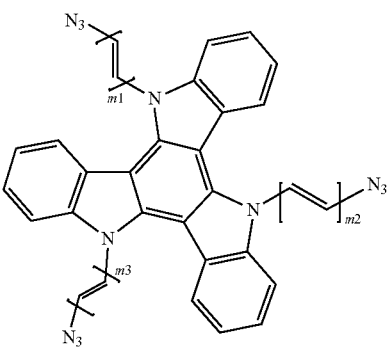

wherein, in Formulae 3A-3 and 3B3-2,
m1, m2, and m3 are each 1, 2, 3, 4, or 5.

8. The heterocyclic compound of claim 1, wherein the heterocyclic compound represented by Formula 1 is one selected from compounds 6 and 7:

Compound 6

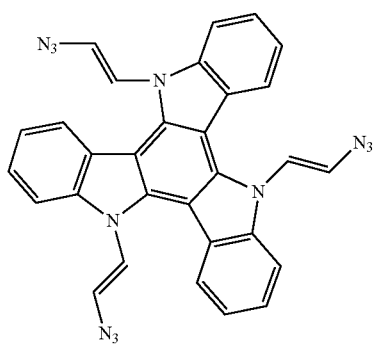

Compound 7

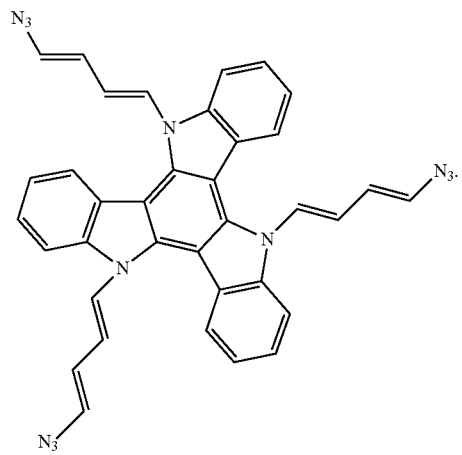

9. A hole transport composition comprising the heterocyclic compound of claim 1.

10. The hole transport composition of claim 9, wherein the hole transport composition further comprises a solvent, and
the solvent comprises a $C_6$-$C_{20}$ aliphatic hydrocarbon, a $C_5$-$C_{20}$ aromatic hydrocarbon, chloroform, methylene chloride, ethyl acetate, ethylene glycol, diethylene glycol, or any combination thereof.

11. A light-emitting device comprising:
a first electrode;
a second electrode facing the first electrode;
an interlayer between the first electrode and the second electrode and comprising an emission layer,
wherein the light-emitting device comprises:
a heterocyclic compound represented by Formula 1;
a polymer comprising a repeating unit derived from the heterocyclic compound represented by Formula 1; or
any combination of a heterocyclic compound represented by Formula 1 and a polymer comprising a repeating unit derived from the heterocyclic compound represented by Formula 1, Formula 1

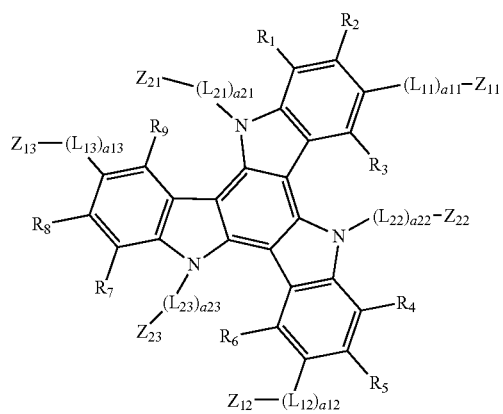

wherein, in Formula 1,
$L_{11}$ to $L_{13}$ and $L_{21}$ to $L_{23}$ are each independently a $C_2$-$C_{20}$ alkenylene group unsubstituted or substituted with at least one $R_{10a}$, or a $C_2$-$C_{20}$ alkynylene group unsubstituted or substituted with at least one $R_{10a}$, a11 to a13 and a21 to a23 are each independently 0, 1, 2, 3, 4, or 5, wherein at least one selected from a11 to a13 and a21 to a23 is 1, 2, 3, 4, or 5, $Z_{11}$ to $Z_{13}$, $Z_{21}$ to $Z_{23}$, and $R_1$ to $R_9$ are each independently hydrogen, deuterium, an azide group (—$N_3$), —F, —Cl, —Br, —I, a hydroxyl group, a cyano group, a nitro group, an amidino group, a hydrazino group, a hydrazono group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a $C_1$-$C_{60}$ heteroaryloxy group unsubstituted or substituted with at least one $R_{10a}$, a $C_1$-$C_{60}$ heteroarylthio group unsubstituted or substituted with at least one $R_{10a}$, a monovalent non-aromatic condensed polycyclic group unsubstituted or substituted with at least one $R_{10a}$, a monovalent non-aromatic condensed heteropolycyclic group unsubstituted or substituted with at least one $R_{10a}$, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), or —P(=S)($Q_1$)($Q_2$), at least one selected from $Z_{11}$ to $Z_{13}$, $Z_{21}$ to $Z_{23}$, and $R_1$ to $R_9$ is —$N_3$, when each of $Z_{11}$ to $Z_{13}$ is —$N_3$, at least one selected from -($L_{21}$)$_{a21}$-$Z_{21}$, -($L_{22}$)$_{a22}$-$Z_{22}$, and -($L_{23}$)$_{a23}$-$Z_{23}$ is hydrogen, $R_{10a}$ is:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof; or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ are each independently: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof.

12. The light-emitting device of claim 11, wherein the repeating unit derived from the heterocyclic compound is represented by any one selected from Formulae 1-1 to 1-4:

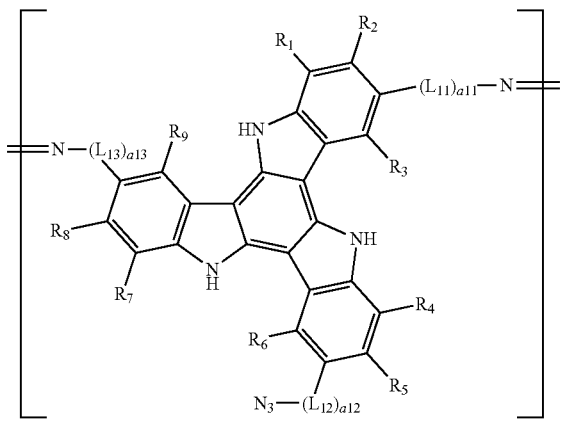

Formula 1-1

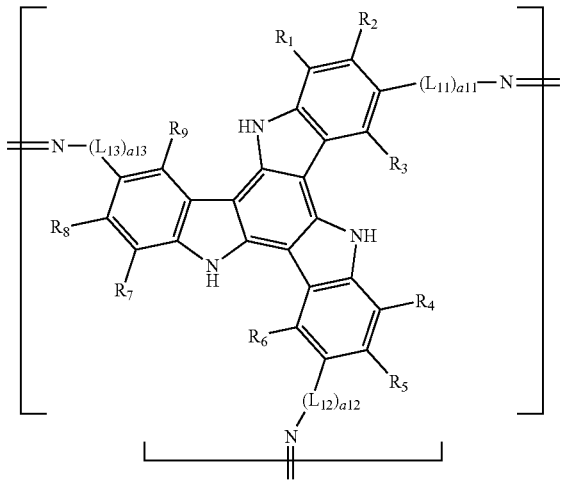

Formula 1-2

Formula 1-3

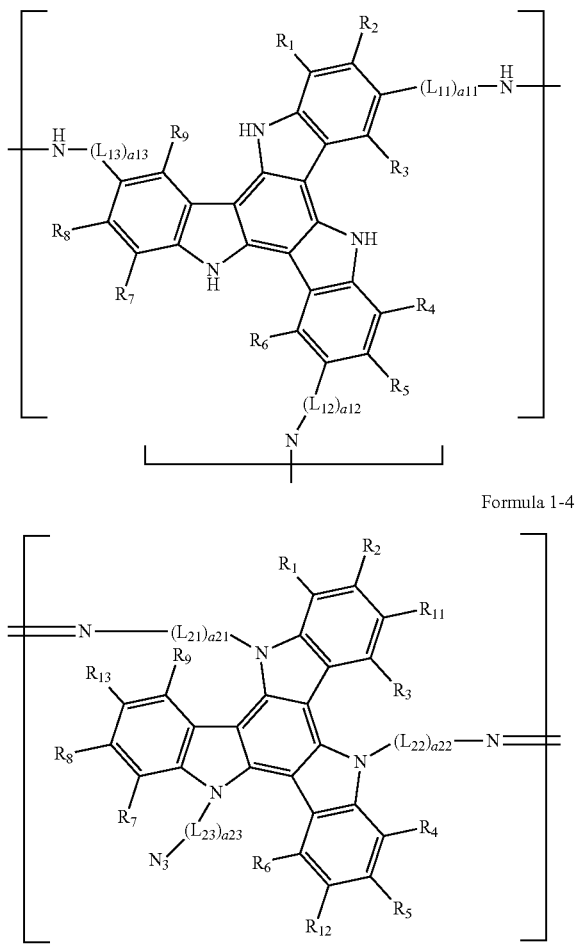

Formula 1-4 wherein, in Formulae 1-1 to 1-4

$L_{11}$ to $L_{13}$, $L_{21}$ to $L_{23}$, and $R_1$ to $R_9$ are the same as described in connection with Formula 1, $R_{11}$ to $R_{13}$ are each independently hydrogen, deuterium, —F, —Cl, —Br, —I, a hydroxyl group, a cyano group, a nitro group, an amidino group, a hydrazino group, a hydrazono group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a $C_1$-$C_{60}$ heteroaryloxy group unsubstituted or substituted with at least one $R_{10a}$, a $C_1$-$C_{60}$ heteroarylthio group unsubstituted or substituted with at least one $R_{10a}$, a monovalent non-aromatic condensed polycyclic group unsubstituted or substituted with at least one $R_{10a}$, a monovalent non-aromatic condensed heteropolycyclic group unsubstituted or substituted with at least one $R_{10a}$, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), or —P(=S)($Q_1$)($Q_2$), and $R_{10a}$ is the same as described in connection with Formula 1.

13. The light-emitting device of claim 11, wherein the first electrode is an anode, the second electrode is a cathode, and the interlayer further comprises a hole transport region between the first electrode and the emission layer, wherein:

the hole transport region comprises the heterocyclic compound, the polymer, or any combination thereof.

14. The light-emitting device of claim 13, wherein the hole transport region comprises at least one selected from a hole injection layer, a hole transport layer, a buffer layer, an emission auxiliary layer, and an electron blocking layer.

15. The light-emitting device of claim 11, wherein the emission layer comprises a host and a dopant.

16. The light-emitting device of claim 11, further comprising an electron transport region between the emission layer and the second electrode, wherein the electron transport region comprises at least one selected from a hole blocking layer, an electron transport layer, and an electron injection layer.

17. A method of manufacturing a light-emitting device, the method comprising forming a hole transport region on a first electrode, wherein the forming of the hole transport region comprises a solution process using a hole transport composition, and the hole transport composition comprises the heterocyclic compound of claim 1.

18. An electronic apparatus comprising the light-emitting device of claim 11.

19. The electronic apparatus of claim 18, further comprising a thin-film transistor, wherein the thin-film transistor comprises a source electrode and a drain electrode, and the first electrode of the light-emitting device is electrically coupled to the source electrode or the drain electrode.

* * * * *